(12) United States Patent
Yamanishi et al.

(10) Patent No.: US 8,986,944 B2
(45) Date of Patent: *Mar. 24, 2015

(54) METHODS AND COMPOSITIONS FOR SEPARATING RARE CELLS FROM FLUID SAMPLES

(75) Inventors: Douglas T. Yamanishi, Carlsbad, CA (US); Paul G. Hujsak, San Diego, CA (US); Sara F. Snyder, San Francisco, CA (US); George Walker, San Diego, CA (US); Junquan Xu, San Diego, CA (US); Mingxian Huang, San Diego, CA (US); Guoliang Tao, San Diego, CA (US); Lei Wu, San Diego, CA (US); Xiaobo Wang, San Diego, CA (US); Joe Ouyang, San Diego, CA (US); Charina Schmitigal, San Diego, CA (US); Jing Cheng, San Diego, CA (US); Jia Xu, San Diego, CA (US)

(73) Assignee: Aviva Biosciences Corporation, San Diego, CA (US)

( * ) Notice: Subject to any disclaimer, the term of this patent is extended or adjusted under 35 U.S.C. 154(b) by 2184 days.

This patent is subject to a terminal disclaimer.

(21) Appl. No.: 11/497,919

(22) Filed: Aug. 2, 2006

(65) Prior Publication Data

US 2007/0202536 A1   Aug. 30, 2007

Related U.S. Application Data

(63) Continuation-in-part of application No. 10/701,684, filed on Nov. 4, 2003, now Pat. No. 7,166,443, which is a continuation-in-part of application No. 10/268,312, filed on Oct. 10, 2002, now Pat. No. 6,949,355.

(60) Provisional application No. 60/704,601, filed on Aug. 2, 2005, provisional application No. 60/348,228, filed on Oct. 29, 2001, provisional application No. 60/328,724, filed on Oct. 11, 2001, provisional application No. 60/394,517, filed on Jul. 9, 2002.

(51) Int. Cl.
| | | |
|---|---|---|
| C12Q 1/24 | (2006.01) | |
| C12Q 1/68 | (2006.01) | |
| G01N 1/40 | (2006.01) | |
| G01N 33/569 | (2006.01) | |
| G01N 33/574 | (2006.01) | |
| B01L 3/00 | (2006.01) | |

(52) U.S. Cl.
CPC ............... *C12Q 1/6881* (2013.01); *G01N 1/40* (2013.01); *G01N 1/4077* (2013.01); *G01N 33/56966* (2013.01); *G01N 33/57407* (2013.01); *B01L 3/5027* (2013.01); *G01N 2333/4724* (2013.01)
USPC ............. 435/30; 435/4; 435/261; 436/177

(58) Field of Classification Search
None
See application file for complete search history.

(56) References Cited

U.S. PATENT DOCUMENTS

| | | | |
|---|---|---|---|
| 3,635,798 A | 1/1972 | Kirkham et al. | |
| 3,975,156 A | 8/1976 | Kraft et al. | |
| 4,326,934 A | 4/1982 | Pohl | |
| 4,413,771 A * | 11/1983 | Rohde et al. | 494/17 |
| 4,699,880 A | 10/1987 | Goldstein | |
| 4,727,021 A | 2/1988 | Cote et al. | |
| 4,786,387 A | 11/1988 | Whitlock | |
| 4,828,991 A | 5/1989 | Hanna, Jr. et al. | |
| 4,910,148 A | 3/1990 | Sorensen et al. | |
| 5,264,554 A | 11/1993 | Newman | |
| 5,288,614 A | 2/1994 | Bodenmuller et al. | |
| 5,437,958 A | 8/1995 | Gallatin et al. | |
| 5,437,987 A | 8/1995 | Teng et al. | |
| 5,482,829 A | 1/1996 | Kass et al. | |
| 5,532,139 A | 7/1996 | Miller | |
| 5,541,072 A | 7/1996 | Wang et al. | |
| 5,543,296 A | 8/1996 | Sobol et al. | |
| 5,576,185 A | 11/1996 | Coulter et al. | |
| 5,597,531 A | 1/1997 | Liberti et al. | |
| 5,610,027 A | 3/1997 | Miller | |
| 5,616,468 A | 4/1997 | Salmi et al. | |
| 5,626,734 A | 5/1997 | Docoslis et al. | |
| 5,629,162 A | 5/1997 | deFougerolles et al. | |
| 5,641,628 A | 6/1997 | Bianchi | |
| 5,646,004 A | 7/1997 | Van Vlasselaer | |
| 5,653,859 A | 8/1997 | Parton et al. | |
| 5,698,271 A | 12/1997 | Liberti et al. | |
| 5,726,026 A | 3/1998 | Wilding et al. | |

(Continued)

FOREIGN PATENT DOCUMENTS

| | | |
|---|---|---|
| CN | 1188528 C | 2/2005 |
| CN | 1880329 | 12/2006 |

(Continued)

OTHER PUBLICATIONS

Ahn et al., IEEE Trans. Magnetics (1994) 30:73-79.
Ahn et al., J. Microelectromechanical Systems (1996) 5:151-158.
Becker et al., Proc. Natl. Acad. Sci. USA (1995) 92:860-864.
Collins, Journal of Immunological Methods (2000) 243:125-145.
De Gasperis et al., Meas. Sci. Technol. (1998) 9:518-529.
Decoslis et al., Biotechnology and Bioengineering (1997) 54(3):239-250.

(Continued)

*Primary Examiner* — Jim Ketter
(74) *Attorney, Agent, or Firm* — Morrison & Foerster LLP

(57) ABSTRACT

The present invention includes methods of enriching rare cells, such as cancer cells, from biological samples, such as blood samples. The methods include performing at least one debulking step on a blood sample and selectively removing at least one type undesirable component from the blood sample to obtain a blood sample that is enriched in a rare cell of interest. In some embodiments magnetic beads coupled to specific binding members are used to selectively removed components.

22 Claims, 31 Drawing Sheets

(56) References Cited

U.S. PATENT DOCUMENTS

| | | |
|---|---|---|
| 5,728,537 A | 3/1998 | Silen et al. |
| 5,766,888 A | 6/1998 | Sobol et al. |
| 5,786,224 A | 7/1998 | Li et al. |
| 5,814,200 A | 9/1998 | Pethig et al. |
| 5,837,115 A | 11/1998 | Austin et al. |
| 5,837,822 A | 11/1998 | Gallatin et al. |
| 5,840,490 A | 11/1998 | Bacchetti et al. |
| 5,866,071 A | 2/1999 | Leu |
| 5,869,262 A | 2/1999 | Gallatin et al. |
| 5,876,593 A | 3/1999 | Liberti et al. |
| 5,877,299 A | 3/1999 | Thomas et al. |
| 5,880,268 A | 3/1999 | Gallatin et al. |
| 5,883,760 A | 3/1999 | Yamada et al. |
| 5,888,370 A | 3/1999 | Becker et al. |
| 5,891,841 A | 4/1999 | deFougerolles et al. |
| 5,905,031 A | 5/1999 | Kuylen et al. |
| 5,922,278 A | 7/1999 | Chapman et al. |
| 5,928,880 A | 7/1999 | Wilding et al. |
| 5,948,278 A | 9/1999 | Sammons et al. |
| 5,993,630 A | 11/1999 | Becker et al. |
| 5,993,665 A | 11/1999 | Terstappen et al. |
| 6,040,176 A | 3/2000 | Gallatin et al. |
| 6,061,074 A | 5/2000 | Bartha et al. |
| 6,071,394 A | 6/2000 | Cheng et al. |
| 6,087,130 A | 7/2000 | Gallatin et al. |
| 6,117,985 A | 9/2000 | Thomas et al. |
| 6,184,043 B1 | 2/2001 | Fodstad et al. |
| 6,187,592 B1 | 2/2001 | Gourley |
| 6,190,870 B1 | 2/2001 | Schmitz et al. |
| 6,197,523 B1 | 3/2001 | Rimm et al. |
| 6,197,593 B1 | 3/2001 | Deka et al. |
| 6,228,652 B1 | 5/2001 | Rodriguez et al. |
| 6,235,534 B1 | 5/2001 | Brookes et al. |
| 6,265,229 B1 | 7/2001 | Fodstad et al. |
| 6,291,249 B1 | 9/2001 | Mahant et al. |
| 6,306,575 B1 | 10/2001 | Thomas et al. |
| 6,355,491 B1 | 3/2002 | Zhou et al. |
| 6,365,362 B1 | 4/2002 | Terstappen et al. |
| 6,482,926 B1 | 11/2002 | Thomas et al. |
| 6,491,918 B1 | 12/2002 | Thomas et al. |
| 6,551,843 B1 | 4/2003 | Rao et al. |
| 6,586,177 B1 | 7/2003 | Shuber |
| 6,596,143 B1 | 7/2003 | Wang et al. |
| 6,620,627 B1 | 9/2003 | Liberti et al. |
| 6,623,982 B1 | 9/2003 | Liberti et al. |
| 6,645,731 B2 | 11/2003 | Terstappen et al. |
| 6,673,541 B1 | 1/2004 | Klein et al. |
| 6,673,618 B1 | 1/2004 | Li et al. |
| 6,727,451 B1 | 4/2004 | Fuhr et al. |
| 6,818,743 B1 | 11/2004 | Gallatin et al. |
| 6,849,403 B1 | 2/2005 | Shuber |
| 6,881,314 B1 | 4/2005 | Wang et al. |
| 6,893,881 B1 | 5/2005 | Fodstad et al. |
| 6,900,029 B1 | 5/2005 | Coulter et al. |
| 6,919,174 B1 | 7/2005 | Shuber |
| 6,949,355 B2 * | 9/2005 | Yamanishi et al. ............. 435/34 |
| 6,969,517 B2 | 11/2005 | Gillies et al. |
| 7,094,378 B1 | 8/2006 | Goodrich, Jr. et al. |
| 7,153,648 B2 | 12/2006 | Jing et al. |
| 7,166,443 B2 | 1/2007 | Walker et al. |
| 7,420,660 B2 | 9/2008 | Muller |
| 7,463,343 B2 | 12/2008 | Muller |
| 7,498,156 B2 | 3/2009 | Goodrich et al. |
| 7,771,658 B2 | 8/2010 | Larsen |
| 7,790,464 B2 | 9/2010 | Tarasev |
| 7,797,990 B2 | 9/2010 | Larsen et al. |
| 7,846,393 B2 | 12/2010 | Tai et al. |
| 7,846,743 B2 | 12/2010 | Tai et al. |
| 7,918,981 B2 | 4/2011 | Jing et al. |
| 8,114,289 B2 | 2/2012 | Zheng et al. |
| 8,227,250 B2 | 7/2012 | Larsen et al. |
| 8,268,244 B2 | 9/2012 | Tarasev et al. |
| 8,288,170 B2 | 10/2012 | Tai et al. |
| 8,426,122 B2 | 4/2013 | Parikh et al. |
| 8,492,686 B2 | 7/2013 | Bilchinsky et al. |
| 8,551,425 B2 | 10/2013 | Goldkorn et al. |
| 8,614,066 B2 | 12/2013 | Wu |
| 8,617,840 B2 | 12/2013 | Godfrin |
| 8,715,920 B2 | 5/2014 | Sehgal |
| 8,774,488 B2 | 7/2014 | Parikh et al. |
| 2001/0018192 A1 | 8/2001 | Terstappen et al. |
| 2001/0029293 A1 | 10/2001 | Gallatin et al. |
| 2002/0009759 A1 | 1/2002 | Terstappen et al. |
| 2002/0022276 A1 | 2/2002 | Zhou et al. |
| 2002/0058030 A1 | 5/2002 | Monroy et al. |
| 2002/0076825 A1 | 6/2002 | Cheng et al. |
| 2002/0122791 A1 | 9/2002 | Nicolette |
| 2002/0172987 A1 | 11/2002 | Terstappen et al. |
| 2003/0129676 A1 | 7/2003 | Terstappen et al. |
| 2003/0134305 A1 | 7/2003 | Dertinger et al. |
| 2003/0134416 A1 | 7/2003 | Yamanishi et al. |
| 2003/0147886 A1 | 8/2003 | Thomas et al. |
| 2003/0170631 A1 | 9/2003 | Houghton et al. |
| 2003/0199423 A1 | 10/2003 | Gallatin et al. |
| 2003/0203507 A1 | 10/2003 | Liberti et al. |
| 2004/0014104 A1 | 1/2004 | Shuber |
| 2004/0023222 A1 | 2/2004 | Russell et al. |
| 2004/0023288 A1 | 2/2004 | Ridder et al. |
| 2004/0029103 A1 | 2/2004 | Robinson et al. |
| 2004/0043467 A1 | 3/2004 | Shuber et al. |
| 2004/0072269 A1 | 4/2004 | Rao et al. |
| 2004/0142463 A1 | 7/2004 | Walker et al. |
| 2004/0248211 A1 | 12/2004 | Gallatin et al. |
| 2005/0158289 A1 | 7/2005 | Simmons et al. |
| 2005/0176020 A1 | 8/2005 | Gallatin et al. |
| 2005/0244404 A1 | 11/2005 | Sumitran-Holgersson et al. |
| 2005/0260766 A1 | 11/2005 | Paul et al. |
| 2006/0008807 A1 | 1/2006 | O'Hara et al. |
| 2006/0014174 A1 | 1/2006 | Georgakopoulos |
| 2006/0252054 A1 | 11/2006 | Lin et al. |
| 2006/0254972 A1 | 11/2006 | Tai et al. |
| 2007/0025883 A1 | 2/2007 | Tai et al. |
| 2007/0202536 A1 | 8/2007 | Yamanishi et al. |
| 2008/0057505 A1 | 3/2008 | Lin et al. |
| 2008/0206757 A1 | 8/2008 | Lin et al. |
| 2009/0188864 A1 | 7/2009 | Zheng et al. |
| 2010/0159506 A1 | 6/2010 | Parikh et al. |
| 2010/0181288 A1 | 7/2010 | Tang et al. |
| 2010/0248257 A1 | 9/2010 | Jacobsen et al. |
| 2010/0273168 A1 | 10/2010 | Krockenberger et al. |
| 2010/0279322 A1 | 11/2010 | Tang et al. |
| 2011/0053052 A1 | 3/2011 | Braun et al. |
| 2011/0111412 A1 | 5/2011 | Tai et al. |
| 2011/0275064 A1 | 11/2011 | Wu et al. |
| 2011/0294206 A1 | 12/2011 | Tai et al. |
| 2012/0021453 A1 | 1/2012 | Patra et al. |
| 2012/0097610 A1 | 4/2012 | Zheng et al. |
| 2012/0178097 A1 | 7/2012 | Tai et al. |
| 2012/0183946 A1 | 7/2012 | Tang et al. |
| 2012/0282598 A1 | 11/2012 | Wu et al. |
| 2012/0282599 A1 | 11/2012 | Wu et al. |
| 2013/0059308 A1 | 3/2013 | Makarova et al. |
| 2013/0130930 A1 | 5/2013 | Parikh et al. |
| 2013/0144399 A1 | 6/2013 | Tai et al. |
| 2013/0164740 A1 | 6/2013 | Wu et al. |
| 2013/0344480 A1 | 12/2013 | Takagi |
| 2014/0080149 A1 | 3/2014 | Goehde |
| 2014/0154797 A1 | 6/2014 | Godfrin |

FOREIGN PATENT DOCUMENTS

| | | |
|---|---|---|
| CN | 1880473 | 12/2006 |
| CN | 101576557 | 11/2009 |
| CN | 101650370 | 2/2010 |
| CN | 102401761 | 4/2012 |
| WO | WO-92/22323 | 12/1992 |
| WO | WO-93/14776 | 8/1993 |
| WO | WO-94/16821 | 8/1994 |
| WO | WO-94/17011 | 8/1994 |
| WO | WO-94/17100 | 8/1994 |
| WO | WO-96/14578 | 5/1996 |
| WO | WO-96/27420 | 9/1996 |
| WO | WO-97/08557 | 3/1997 |
| WO | WO 97/35589 | * 10/1997 |

(56) References Cited

FOREIGN PATENT DOCUMENTS

| WO | WO-97/35589 | 10/1997 |
|---|---|---|
| WO | WO-99/41613 | 8/1999 |
| WO | WO-99/52640 | 10/1999 |
| WO | WO-99/62622 | 12/1999 |
| WO | WO-01/42502 | 6/2001 |
| WO | WO-02/12896 | 2/2002 |
| WO | WO-02/16647 | 2/2002 |
| WO | WO-02/27909 | 4/2002 |
| WO | WO-02/28523 | 4/2002 |
| WO | WO-02/29400 | 4/2002 |
| WO | WO-02/30562 | 4/2002 |
| WO | WO-02/31505 | 4/2002 |
| WO | WO-02/31506 | 4/2002 |
| WO | WO-02/077269 | 10/2002 |
| WO | WO-03/018757 | 3/2003 |
| WO | WO-03/031938 | 4/2003 |
| WO | WO-03/035894 | 6/2003 |
| WO | WO-03/065042 | 8/2003 |
| WO | WO-2004/011941 | 2/2004 |
| WO | WO-2004/076643 | 9/2004 |
| WO | WO-2005/028663 | 3/2005 |
| WO | WO-2006/041453 | 4/2006 |
| WO | WO-2006/116327 | 11/2006 |
| WO | WO-2009/097247 | 8/2009 |
| WO | WO-2010/085337 | 7/2010 |
| WO | WO-2010/135603 | 11/2010 |
| WO | WO-2011/139445 | 11/2011 |
| WO | WO-2011/150357 | 12/2011 |
| WO | WO-2013/078409 | 5/2013 |
| WO | WO-2013/088131 | 6/2013 |
| WO | WO-2013/181285 | 12/2013 |

OTHER PUBLICATIONS

Gazdar et al., J. Natl. Cancer Inst. (1999) 91:299-301.
Huang et al., Biochim. Biophys. Acta. (1996) 1282:76-84.
Huang et al., Biochim. Biophys. Acta. (1999) 1417:51-56.
Huang et al., J. Hematotherapy and Stem Cell Research (1999) 8:481-490.
Huang et al., J. Phys. D.: Appl. Phys. (1993) 26:1528-1535.
Huang et al., Phys. Med. Biol. (1992) 37:1499-1517.
Liakopoulos et al., Transducers 97, pp. 484-488, presented in 1997 International Conference on Solid State Sensors and Actuators, Chicago, Jun. 16, 1997.
Miller, Pediatric Cardiology (1999) 20(4):287-289.
Ogura et al., IEEE Trans. On Biomedical Engineering (1991) 38(8):721-726.
Pui et al., Biotachno. Prog. (1995) 11:146-152.
Safarik and Safarikova, J. of Chromatography (1999) 722(B):33-53.
Wang et al., Biophys. J. (1997) 72:1887-1899.
Wang et al., Biophysical Journal (1998) 74:2689-2701.
Wang et al., IEEE Transactions on Industry Applications (1997) 33(3):660-669.
Wu, J. Acoust. Soc. Am. (1991) 89:2140-2143.
Wu and Du, J. Acoust. Soc. Am. (1990) 87:997-1003.
Yang et al., Biophys. J. (1999) 76:3307-3314.
Yasuda et al., J. Acoust. Soc. Am. (1996) 99(2):1248-1251.
Yasuda et al., J. Acoust. Soc. Am. (1996) 99(4):1965-1970.
Yasuda et al., J. Acoust. Soc. Am. (1997) 102(1):642-645.
Yasuda and Kamakura, Appl. Phys. Lett. (1997) 71(13):1771-1773.
U.S. Appl. No. 10/268,312, filed Oct. 10, 2002.
Non-Final Office Action for U.S. Appl. No. 10/268,312, date mailed on Jun. 1, 2004.
Response to Office Action for U.S. Appl. No. 10/268,312, filed Sep. 1, 2004.
Response to Non-Compliant Amendment for U.S. Appl. No. 10/268,312, filed Feb. 1, 2005.
Notice of Allowance for U.S. Appl. No. 10/268,312, date mailed on Mar. 10, 2005.
Notice of Drawing Inconsistency with Specification for U.S. Appl. No. 10/268,312, date mailed on Jul. 28, 2005.
Response to Office Communication for U.S. Appl. No. 10/268,312, filed Aug. 9, 2005.
U.S. Appl. No. 10/701,684, filed Nov. 4, 2003.
Non-Final Office Action for U.S. Appl. No. 10/701,684, date mailed on Nov. 15, 2005.
Response to Office Action for U.S. Appl. No. 10/701,684, filed Jan. 13, 2006.
Notice of Allowance and Examiner's Amendment for U.S. Appl. No. 101701,684, dated Mar. 22, 2006.
Notice of Allowance for U.S. Appl. No. 10/701,684, date mailed on Aug. 10, 2006.
European Office Action for Application No. 02801051.0, date mailed on Sep. 15, 2006.
Response to European Office Action for Application No. 02801051.0, filed on Mar. 23, 2007.
European Office Action for Application No. 02801051.0, date mailed Apr. 26, 2007.
Response to European Office Action for Application No. 02801051.0, filed on Oct. 19, 2007.
European Office Action for Application No. 02801051.0, date mailed on Nov. 7, 2007.
Supplemental European Search Report for EP 04784274.5, mailed Aug. 7, 2008, 7 pages.
Abrams et al., Cancer Detect Prev. (1994) 18(1):65-78.
Adkins et al., J. Peds. Surg. (2004) 39:931-936.
Albelda et al., Journal of Cell Biology (1990) 110:1227-1237.
Allgayer et al., Journal of Histochemistry & Cytochemistry (1997) 45(2):203-212.
Berois et al., Anticancer Res. (1997) 17:2639-2646.
Bilkenroth et al., Int. J. Cancer (2001) 92:577-582.
Blanco et al., Oncogene (2002) 21(20):3241-3246.
Carlson et al., Am J. Clin Pathol. (2003) 120(Suppl):S101-S127.
Chiaramonte et al., J. Immunol. (1999) 162(2):920-930.
Choy et al., Br. J. Surg. (1993) 80(11):1490.
Cohn et al., Bone Marrow Transplant. (1997) 20(7):543-551.
Cooper et al., Laboratory Investigation (1985) 52(3):243-256.
Cote et al., J. Clinical Oncology (1991) 9(10):1749-1756.
Defougerolles and Springer, J. Exp. Med. (1992) 175:185-190.
Defougerolles et al., J. Exp. Med. (1993) 177:1187-1192.
Defougerolles et al., J. Exp. Med. (1994) 179:619-629.
Dhar et al., Lab Invest. (2003) 83(9):1343-1352.
Diala et al., J. Natl. Cancer Inst. (1983) 71(4):755-764.
El Hilali et al., Clin Cancer Res. (2005) 11(3):1253-1258.
Ellis et al., J. Urol. (1998) 159(4):1134-1138.
Faulkner et al., J. Hematother. (1998) 7(4):361-366.
Feldstein and Zelen, Breast Cancer Res Treat. (1984) 4(1):3-10.
Fidler, Cancer Research (1990) 50:6130-6138.
Franklin et al., Breast Cancer Res. Treat. (1996) 41(1):1-13.
Frost et al., Cancer Metastasis. Rev. (1983) 2(4):375-378.
Fuhr et al., Sensors and Materials (1995) 7:131-146.
Ghossein et al., 1996 ASCO Annual Meeting, abstract 647.
Glaves, Br. J. Cancer (1983) 48:665-673.
Gluck et al., Biol. Blood Marrow Transplant. (1997) 3(6):316-323.
Griwatz et al., Journal of Immunological Methods (1995) 183:251-265.
Gross et al., PNAS USA (1995) 92:537-541.
Haber et al., 1996 ASCO Annual Meeting, abstract 1442.
Hagedorn et al., Journal of Electrostatics (1994) 33:159-185.
Hamdy et al., Br. J. Urol. (1992) 69:392-396.
Hardingham et al., Cancer Research (1993) 53(15):3455-3458.
Hasegawa and Yosioka, J. Acoust. Soc. Am.(1969) 46:1139-1143.
Helfrich et al., British Journal of Cancer (1997) 76:29-35.
Iinuma et al., Int. J. Cancer (2000) 89:337-344.
Itoh et al., Clin Cancer Res. (2004) 10(8):2812-2817.
Johnson et al., British J. Cancer (1995) 72:268-276.
Juan et al., Allergy (1999) 54:1293-1298.
Juan et al., Eur. J. Immunol. (1993) 23:1508-1512.
Klickstein et al., Journal of Biological Chemistry (1996) 271(39):23920-23927.
Komeda et al., Cancer (1995) 75(9):2214-2219.
Kvalheim, Acta Oncologica (1996) 35(Supp. 8):13-18.
Larsson et al., Molecular Diagnosis (2001) 6:181-188.
Laver et al., Cancer Research Therapy and Control (1999) 9:25-30.

(56) References Cited

OTHER PUBLICATIONS

Leather et al., Br. J. Surg. (1993) 80(6):777-780.
Li et al., Neoplasia. (2005) 7(12):1073-1080.
Lindemann et al., Lancet (1992) 340(8821):685-9 (abstract only).
Louha et al., Hepatology (1997) 26(4):998-1005.
Makarovskiy et al., J. Clin. Lab. Anal. (1997) 11:346-350.
Mattano et al., Cancer Res. (1992) 52:4701-4705.
Matthay et al., J. Clin. Oncol. (1993) 11(11):2226-2233.
Naito et al., Eur. J. Cancer (1991) 27(6):762-765.
Mellado et al., Clin. Cancer Res. (1999) 5(7):1843-1848.
Molino et al., Cancer (1991) 67:1033-1036.
Mori et al., J. Clin. Oncol. (1998) 16:128-132.
Mortada et al., C.R. Acad. Sci. Paris (1990) t. 311, Serie III, p. 63-68.
Moss and Sanders, Journal of Clinical Oncology (1990) 8(4):736-740.
Moss et al., Program/Proceedings American Society of Clinical Oncology, Thirty-Third Annual Meeting May 17-20, 1997, vol. 16, p. 90a, abstract 317.
Moss et al., The New England Journal of Medicine (1991) 324(4):219-226.
Muirhead et al., Ann. NY Acad. Sci. (1986) 468:113-127.
Muller et al., Clin Cancer Res. (2005) 11(10):3678-3685.
Naito, Hokkaido Igaku Zasshi (1991) 66(2):135-141.
McHugh et al., Eur. J. Immunol. (2001) 31:2094-2103.
Nakamori et al., Dis. Colon Rectum (1997) 40(10):S29-S36.
Nuclepore track etched-membranes at http://www.whatman.com/products/?pageID=7.57.291.22, visited Dec. 13, 2005.
Pantel, Progress in Histochemistry and Cytochemistry (1996) 30(3):1-60.
Pecora et al., Biol. Blood Marrow Transplant. (2002) 8(10):536-543.
Pecora et al., Blood (1999) 94(Supp. 1):665a.
Perez et al., J. Immunol. (1989) 142:3662-3667.
Racila et al., PNAS USA (1998) 95:4589-4594.
Rao et al., J. Clin Invest. (2002) 110(3):351-360.
Rooney, "Nonlinear phenomena," in Methods of Experimental Physics: Ultrasonics, Edmonds (ed.) Academic Press (1981) Chapter 6.4 pp. 319-327.
Ross et al., Blood (1993) 82(9):2605-2610.
Salsbury, Cancer Treatment Reviews (1975) 2:55-72.
Sanders and Moss, Cancer (1991) 67:1423-1427.
Schlimok et al., Journal of Clinical Oncology (1990) 8:831-837 (abstract only).
Schwartzberg et al., Program/Proceedings American Society of Clinical Oncology, Thirty-Third Annual Meeting May 17-20, 1997, vol. 16, p. 118a, abstract 416.
Seeger et al., J. Clin. Oncol. (2000) 18(24):4067-4076.
Senie et al., Cancer (1994) 73(6):1666-1672.
Sewchand et al., Can. J. Physiol. Pharmacol. (1979) 57:1213-1222.
Simon et al., PNAS USA (1990) 78:2755-2759.
Smith et al., J. Clin. Oncol. (2000) 18(7):1432-1439.
Smith et al., Lancet (1991) 338(16):1227-1229.
Staunton et al., Cell (1990) 61:243-254.
Umiel et al., 1999 ASCO Annual Meeting, abstract 1215.
Umiel et al., Proc. Am. Soc. Clin. Oncol. (1999) 18:316a.
Vazeux et al., Nature (1992) 360:485-488.
Vilella et al., Tissue Antigens (1990) 36:203-210.
Villa et al., Gastroenterology (1996) 10:1346-1353.
Wakabayashi et al., Cancer (1995) 75(12):2827-2835.
Weber et al., Nature Genetics (2005) 37(8):853-862.
White et al., Proc. R. Soc. Med. (1976) 69:467-469.
Wisniewski et al., Leukemia Research (1991) 15(9):867-874.
Wong et al., J. Surgery (1995) 82:1333-1337.
Yang et al., J. Biol Chem. (2006) 281(14):9719-9727.
Yasuda et al., Jpn. J. Appl. Phys. (1996) 35:3295-3299.
Yosioka and Kawasima, Acustica (1955) 5:167-173.
International Search Report and Written Opinion for PCT/US07/16034, mailed Aug. 19, 2008, 5 pages.
Supplementary European Search Report for EP Application No. 07796848.5, mailed on Dec. 11, 2009, 8 pages.
U.S. Appl. No. 09/679,024, filed Oct. 4, 2000 (Xiaobo Wang).
Restriction Requirement from U.S. Appl. No. 11/777,962, mailed on Sep. 10, 2008.
Amendment in Response to Non-Final Office Action Restriction Requirement from U.S. Appl. No. 11/777,962, filed Oct. 6, 2008.
Non-Final Office Action from U.S. Appl. No. 11/777,962, mailed on Dec. 11, 2008.
Amendment in Response to Non-Final Office Action from U.S. Appl. No. 11/777,962, filed Apr. 13, 2009.
Non-Final Office Action from U.S. Appl. No. 11/777,962, mailed on Jul. 17, 2009.
Amendment in Response to Non-Final Office Action from U.S. Appl. No. 11/777,962, filed Jan. 19, 2010.
Interview Summary from U.S. Appl. No. 11/777,962, filed Feb. 1, 2010.
Non-Final Office Action from U.S. Appl. No. 11/777,962, mailed on Apr. 29, 2010.
Response to Notice to File Missing Parts of Nonprovisional Application and First Preliminary Amendment from U.S. Appl. No. 11/841,972, filed Feb. 11, 2008.
Response to Notice to File Missing Parts of Nonprovisional Application from U.S. Appl. No. 11/841,972, filed May 9, 2008.
Non-Final Office Action from U.S. Appl. No. 11/841,972, mailed on May 13, 2009.
Amendment in Response to Non-Final Office Action from U.S. Appl. No. 11/841,972, filed Oct. 12, 2009.
Non-Final Office Action from U.S. Appl. No. 11/841,972, mailed on Sep. 21, 2010.
Amendment in Response to Non-Final Office Action from U.S. Appl. No. 11/841,972, filed Mar. 21, 2011.
Office Action from EP Patent Application No. 09 012 086.6—2405, mailed on May 19, 2011, 4 pages.
Office Action for U.S. Appl. No. 11/841,972, mailed May 13, 2009.
Response to Office Action for U.S. Appl. No. 11/841,972, filed Oct. 12, 2009.
Office Action for U.S. Appl. No. 11/841,972, mailed Sep. 21, 2010.
Response to Office Action for U.S. Appl. No. 11/841,972, filed Mar. 21, 2011.
Notice of Allowance for U.S. Appl. No. 11/841,972, mailed Jul. 15, 2011.
Supplemental Notice of Allowance for U.S. Appl. No. 11/841,972, mailed Sep. 21, 2011.
Request for Continued Examination for U.S. Appl. No. 11/841,972, filed Oct. 14, 2011.
Office Action for CA 2,544,564, mailed Jan. 14, 2013.
Agouron Meeting Agenda, Jul. 13, 1998, 1 page.
Ancell Immunology Research Products, anti-human CD50 (ICAM-3), retrieved from http://www.ancell.com/html/anti-cd50_icam-3_.html, retrieved on Apr. 17, 2006.
BIS Laboratories, "Breast Carcinoma Assay" marketing piece (1996).
BIS' Biopharmaceutical Strategy—Surrogate Marker for Clinical Efficacy, Jul. 16, 1998, 2 pages.
Diab et al., "Bone Marrow and/or Peripheral Blood Micrometastases as Prognostic Factors in Breast Cancer Patients.", Protocol written in early 1998 or late 1987.
Documentation of Meeting with Sue Cohn, Oct. 19, 1996, 1 page.
ICAM3, retrieved from http://www.ihop-net.org/UniPub/iHOP/gs/89280.html, retrieved on Apr. 13, 2006.
ICAM3 antibody [101-1 D2] (ab23597) datasheet, retrieved from http://www.abcam.com/index.html?datasheet=23597, date retrieved Apr. 17, 2006.
Kletzel et al., J. Clin. Oncol. (2002) 20(9):2284-2292.
Moss, Letter from Thomas J. Moss, M.D. to Board of Directors; Ishage, Aug. 21, 1994, 2 pages.
Moss, Letter from Thomas J. Moss, M.D. To Morris Kletzel, M.D., Dec. 1, 1992, 1 page.
Moss, Letter from Thomas J. Moss, M.D. To Morris Kletzel, M.D., Jun. 11, 1993, 1 page.
Moss, Letter from Tom Moss to Charles Weaver, M.D., Nov. 4, 1996, 1 page.
Moss, Letter from Thomas J. Moss, M.D. To Victor M. Santana, M.D., Feb. 15, 1992, 2 pages.

(56) References Cited

OTHER PUBLICATIONS

Moss, Invitation to participate as a speaker at symposium from Thomas J. Moss, M.D. To J. Graham Sharp, Oct. 24, 1995, 2 pages.
Moss, Letter from Thomas J. Moss, M.D. To Susan Kreissman, M.D., Nov. 29, 1993, 1 page.
Moss, Meeting Report: 1st International Meeting on Minimal Residual Cancer, written Aug. 1996, following Jun. 1996 meeting, 2 pages.
Pantel and Moss, Meeting Report: 1st International Meeting on Minimal Residual Cancer, conference held Jun. 23-25, 1996.
Siegel, Letter from Marc D. Siegel to Herbert Lazarus, Ph.D., Sep. 20, 1995, 2 pages.
Supplementary Partial European Search Report for EP 02801051.0, mailed Jan. 19, 2006.
Communication pursuant to Article 96(2) EPC for EP 02801051.0, mailed May 15, 2006.
Response to Official Communication pursuant to Article 96(2) EPC for EP 02801051.0, filed Mar. 23, 2007.
Communication pursuant to Article 96(2) EPC for EP 02801051.0, mailed Sep. 15, 2006.
Response to Official Communication pursuant to Article 96(2) EPC for EP 02801051.0, filed May 19, 2008.
Communication pursuant to Article 96(2) EPC for EP 02801051.0, mailed Apr. 26, 2007.
Response to Official Communication pursuant to Article 96(2) EPC for EP 02801051.0, filed Jul. 25, 2006.
Communication pursuant to Article 96(2) EPC for EP 02801051.0, mailed Nov. 7, 2007.
Response to Official Communication pursuant to Article 96(2) EPC for EP 02801051.0, filed Oct. 19, 2007.
Communication pursuant to Article 94(3) EPC for EP 02801051.0, mailed Jun. 24, 2008.
Response to Official Communication pursuant to Article 94(3) EPC for EP 02801051.0, filed Dec. 29, 2008.
Decision to Grant Patent for EP 02801051.0, mailed Aug. 5, 2010.
Communication pursuant to Article 94(3) EPC for EP 04784274.5, mailed Mar. 24, 2009.
Communication pursuant to Article 94(3) EPC for EP 04784274.5, mailed Jan. 13, 2010.
Response to Communication for EP 04784274.5, filed Jul. 16, 2010.
Communication pursuant to Article 94(3) EPC for EP 04784274.5, mailed Nov. 29, 2011.
Response to Communication for EP 04784274.5, filed Jun. 1, 2012.
Office Action for CA 2,544,564, mailed Jun. 3, 2011.
Response to Examiner's Report for CA 2,544,564, filed Dec. 5, 2011.
Office Action for CA 2, 544,564, mailed Jan. 14, 2013.
Office Action for CA 2,462,914, mailed Jul. 7, 2011.
Response to Examiner's Report for CA 2,462,914, filed Jan. 9, 2012.
Response to Final Office Action for U.S. Appl. No. 11/264,413, filed Feb. 12, 2010.
Response to Non-Final Office Action for U.S. Appl. No. 11/264,413, filed Dec. 13, 2010.
Final Office Action for U.S. Appl. No. 11/264,413, mailed Dec. 10, 2009.
Office Action for U.S. Appl. No. 11/264,413, mailed Mar. 6, 2009.
Office Action for U.S. Appl. No. 11/264,413, mailed Jun. 11, 2010.
Response to Non-Final Office Action for U.S. Appl. No. 11/264,413, filed Jul. 30, 2009.
Restriction Requirement for U.S. Appl. No. 11/264,413, mailed Dec. 13, 2007.
Response to Restriction Requirement for U.S. Appl. No. 11/264,413, filed Jan. 10, 2008.
Notice of Allowance for U.S. Appl. No. 11/841,972, mailed May 30, 2013, 6 pages.
Notice of Allowance for U.S. Appl. No. 11/264,413, mailed Jun. 3, 2013, 6 pages.
Communication pursuant to Article 94(3) EPC, mailed Jul. 8, 2013, 6 pages.
Supplementary Partial European Search Report for EP 02 72 8540, mailed on Apr. 4, 2005, 7 pages.

Notice of Reasons for Rejection for Japanese Patent Application No. 2005-310561, mailed on Jul. 6, 2009, 3 pages.
Office Action for Japanese Patent Application No. 2002-575311, mailed on Oct. 4, 2007.
Office Action for U.S. Appl. No. 10/103,581, mailed Aug. 18, 2004.
Response to Office Action for U.S. Appl. No. 10/103,581, mailed Dec. 20, 2004.
Final Office Action for U.S. Appl. No. 10/103,581, mailed Mar. 22, 2005.
Response after Final Office Action for U.S. Appl. No. 10/103,581, mailed Jun. 27, 2005.
Advisory Action for U.S. Appl. No. 10/103,581, mailed Jul. 14, 2005.
Office Action for U.S. Appl. No. 10/103,581, mailed Sep. 29, 2005.
Response to Office Action for U.S. Appl. No. 10/103,581, mailed Dec. 29, 2005.
Notice of Allowance and Examiner Interview Summary for U.S. Appl. No. 10/103,581, mailed Mar. 20, 2006.
RCE and Amendment for U.S. Appl. No. 10/103,581, mailed Jun. 20, 2006.
Notice of Allowance and Examiner's Amendment for U.S. Appl. No. 10/103,581, mailed Jul. 25, 2006.
Supplemental Notice of Allowance for Examiner's Amendment for U.S. Appl. No. 10/103,581, mailed Oct. 17, 2006.
Substance of Interview for U.S. Appl. No. 10/103,581, mailed Nov. 17, 2006.
Examiner Interview Summary for U.S. Appl. No. 11/598,848, mailed Jan. 27, 2010.
Office Action for U.S. Appl. No. 11/598,848, mailed Feb. 5, 2010.
Substance of Interview for U.S. Appl. No. 11/598,848, mailed Feb. 23, 2010.
Response to Office Action for U.S. Appl. No. 11/598,848, mailed Jul. 6, 2010.
Final Office Action for U.S. Appl. No. 11/598,848, mailed Oct. 14, 2010.
Response after Final Office Action for U.S. Appl. No. 11/598,848, mailed Dec. 13, 2010.
Notice of Allowance for U.S. Appl. No. 11/598,848, mailed Dec. 27, 2010.
International Preliminary Examination Report for International Patent Application No. PCT/US02/08880, mailed Jun. 25, 2003.
Becker et al., "Separation of Human Breast Cancer Cells from Blood by Differential Dielectric Affinity," Proc. Natl. Acad. Sci. USA (1995) 29:860-864.
Bianchi et al., "Isolation of Fetal DNA from Nucleated Erythrocytes in Maternala Blood," Proc. Natl. Sci. USA (1990) 86:3279-3283.
Chan et al., "Measurements of the Dielectric Properties of Peripheral Blood Mononuclear Cells and Trophoblast Cells using AC Electrokinetic Techniques," Biochimica et Biophysica Acta (2000) 1500(3):313-322.
Cheng et al., "Isolation of Cultured Cervical Carcinoma Cells Mixed with Peripheral Blood Cells on a Bioelectronic Chip," Anal. Chem. (1998) 70(11):2321-2326.
Cheng et al., "Preparation and Hybridization Analysis of DNA/RNA fom *E. coli* on Microfabricated Bioelectronic Chips," Nature Biotechnology (1998) 16(6):541-546.
Cheung et al., "Prenatal Diagnosis of Sickle Cell Anaemia and Thalassaemia by Analysis of Fetal Cells in Maternal Blood," Nature Genetics (1996) 14:264-268.
Fuhr et al., "Positioning and Manipulation of Cells and Microparticles Using Miniaturized Electric Field Traps and Travelling Waves," Sensors and Materials (1995) 7:131-146.
Holzgreve et al., "Fetal Cells in the Maternal Circulation," Journal of Reproductive Medicine (1992) 37(5):410-418.
Huang et al., "Membrane Changes Associated with the Temperature-Sensitive P85$^{gag\text{-}mos}$ dependent Transformation of Rat Kidney Cells as Determined by Dielectrophoresis and Electrorotation," Biochem. Biophys. Acta (1996) 1282:76-84.
Huang et al., "Introducing Dielectrophoresis as a New Force Field for Field-Flow Fractionation," Biophysical Journal (1997) 73:1118-1129.
Huang et al., "Electrokinetic Behaviour of Colloidal Particles in Travelling Electric Fields: Studies Using Yeast Cells," J. Phys. D. Appl. Phys. (1993) 26:1528-1535.

(56) References Cited

OTHER PUBLICATIONS

Hughes et al., "Dielectophoretic Forces on Particles in Travelling Electric Fields," J. Phys. Appl. Phys. (1997) 29:474-482.
Kuo and Guo, "Nucleated Red Blood Cells in Maternal Blood During Pregnancy," Obstetrics and Gynecology (1999) 94(3): 464-468.
Markz et al., "Seperation of Viable and Non-viable Yeast Using Dielectrophoresis," Journal of Biotechnology (1994) 32:29-37.
Mavrou et al., "Fetal Cells in Maternal Blood: Isolation by Magnetic Cell Sorting and Confirmation by Immunophenotyping and FISH," In Vivo (1998) 12(2):195-200.
Merriam-Webster Online Dictionary, (2004) www.m-w.com, accessed Jul. 28, 2004.
Miale, "Laboratory Medicine: Hematology," (1972) C.V. Mosby Company, $4^{th}$ Ed., pp. 1208-120.9.
Muller, "A 3-D Microelectrode System for Handling and Caging Single Cells and Particles," Biosensors & Bioelectronics (1999) 14:247-256.
Pethig, "Dielectrophoresis: Using Inhomogeneous AC Electrical Fields to Seperate and Manipulate Cells," Critical Reviews in Biotechnology (1996) 16(4):331-348.
Shafer et al., "Preperation of Interpretation of Peripheral Blood Smears," Hematology: Basic Principles and Practice, (1995) Churchhill Livingstone, Hoffman et al. (eds.), $2^{nd}$ Ed., pp. 2202-2209.
Simpson and Elias, "Isolating Fetal Cells in Maternal Circulation for Prenatal Diagnosis," Prenatal Diagnosis (1994) 14:1229-1242.
Talary et al., "Electromanipulation and Seperation of Cells Using Travelling Eletric Fields," J. Phys. D: Appl. Phys. (1996) 29:2198-2203.
Wang et al., "Non-uniform Spatial Distributions of Both the Magnitude and Phase of AC Electric Fields Determine Dielectrophoretic Forces," Biochem. Biophys. Acta (1995) 1243:185-194.
Wang et al., "Dielectrophoretic Manipulation of Cells with Spiral Electrodes," Biophys. J. (1997) 72:1887-1899.
Wang et al., "A Unified Theory of Dielectrophoresis and Travelling Wave Dielectrophoresis," J. Phys. D. Appl. Phys. (1994) 27:1571-1574.
Williamson, "Towards Non-invasive Prenatal Diagnosis," Nature Gentics (1996) 14:239-240.
Adams et al., "Rapid and Efficient Isolation of Circulating Tumor Cells from Whole Blood Using High Porosity Precision Microfilters," Creatv MicroTech, Inc., presented at 7th Early Detection Research Network (EDRN) Scientific Workshop, Herndon, VA, Sep. 13-16, 2011, 1 page.
Chen et al., "Microfluidic Chip for Blood Cell Separation and Collection Based on Crossflow Filtration," Sensors and Actuators B 130 (2008) 216-221.
Lu et al., "Parylene Membrane Slot Filter for the Capture, Analysis and Culture of Viable Circulating Tumor Cells," California Institute of Technology, downloaded on Jul. 12, 2010 from IEEE Xplore, pp. 935-938.
Office Action for Taiwanese Patent Application No. 091105474, dated May 14, 2004.
Response to Office Action for Taiwanese Patent Application No. 091105474, dated Oct. 21, 2004.
Office Action for Taiwanese Patent Application No. 091105474, dated Sep. 27, 2009.
Response to Office Action for Taiwanese Patent Application No. 091105474, dated Dec. 1, 2009.
Office Action for Australian Patent Application No. 2007205731, dated Oct. 30, 2007.
Response to Office Action for Australian Patent Application No. 2007205731, dated Nov. 14, 2007.
Office Action for Australian Patent Application No. 2007205731, dated Nov. 26, 2007.
Response to Office Action for Australian Patent Application No. 2007205731, dated Sep. 11, 2008.
Acceptance for Australian Patent Application No. 2007205731, dated Sep. 18, 2008.
Office Action for Canadian Patent Application No. 2,440,385, dated Dec. 1, 2009.
Response to Office Action for Canadian Patent Application No. 2,440,385, dated Jun. 1, 2010.
Office Action for Canadian Patent Application No. 2,440,385, dated Dec. 15, 2010.
Response to Office Action for Canadian Patent Application No. 2,440,385, dated Jun. 15, 2011.
Communication for European Patent Application No. 02728540.2, dated May 22, 2006.
Response to Communication for European Patent Application No. 02728540.2, dated Sep. 25, 2006.
Communication for European Patent Application No. 02728540.2, dated Apr. 12, 2007.
Response to Communication for European Patent Application No. 02728450.2, dated Aug. 20, 2007.
Communication for European Patent Application No. 02728540.2, dated Dec. 18, 2008.
Response to Communication for European Patent Application No. 02728540.2 dated, Apr. 28, 2009.
Communication for European Patent Application No. 02728540.2, dated Oct. 28, 2009.
Reply to Communication for European Patent Application No. 02728540.2, dated Mar. 5, 2010.
Decision to Grant for European Patent Application No. 02728540.2, dated Apr. 1, 2010.
Office Action for Japanese Patent Application No. 2002-575311, dated Apr. 26, 2005.
Response to Office Action for Japanese Patent Application No. 2002-575311, dated Oct. 25, 2005.
Final Office Action for Japanese Patent Application No. 2002-575311, dated Oct. 2, 2007.
Office Action for Japanese Patent Application No. 2005-310561, dated Sep. 29, 2008.
Response to Office Action for Japanese Patent Application No. 2005-310561, dated Dec. 26, 2008.
Office Action for Japanese Patent Application No. 2005-310561, dated Jul. 2, 2009.
Response to Office Action for Japanese Patent Application No. 2005-310561, dated Oct. 5, 2009.
Notice of Allowance for Japanese Patent Application No. 2005-310561, dated Oct. 27, 2009.
Office Action for Australian Patent Application No. 2002258585, dated Apr. 21, 2006.
Response to Office Action for Australian Patent Application No. 2002258585 dated Apr. 16, 2007.
Notice of Acceptance for Australian Patent Application No. 2002258585 dated Apr. 24, 2007.
Partial Search Report for European Patent Application No. 09007354.5, dated Sep. 3, 2009.
Extended Search Report for European Patent Application No. 09007354.5, dated Dec. 22, 2009.
Communication for European Patent Application No. 09007354.5, dated Apr. 6, 2010.
Response to Communication for European Patent Application No. 09007354.5, dated Aug. 16, 2010.
Communcation for European Patent Application No. 09007354.5, dated Aug. 2, 2011.
Response to Communication for European Patent Application No. 09007354.5, dated Dec. 12, 2011.
Communication for European Patent Application No. 09007354.5, dated Dec. 14, 2012.
Response to Communication for European Patent Application No. 09007354.5, dated May 21, 2013.
Letter Accompanying Subsequently Filed Items for European Patent Application No. 09007354.5, dated Jun. 7, 2013.
Result of Consultation for European Patent Application No. 09007354.5, dated Jun. 18, 2013.
Communication of Intent to Grant for European Patent Application No. 09007354.5, dated Jun. 28, 2013.
Office Action for CA 2,462,914, mailed Dec. 9, 2013, 3 pages.
Office Action for U.S. Appl. No. 14/027,044, mailed Jan. 9, 2014, 4 pages.
Office Action for U.S. Appl. No. 14/029,598, mailed Jan. 10, 2014, 6 pages.

(56) References Cited

OTHER PUBLICATIONS

Response to Communication pursuant to Article 94(3) EPC, filed Jan. 17, 2014, 126 pages.
Request for Continued Examination for U.S. Appl. No. 11/264,413, filed Oct. 2, 2013, 15 pages.
Notice of Allowance for U.S. Appl. No. 11/264,413, mailed Oct. 22, 2013, 7 pages.
Request for Continued Examination for U.S. Appl. No. 11/841,972, filed Oct. 24, 2013, 1 page.
Notice of Allowance for U.S. Appl. No. 11/841,972, mailed Nov. 4, 2013, 7 pages.
Request for Continued Examination for U.S. Appl. No. 11/264,413, filed Jan. 22, 2014, 3 pages.
Request for Continued Examination for U.S. Appl. No. 11/841,972, filed Feb. 4, 2014, 3 pages.
Notice of Allowance for U.S. Appl. No. 11/264,413, mailed Feb. 14, 2014, 5 pages.
Response to Office Action for U.S. Appl. No. 14/027,044, mailed Jun. 9, 2014, 7 pages.
Response to Examination Report for CA 2,462,914, filed Jun. 9, 2014, 20 pages.
Response to Office Action for U.S. Appl. No. 11/841,972, filed Jun. 11, 2014, 6 pages.
Aversa et al., "A Monoclonal Antibody (A6) Recognizing a Unique Epitope Restricted to CD45RO and RB Isoforms of the Leukocyte Common Antigen Family Identifies Functional T Cell Subsets," Cellular Immunology (1994) 158:314-328.
Cytelligen Trademark, registration No. 4436018, registered Nov. 19, 2013.
Dahlke et al., "In vivo depletion of hematopoietic stem cells in the rat by an anti-CD45 (RT7) antibody," Blood (2002) 99(10): 12 pages.
iFISH Trademark, registration No. 4494597, registered Mar. 11, 2014.
Lara et al., "Enrichment of rare cancer cells through depletion of normal cells using density and flow-through, immunomagnetic cell separation," Experimental Hematology (2004) 32:891-904.
Lin et al., "Calnuc plays a role in dynamic distribution of Gαi but not Gβ subunits and modulates ACTH secretion in AtT-20 neuroendocrine secretory cells," Molecular Neurodegeneration (2009) 4:15, 16 pages.
New Products, Science Magazine (Jul. 26, 2013) 341(6144):415, 2 pages.
Ran et al., "Determination of EGFR mutations in single cells microdissected from enriched lung tumor cells in peripheral blood," Analytical and Bioanalytical Chemistry (2013) 405(23):7377-7382 (Abstract).
Scott et al., "Effect of Osmotic Lysis and Resealing on Red Cell Structure and Function," The Journal of Laboratory and Clinical Medicine (1990) 115(4):470-480.
Tanaka et al., "Circulating tumor cells (CTCs) in lung cancer: current status and future perspectives," Lung Cancer: Targets and Therapy (2010) 1:77-84.
Vona et al., "Technical Advance: Isolation by Size of Epithelial Tumor Cells," American Journal of Pathology (2000) 156(1):57-63.
Wu et al., "Preliminary Investigation of the Clinical Significance of Detecting Circulating Tumor Cells Enriched from Lung Cancer Patients," Journal of Thoracic Oncology (2009) 4(1):30-36.
Xing and Wang, "Clinical Validation of an Enrichment and Identification Method of Circulating Tumor Cells in Breast Cancer Patients," Science & Technology Review (2012) 30(21):56-60 (English abstract included).
Notice of Allowance for U.S. Appl. No. 14/027,044, mailed Jul. 2, 2014, 6 pages.
Notice of Allowance for U.S. Appl. No. 11/841,972, mailed Jul. 8, 2014, 5 pages.
Request for Reinstatement and Response to Examiner's Report for CA 2,544,564, filed Jul. 14, 214, 66 pages.
Notice of Allowance for U.S. Appl. No. 11/264,413, mailed Jul. 18, 2014, 5 pages.

\* cited by examiner

METHODS AND COMPOSITIONS FOR SEPARATING RARE CELLS FROM FLUID SAMPLES

CROSS-REFERENCE TO RELATED APPLICATIONS

This application claims benefit of priority to U.S. patent application Ser. No. 60/704,601 entitled, "Improved Methods and Compositions for Separating Rare Cells From Fluid Samples," filed Aug. 2, 2005 and is herein incorporated by reference in its entirety. This application is also a continuation-in-part of U.S. patent application Ser. No. 10/701,684, entitled "Methods, Compositions, and Automated Systems for Separating Rare Cells from Fluid Samples" filed Nov. 4, 2003 now U.S. Pat. No. 7,166,443, which is a continuation-in-part of U.S. patent application Ser. No. 10/268,312, entitled "Methods, Compositions, and Automated Systems for Separating Rare Cells from Fluid Samples" filed Oct. 10, 2002 now U.S. Pat. No. 6,949,355 which claims benefit of priority to U.S. Provisional Patent application Ser. No. 60/348,228, filed on Oct. 29, 2001, entitled "Methods and automated systems for separating rare cells from fluid samples" and United Sates Provisional Patent application No. 60/328,724, filed Oct. 11, 2001, entitled "Methods and automated systems for separating rare cells from fluid samples", and U.S. Provisional Patent application No. 60/394,517, filed on Jul. 9, 2002, entitled "Methods and automated systems for separating rare cells from fluid samples", all of which are incorporated by reference herein in their entirety.

BACKGROUND OF THE INVENTION

The present invention relates generally to the field of bio-separation, and in particular to the field of biological sample processing.

Sample preparation is a necessary step for many genetic, biochemical, and biological analyses of biological and environmental samples. Sample preparation frequently requires the separation of sample components of interest from the remaining components of the sample. Such separations are often labor intensive and difficult to automate.

In many cases it is necessary to analyze relatively rare components of a sample. In this case, it may be necessary both to increase the concentration of the rare components to be analyzed, and to remove undesirable components of the sample that can interfere with the analysis of the components of interest. Thus, a sample must be "debulked" to reduce its volume, and in addition subjected to separation techniques that can enrich the components of interest. This is particularly true of biological samples, such as ascites fluid, lymph fluid, or blood, that can be harvested in large amounts, but that can contain minute percentages of target cells (such as virus-infected cells, anti-tumor T-cells, inflammatory cells, cancer cells, or fetal cells) whose separation is of critical importance for understanding the basis of disease states as well as for diagnosis and development of therapies.

Filtration has been used as a method of reducing the volume of samples and separating sample components based on their ability to flow through or be retained by the filter. Typically membrane filters are used in such applications in which the membrane filters have interconnected, fiber-like, structure distribution and the pores in the membrane are not discretely isolated; instead the pores are of irregular shapes and are connected to each other within the membrane. The so-called "pore" size really depends on the random tortuosity of the fluid-flow patches (e.g. pores) in the membrane. While the membrane filters can be used for a number of separation applications, the variation in the pore size and the irregular shapes of the pores prevent them being used for precise filtration based on particle size and other properties.

Microfabricated filters have been made for certain cellular or molecular separation. These microfabricated structures do not have pores, but rather include channels that are microetched into one or more chips, by using "bricks" (see, for example, U.S. Pat. No. 5,837,115 issued Nov. 17, 1998 to Austin et al., incorporated by reference) or dams see, for example, U.S. Pat. No. 5,726,026 issued Mar. 10, 1998 to Wilding et al., incorporated by reference) that are built onto the surface of a chip. While these microfabricated filters have precise geometries, their limitations are that the filtration area of the filter is small, limited by the geometries of these filters, so that these filters can process only small volumes of the fluid sample.

Blood samples provide special challenges for sample preparation and analysis. Blood samples are easily obtained from subjects, and can provide a wealth of metabolic, diagnostic, prognostic, and genetic information. However, the great abundance of non-nucleated red blood cells, and their major component hemoglobin, can be an impediment to genetic, metabolic, and diagnostic tests. The debulking of red blood cells from peripheral blood has been accomplished using different layers of dense solutions (for example, see U.S. Pat. No. 5,437,987 issued Aug. 1, 1995 to Teng, Nelson N. H. et al). Long chain polymers such as dextran have been used to induce the aggregation of red blood cells resulting in the formation of long red blood cell chains (Sewchand L S, Canham P B. (1979) 'Modes of rouleaux formation of human red blood cells in polyvinylpyrrolidone and dextran solutions' Can. J. Physiol. Pharmacol. 57(11):1213-22. However, the efficiency of these solutions in removing red blood cells is less than optimal, especially where the separation or enrichment of rare cells, such as, for example, fetal cells from maternal blood or cancer cells from a patient, is desirable.

Exfoliated cells in body fluids (e.g. sputum, urine, or even ascetic fluid or other effusions) present a significant opportunity for detection of precancerous lesions and for eradication of cancer at early stages of neoplastic development. For example, urine cytology is universally accepted as the non-invasive test for the diagnosis and surveillance of transitional cell carcinoma (Larsson et al. (2001) Molecular Diagnosis 6: 181-188). However, in many cases, the cytologic identification of abnormal exfoliated cells has been limited by the number of abnormal cells isolated. For routine urine cytology (Ahrendt et al. (1999) J. Natl. Cancer Inst. 91: 299-301), the overall sensitivity is less than 50%, which varies with tumor grade, tumor stage, and urine collection and processing methods used. Molecular analysis (e.g. using in situ hybridization, PCR, microarrays, etc) of abnormal exfoliated cells in body fluids based on molecular and genetic biomarkers can significantly improve the cytology sensitivity. Both biomarker studies and use of biomarkers for clinical practice would require a relative pure exfoliated cell population enriched from body fluids comprising not only exfoliated cells but also normal cells, bacteria, body fluids, body proteins and other cell debris. Thus, there is an immediate need for developing an effective enrichment method for enriching and isolating exfoliated abnormal cells from body fluids.

Current approaches for enriching and preparing exfoliated cells from body fluids are through media based separation, antibody capture, centrifugation and membrane filtration. While these techniques are simple and straightforward, they suffer from a number of limitations, including: inadequate efficiency for rare cell enrichment; low sensitivity of rare cell detection; difficulty in handling large volume samples; inconsistency of the enrichment performance; and labor-intensiveness of separation procedure.

There is a need to provide methods of sample preparation that are efficient and automatable that can process relatively large sample volumes, such as large volumes of biological fluid samples, and separate target cells. The present invention provides these and other benefits.

BRIEF SUMMARY OF THE INVENTION

The present invention recognizes that diagnosis, prognosis, and treatment of many conditions can depend on the enrichment of rare cells from a complex fluid sample. Often, enrichment can be accomplished by one or more separation steps. In particular, the separation of fetal cells from maternal blood samples, can greatly aid in the detection of fetal abnormalities or a variety of genetic conditions. In addition, the present invention recognizes that the enrichment or separation of rare malignant cells from patient samples, such as the isolation of cancerous cells from patient body fluid samples, can aid in the detection and typing of such malignant cells and therefore aid in diagnosis and prognosis, as well as in the development of therapeutic modalities for patients.

A first aspect of the present invention are methods of enriching rare cells from a peripheral blood sample in which during washing of a blood sample, the blood sample is centrifuged at a speed that enhances the recovery of a rare cell type of interest. In one embodiment of this aspect, a blood sample (obtained from a pregnant female) is washed by centrifuging at a speed that enhances recovery of mononucleated fetal cells. In another embodiment of this aspect, a maternal blood sample is washed by centrifuging at a speed that enhances recovery of fetal polynucleated or less healthy fetal cells (e.g. trophoblasts, apoptotic or dying cells).

In a related aspect of the present invention, methods of enriching rare cells from a maternal blood sample are provided in which recovery of a rare cell type of interest is enhanced by use of a maternal blood sample of a particular gestational age or window. In one embodiment of this aspect, a maternal blood sample of a particular gestational age or window is harvested for enrichment of nucleated fetal cells. In another embodiment of this aspect, a maternal blood sample of a particular gestational age or window is harvested for enrichment of fetal trophoblasts or nucleated red blood cells.

A third aspect of the present invention are methods of isolating rare fetal cells from a maternal blood sample comprising: providing a maternal blood sample; washing the maternal supernatant twice by centrifugation, in which after the second wash centrifugation a second wash supernatant and a second wash pellet are obtained; resuspending the second wash pellet to obtain second wash pellet cells; resuspending the second wash pellet cells; centrifuging the second wash supernatant to obtain pelleted second wash supernatant cells; resuspending the pelleted second wash supernatant cells and adding the second wash supernatant cells to the resuspended second wash pellet cells to obtain combined second wash pellet and second wash supernatant cells; and enriching rare cells from the combined second wash pellet and second wash supernatant cells. The enriching procedure can include any combination of: debulking the sample, removing one or more undesirable components from the sample, and separating one or more desirable components of the sample.

A fourth aspect of the present invention is the use of an antibody or molecule that specifically binds a platelet surface molecule or moiety or serum protein(s) with lesser binding to the desired cells. Nonlimiting examples include an antibody or molecule that binds CD31, CD36, CD41, CD42 (a, b, c), CD51 and CD51/61. The antibody may be utilized to remove platelets from a blood sample. The antibody can optionally be bound to a solid support. In preferred embodiments of the present invention, the antibody can be used to remove platelets from a blood sample in a procedure for enriching rare cells from a blood sample.

A fifth aspect of the present invention is a magnet configuration for efficient separation of magnetic particles from a sample. In preferred embodiments, the magnet configuration comprises multiple magnets positioned around a vessel such as a tube. The present invention also includes methods of separating sample components from a fluid sample using magnetic particles and a magnet configuration comprising multiple magnets positioned around the sample vessel.

A sixth aspect of the present invention is a method of making a microfabricated filter that comprises at least one pore for filtering a fluid sample. The method may include providing a chip, depositing a dielectric layer along opposing surfaces of a portion of the chip, removing at least one region of the dielectric layer and at least one region of the chip that is to become at least one pore and removing the remaining dielectric layer. The method may also include forming a cavity prior to forming the at least one pore and forming the at least one pore in substantial alignment with cavity. The present invention also includes filters made using the methods of the present invention.

The present invention also comprises methods of treating or modifying (e.g. chemically) a filter of the present invention to increase the efficiency of filtering a fluid sample, such as a fluid sample that comprises cells. The present invention also includes filters treated using the methods of the present invention.

A seventh aspect of the present invention is a method for enriching rare cells from a blood sample that comprises: debulking the blood sample; specifically labeling at least one component of the blood sample with a detectable label; and separating one or more components of the sample utilizing components other than the at least one component of the sample that is labeled with a detectable label. The one or more components of the blood sample labeled with a detectable label are preferably desirable components of the sample, but can also be undesirable components of the sample, or both desirable and undesirable components of the sample.

In some preferred embodiments, a blood sample is debulked by adding a solution that selectively sediments red blood cells, and a labeling reagent that labels desirable cells is added to the blood sample at the same time as the debulking solution. Preferably, specific binding members that bind undesirable sample components are also added with the debulking solution.

In some preferred embodiments, after debulking and the removal of undesirable components from the blood sample, labeled desirable cells are further enriched or isolated using fluorescence activated cell sorting or laser cytometry. In some preferred embodiments, after debulking and the removal of undesirable components from the blood sample, labeled desirable cells are further analyzed using spectral imaging, fluorescence microscopy, visible light microscopy, or manual or automated image analysis.

An eighth aspect of the present invention is a method of enriching a rare cell, such as a cancer cell, from a biological sample including performing at least one debulking step on a blood sample and selectively removing at least one type of undesirable component from the blood sample to enrich a rare cell of interest in the blood sample. Selective removal may occur by contacting the blood sample with one or more specific binding members that are specific to one or more types of undesirable components, the specific binding members being optionally coupled to a solid support such as a microbead or magnetic bead. Examples of suitable specific binding members are antibodies or antibody fragments such as those capable of binding CD3, CD11b, CD14, CD17, CD31, CD36, CD41, CD42 (a, b, c), CD45, CD50, CD51, CD51/61, CD53, CD63, CD69, CD81, CD84, CD102 or CD166. White-blood cells are one type of undesirable component. Debulking, such as removing red blood cells, may be performed using non-limiting methods such as sedimentation, lysis, centrifugation and the like. Rare cells, such a cancer cells or other non-hematopietic cells may be labeled and/or further isolated.

BRIEF DESCRIPTION OF THE FIGURES

FIG. 25A shows a control sample and FIG. 25B shows a sample treated with a biotinylated CD31 antibody used in combination with neutravidin coated magnetic beads.

DETAILED DESCRIPTION OF THE INVENTION

Definitions

Figure 1:
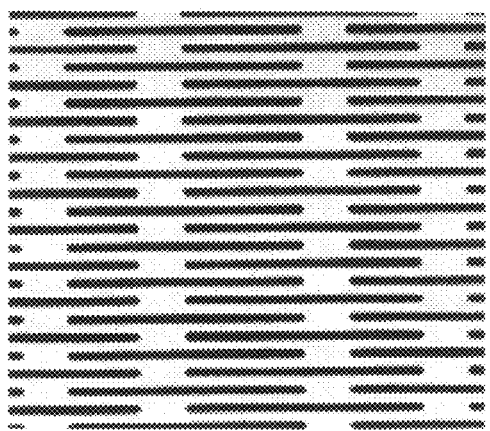
FIG. 1 is the top view of a region of a microfabricated chip of the present invention. The dark areas are the precision manufactured slots in the filter that has a filtration area of 1 cm$^2$.

Unless defined otherwise, all technical and scientific terms used herein have the same meaning as commonly understood by one of ordinary skill in the art to which this invention belongs. Generally, the nomenclature used herein and the manufacture procedures for devices and components as well as the laboratory procedures described below are well known and commonly employed in the art. Conventional methods are used for these procedures, such as those provided in the art and various general references. Where a term is provided in the singular, the inventors also contemplate the plural of that term. As employed throughout the disclosure, the following terms, unless otherwise indicated, shall be understood to have the following meanings:

A "component" of a sample or "sample component" is any constituent of a sample, and can be an ion, molecule, compound, molecular complex, organelle, virus, cell, aggregate, or particle of any type, including colloids, aggregates, particulates, crystals, minerals, etc. A component of a sample can be soluble or insoluble in the sample media or a provided sample buffer or sample solution. A component of a sample can be in gaseous, liquid, or solid form. A component of a sample may be a moiety or may not be a moiety.

A "moiety" or "moiety of interest" is any entity whose manipulation is desirable. A moiety can be a solid, including a suspended solid, or can be in soluble form. A moiety can be a molecule. Molecules that can be manipulated include, but are not limited to, inorganic molecules, including ions and inorganic compounds, or can be organic molecules, including amino acids, peptides, proteins, glycoproteins, lipoproteins, glycolipoproteins, lipids, fats, sterols, sugars, carbohydrates, nucleic acid molecules, small organic molecules, or complex organic molecules. A moiety can also be a molecular complex, can be an organelle, can be one or more cells, including prokaryotic and eukaryotic cells, or can be one or more etiological agents, including viruses, parasites, or prions, or portions thereof. A moiety can also be a crystal, mineral, colloid, fragment, mycelle, droplet, bubble, or the like, and can comprise one or more inorganic materials such as polymeric materials, metals, minerals, glass, ceramics, and the like. Moieties can also be aggregates of molecules, complexes, cells, organelles, viruses, etiological agents, crystals, colloids, or fragments. Cells can be any cells, including prokaryotic and eukaryotic cells. Eukaryotic cells can be of any type. Of particular interest are cells such as, but not limited to, white blood cells, malignant cells, stem cells, progenitor cells, fetal cells, and cells infected with an etiological agent, and bacterial cells. Moieties can also be artificial particles such polystyrene microbeads, microbeads of other polymer compositions, magnetic microbeads, and carbon microbeads.

As used herein, "manipulation" refers to moving or processing of the moieties, which results in one-, two- or three-dimensional movement of the moiety, whether within a single chamber or on a single chip, or between or among multiple chips and/or chambers. Moieties that are manipulated by the methods of the present invention can optionally be coupled to binding partners, such as microparticles or microbeads. Non-limiting examples of the manipulations include transportation, capture, focusing, enrichment, concentration, aggregation, trapping, repulsion, levitation, separation, isolation or linear or other directed motion of the moieties, detection, identification, characterization, culturing and the like. For effective manipulation of moieties coupled to binding partners, the binding partner and the physical force used in the method must be compatible. For example, binding partners with magnetic properties may be used with magnetic force. Thus, magnetic microbeads may be used in a magnetic field to manipulate a moiety. Similarly, binding partners with certain dielectric properties, e.g., plastic particles, polystyrene microbeads, must be used with dielectrophoretic force.

"Binding partner" refers to any substances that both bind to the moieties with desired affinity or specificity and are manipulatable with the desired physical force(s). Non-limiting examples of the binding partners include cells, cellular organelles, viruses, microparticles or an aggregate or complex thereof, or an aggregate or complex of molecules.

A "microparticle" or "particle" is a structure of any shape and of any composition that is manipulatable by desired physical force(s). The microparticles used in the methods could have a dimension from about 0.01 micron to about ten centimeters. Preferably, the microparticles used in the methods have a dimension from about 0.1 micron to about several thousand microns. Such particles or microparticles can be comprised of any suitable material, such as glass or ceramics, and/or one or more polymers, such as, for example, nylon, polytetrafluoroethylene (TEFLON™), polystyrene, polyacrylamide, sepaharose, agarose, cellulose, cellulose derivatives, or dextran, and/or can comprise metals. Examples of microparticles include, but are not limited to, plastic particles, ceramic particles, carbon particles, polystyrene microbeads, glass beads, magnetic beads, hollow glass spheres, metal particles, particles of complex compositions, microfabricated or micromachined particles, etc.

"Coupled" means bound. For example, a moiety can be coupled to a microparticle by specific or nonspecific binding. As disclosed herein, the binding can be covalent or noncovalent, reversible or irreversible.

As used herein, "the moiety to be manipulated is substantially coupled onto surface of the binding partner" means that a percentage of the moiety to be manipulated is coupled onto surface of the binding partner and can be manipulated by a suitable physical force via manipulation of the binding partner. Ordinarily, at least 0.1% of the moiety to be manipulated is coupled onto surface of the binding partner. Preferably, at least 1%, 5%, 10%, 20%, 30%, 40%, 50%, 60%, 70%, 80% or 90% of the moiety to be manipulated is coupled onto surface of the binding partner.

As used herein, "the moiety to be manipulated is completely coupled onto surface of the binding partner" means that at least 90% of the moiety to be manipulated is coupled onto surface of the binding partner. Preferably, at least 91%, 92%, 93%, 94%, 95%, 96%, 97%, 98%, 99% or 100% of the moiety to be manipulated is coupled onto surface of the binding partner.

A "specific binding member" is one of two different molecules having an area on the surface or in a cavity which specifically binds to and is thereby defined as complementary with a particular spatial and chemical organization of the other molecule. A specific binding member can be a member of an immunological pair such as antigen-antibody or antibody-antibody, can be biotin-avidin, biotin-streptavidin, or biotin-neutravidin, ligand-receptor, nucleic acid duplexes, IgG-protein A, DNA-DNA, DNA-RNA, RNA-RNA, and the like.

An "antibody" is an immunoglobulin molecule, and can be, as nonlimiting example, an IgG, an IgM, or other type of immunoglobulin molecule. As used herein, "antibody" also refers to a portion of an antibody molecule that retains the binding specificity of the antibody from which it is derived (for example, single chain antibodies or Fab fragments).

A "nucleic acid molecule" is a polynucleotide. A nucleic acid molecule can be DNA, RNA, or a combination of both. A nucleic acid molecule can also include sugars other than ribose and deoxyribose incorporated into the backbone, and thus can be other than DNA or RNA. A nucleic acid can comprise nucleobases that are naturally occurring or that do not occur in nature, such as xanthine, derivatives of nucleobases, such as 2-aminoadenine, and the like. A nucleic acid molecule of the present invention can have linkages other than phosphodiester linkages. A nucleic acid molecule of the present invention can be a peptide nucleic acid molecule, in which nucleobases are linked to a peptide backbone. A nucleic acid molecule can be of any length, and can be single-stranded, double-stranded, or triple-stranded, or any combination thereof.

"Homogeneous manipulation" refers to the manipulation of particles in a mixture using physical forces, wherein all particles of the mixture have the same response to the applied force.

"Selective manipulation" refers to the manipulation of particles using physical forces, in which different particles in a mixture have different responses to the applied force.

A "fluid sample" is any fluid from which components are to be separated or analyzed. A sample can be from any source, such as an organism, group of organisms from the same or different species, from the environment, such as from a body of water or from the soil, or from a food source or an industrial source. A sample can be an unprocessed or a processed sample. A sample can be a gas, a liquid, or a semi-solid, and can be a solution or a suspension. A sample can be an extract, for example a liquid extract of a soil or food sample, an extract of a throat or genital swab, or an extract of a fecal sample, or a wash of an internal area of the body.

A "blood sample" as used herein can refer to a processed or unprocessed blood sample, i.e., it can be a centrifuged, filtered, extracted, or otherwise treated blood sample, including a blood sample to which one or more reagents such as, but not limited to, anticoagulants or stabilizers have been added. An example of blood sample is a buffy coat that is obtained by processing human blood for enriching white blood cells. Another example of a blood sample is a blood sample that has been "washed" to remove serum components by centrifuging the sample to pellet cells, removing the serum supernatant, and resuspending the cells in a solution or buffer. Other blood samples include cord blood samples, bone marrow aspirates, internal blood or peripheral blood. A blood sample can be of any volume, and can be from any subject such as an animal or human. A preferred subject is a human.

A "rare cell" is a cell that is either 1) of a cell type that is less than 1% of the total nucleated cell population in a fluid sample, or 2) of a cell type that is present at less than one million cells per milliliter of fluid sample. A "rare cell of interest" is a cell whose enrichment is desirable.

A "white blood cell" is a leukocyte, or a cell of the hematopoietic lineage that is not a reticulocyte or platelet and that can be found in the blood of an animal or human. Leukocytes can include nature killer cells ("NK cells") and lymphocytes, such as B lymphocytes ("B cells") or T lymphocytes ("T cells"). Leukocytes can also include phagocytic cells, such as monocytes, macrophages, and granulocytes, including basophils, eosinophils and neutrophils. Leukocytes can also comprise mast cells.

A "red blood cell" or "RBC" is an erythrocyte. Unless designated a "nucleated red blood cell" ("nRBC") or "fetal nucleated red blood cell" or nucleated fetal red blood cell, as used herein, "red blood cell" is used to mean a non-nucleated red blood cell.

"Neoplastic cells" refers to abnormal cells that have uncontrolled cellular proliferation and can continue to grow after the stimuli that induced the new growth has been withdrawn. Neoplastic cells tend to show partial or complete lack of structural organization and functional coordination with the normal tissue, and may be benign or malignant.

A "malignant cell" is a cell having the property of locally invasive and destructive growth and metastasis. Examples of "malignant cells" include, but not limited to, leukemia cells, lymphoma cells, cancer cells of solid tumors, metastatic solid tumor cells (e.g., breast cancer cells, prostate cancer cells, lung cancer cells, colon cancer cells) in various body fluids including blood, bone marrow, ascistic fluids, stool, urine, bronchial washes etc.

A "cancerous cell" is a cell that exhibits deregulated growth and, in most cases, has lost at least one of its differentiated properties, such as, but not limited to, characteristic morphology, non-migratory behavior, cell-cell interaction and cell-signaling behavior, protein expression and secretion pattern, etc.

A "stem cell" is an undifferentiated cell that can give rise, through one or more cell division cycles, to at least one differentiated cell type.

A "progenitor cell" is a committed but undifferentiated cell that can give rise, through one or more cell division cycles, to at least one differentiated cell type. Typically, a stem cell gives rise to a progenitor cell through one or more cell divisions in response to a particular stimulus or set of stimuli, and a progenitor gives rise to one or more differentiated cell types in response to a particular stimulus or set of stimuli.

An "etiological agent" refers to any etiological agent, such as a bacteria, fungus, protozoan, virus, parasite or prion that can infect a subject. An etiological agent can cause symptoms or a disease state in the subject it infects. A human etiological agent is an etiological agent that can infect a human subject. Such human etiological agents may be specific for humans, such as a specific human etiological agent, or may infect a variety of species, such as a promiscuous human etiological agent.

"Subject" refers to any organism, such as an animal or a human. An animal can include any animal, such as a feral animal, a companion animal such as a dog or cat, an agricultural animal such as a pig or a cow, or a pleasure animal such as a horse.

A "chamber" is a structure that is capable of containing a fluid sample, in which at least one processing step can be performed. The chamber may have various dimensions and its volume may vary between ten microliters and 0.5 liter.

A "filtration chamber" is a chamber through which or in which a fluid sample can be filtered.

A "filter" is a structure that comprises one or more pores or slots of particular dimensions (that can be within a particular range), that allows the passage of some sample components but not others from one side of the filter to the other, based on the size, shape, and/or deformability of the particles. A filter can be made of any suitable material that prevents passage of insoluble particles, such as metal, ceramics, glass, silicon, plastics, polymers, fibers (such as paper or fabric), etc.

A "filtration unit" is a filtration chamber and the associated inlets, valves, and conduits that allow sample and solutions to be introduced into the filtration chamber and sample components to be removed from the filtration chamber. A filtration unit optionally also comprises a loading reservoir.

A "cartridge" is a structure that comprises at least one chamber that is part of a manual or automated system and one or more conduits for the transport of fluid into or out of at least one chamber. A cartridge may or may not comprise one or more chips.

An "automated system for separating rare cells from a fluid sample" or an "automated system" is a device that comprises at least one filtration chamber, automated means for directing fluid flow through the filtration chamber, and at least one power source for providing fluid flow and, optionally, providing a signal source for the generation of forces on active chips. An automated system of the present invention can also optionally include one or more active chips, separation chambers, separation columns, or permanent magnets.

A "port" is an opening in the housing of a chamber through which a fluid sample can enter or exit the chamber. A port can be of any dimensions, but preferably is of a shape and size that allows a sample to be dispensed into a chamber by pumping a fluid through a conduit, or by means of a pipette, syringe, or other means of dispensing or transporting a sample.

An "inlet" is a point of entrance for sample, solutions, buffers, or reagents into a fluidic chamber. An inlet can be a port of a chamber, or can be an opening in a conduit that leads, directly or indirectly, to a chamber of an automated system.

An "outlet" is the opening at which sample, sample components, or reagents exit a fluidic chamber. The sample components and reagents that leave a chamber can be waste, i.e., sample components that are not to be used further, or can be sample components or reagents to be recovered, such as, for example, reusable reagents or target cells to be further analyzed or manipulated. An outlet can be a port of a chamber, but preferably is an opening in a conduit that, directly or indirectly, leads from a chamber of an automated system.

A "conduit" is a means for fluid to be transported from a container to a chamber of the present invention. Preferably a conduit directly or indirectly engages a port in the housing of a chamber. A conduit can comprise any material that permits the passage of a fluid through it. Conduits can comprise tubing, such as, for example, rubber, Teflon, or tygon tubing. Conduits can also be molded out of a polymer or plastic, or drilled, etched, or machined into a metal, glass or ceramic substrate. Conduits can thus be integral to structures such as, for example, a cartridge of the present invention. A conduit can be of any dimensions, but preferably ranges from 10 microns to 5 millimeters in internal diameter. A conduit is preferably enclosed (other than fluid entry and exit points), or can be open at its upper surface, as a canal-type conduit.

A "chip" is a solid substrate on which one or more processes such as physical, chemical, biochemical, biological or biophysical processes can be carried out, or a solid substrate that comprises or supports one or more applied force-generating elements for carrying out one or more physical, chemical, biochemical, biological, or biophysical processes. Such processes can be assays, including biochemical, cellular, and chemical assays; separations, including separations mediated by electrical, magnetic, physical, and chemical (including biochemical) forces or interactions; chemical reactions, enzymatic reactions, and binding interactions, including captures. The micro structures or micro-scale structures such as, channels and wells, bricks, dams, filters, electrode elements, electromagnetic elements, or acoustic elements, may be incorporated into or fabricated on the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 $mm^2$ to about 0.25 $m^2$. Preferably, the size of the chips is from about 4 $mm^2$ to about 25 $cm^2$ with a characteristic dimension from about 1 mm to about 5 cm. The chip surfaces may be flat, or not flat. The chips with non-flat surfaces may include channels or wells fabricated on the surfaces. A chip can have one or more openings, such as pores or slots.

An "active chip" is a chip that comprises micro-scale structures that are built into or onto a chip that when energized by an external power source can generate at least one physical force that can perform a processing step or task or an analysis step or task, such as, but not limited to, mixing, translocation, focusing, separation, concentration, capture, isolation, or enrichment. An active chip uses applied physical forces to promote, enhance, or facilitate desired biochemical reactions or processing steps or tasks or analysis steps or tasks. On an active chip, "applied physical forces" are physical forces that, when energy is provided by a power source that is external to an active chip, are generated by micro-scale structures built into or onto a chip.

"Micro-scale structures" are structures integral to or attached on a chip, wafer, or chamber that have characteristic dimensions of scale for use in microfluidic applications ranging from about 0.1 micron to about 20 mm. Example of micro-scale structures that can be on chips of the present invention are wells, channels, dams, bricks, filters, scaffolds, electrodes, electromagnetic units, acoustic elements, or microfabricated pumps or valves. A variety of micro-scale structures are disclosed in U.S. patent application Ser. No. 09/679,024, entitled "Apparatuses Containing Multiple Active Force Generating Elements and Uses Thereof" filed Oct. 4, 2000, herein incorporated by reference in its entirety. Micro-scale structures that can, when energy, such as an electrical signal, is applied, generate physical forces useful in the present invention, can be referred to as "physical force-generating elements" "physical force elements", "active force elements", or "active elements".

A variety of micro-scale structures are disclosed in U.S. patent application Ser. No. 09/679,024, entitled "Apparatuses Containing Multiple Active Force Generating Elements and Uses Thereof" filed Oct. 4, 2000, herein incorporated by reference in its entirety. Micro-scale structures that can, when energy, such as an electrical signal, is applied, generate physical forces useful in the present invention, can be referred to as "physical force-generating elements" "physical force elements", "active force elements", or "active elements".

A "multiple force chip" or "multiforce chip" is a chip that generates physical force fields and that has at least two different types of built-in structures each of which is, in combination with an external power source, capable of generating one type of physical field. A full description of the multiple force chip is provided in U.S. application Ser. No. 09/679, 024, entitled "Apparatuses Containing Multiple Active Force Generating Elements and Uses Thereof" filed Oct. 4, 2000, herein incorporated by reference in its entirety.

"Acoustic forces" are the forces exerted, directly or indirectly on moieties (e.g., particles and/or molecules) by an acoustic wave field. Acoustic forces can be used for manipulating (e.g., trapping, moving, directing, handling) particles in fluid. Acoustic waves, both standing acoustic wave and traveling acoustic wave, can exert forces directly on moieties and such forces are called "acoustic radiation forces". Acoustic wave may also exert forces on the fluid medium in which the moieties are placed, or suspended, or dissolved and result in so-called acoustic streaming. The acoustic streaming, in turn, will exert forces on the moieties placed, suspended or dissolved in such a fluid medium. In this case, the acoustic wave fields can exert forces on moieties in directly.

"Acoustic elements" are structures that can generate an acoustic wave field in response to a power signal. Preferred acoustic elements are piezoelectric transducers that can generate vibrational (mechanical) energy in response to applied AC voltages. The vibrational energy can be transferred to a fluid that is in proximity to the transducers, causing an acoustic force to be exerted on particles (such as, for example, cells) in the fluid. A description of acoustic forces and acoustic elements can be found in U.S. patent application Ser. No. 09/636,104, filed Aug. 10, 2000, incorporated by reference in its entirety.

"Piezoelectric transducers" are structures capable of generating an acoustic field in response to an electrical signal. Non-limiting examples of the piezoelectric transducers are ceramic disks (e.g. PZT, Lead Zirconium Titinate) covered on both surfaces with metal film electrodes, piezoelectric thin films (e.g. zinc-oxide).

"Mixing" as used herein means the use of physical forces to cause particle movement in a sample, solution, or mixture, such that components of the sample, solution, or mixture become interspersed. Preferred methods of mixing for use in the present invention include use of acoustic forces.

"Processing" refers to the preparation of a sample for analysis, and can comprise one or multiple steps or tasks. Generally a processing task serves to separate components of a sample, concentrate components of a sample, at least partially purify components of a sample, or structurally alter components of a sample (for example, by lysis or denaturation).

As used herein, "isolating" means separating a desirable sample component from other nondesirable components of a sample, such that preferably, at least 15%, more preferably at least 30%, even more preferably at least 50%, and further preferably, at least 80% of the desirable sample components present in the original sample are retained, and preferably at least 50%, more preferably at least 80%, even more preferably, at least 95%, and yet more preferably, at least 99%, of at least one nondesirable component of the original component is removed, from the final preparation.

"Rare cells" are cells whose abundance in the original sample is either 1) less than 1% of the total nucleated cell population in a fluid sample, or 2) present at less than one million cells per milliliter of fluid sample.

"Enrich" means increase the concentration of a sample component of a sample relative to other sample components (which can be the result of reducing the concentration of other sample components), or increase the concentration of a sample component. For example, as used herein, "enriching" nucleated fetal cells from a blood sample means increasing the proportion of nucleated fetal cells to all cells in the blood sample, enriching cancer cells of a blood sample can mean increasing the concentration of cancer cells in the sample (for example, by reducing the sample volume) or reducing the concentration of other cellular components of the blood sample, and "enriching" cancer cells in a urine sample can mean increasing their concentration in the sample.

"Separation" is a process in which one or more components of a sample are spatially separated from one or more other components of a sample. A separation can be performed such that one or more sample components of interest is translocated to or retained in one or more areas of a separation apparatus and at least some of the remaining components are translocated away from the area or areas where the one or more sample components of interest are translocated to and/or retained in, or in which one or more sample components is retained in one or more areas and at least some or the remaining components are removed from the area or areas. Alternatively, one or more components of a sample can be translocated to and/or retained in one or more areas and one or more sample components can be removed from the area or areas. It is also possible to cause one or more sample components to be translocated to one or more areas and one or more sample components of interest or one or more components of a sample to be translocated to one or more other areas. Separations can be achieved through, for example, filtration, or the use of physical, chemical, electrical, or magnetic forces. Non-limiting examples of forces that can be used in separations are gravity, mass flow, dielectrophoretic forces, traveling-wave dielectrophoretic forces, and electromagnetic forces.

"Separating a sample component from a (fluid) sample" means separating a sample component from other components of the original sample, or from components of the sample that are remaining after one or more processing steps. "Removing a sample component from a (fluid) sample" means removing a sample component from other components of the original sample, or from components of the sample that are remaining after one or more processing steps.

"Capture" is a type of separation in which one or more moieties or sample components is retained in or on one or more areas of a surface, chamber, chip, tube, or any vessel that contains a sample, where the remainder of the sample can be removed from that area.

An "assay" is a test performed on a sample or a component of a sample. An assay can test for the presence of a component, the amount or concentration of a component, the composition of a component, the activity of a component, etc. Assays that can be performed in conjunction with the compositions and methods of the present invention include, but not limited to, immunocytochemical assays, interphase FISH (fluorescence in situ hybridization), karyotyping, immunological assays, biochemical assays, binding assays, cellular assays, genetic assays, gene expression assays and protein expression assays.

A "binding assay" is an assay that tests for the presence or concentration of an entity by detecting binding of the entity to a specific binding member, or that tests the ability of an entity to bind another entity, or tests the binding affinity of one entity for another entity. An entity can be an organic or inorganic molecule, a molecular complex that comprises, organic, inorganic, or a combination of organic and inorganic compounds, an organelle, a virus, or a cell. Binding assays can use detectable labels or signal generating systems that give rise to detectable signals in the presence of the bound entity. Standard binding assays include those that rely on nucleic acid hybridization to detect specific nucleic acid sequences, those that rely on antibody binding to entities, and those that rely on ligands binding to receptors.

A "biochemical assay" is an assay that tests for the presence, concentration, or activity of one or more components of a sample.

A "cellular assay" is an assay that tests for a cellular process, such as, but not limited to, a metabolic activity, a catabolic activity, an ion channel activity, an intracellular signaling activity, a receptor-linked signaling activity, a transcriptional activity, a translational activity, or a secretory activity.

A "genetic assay" is an assay that tests for the presence or sequence of a genetic element, where a genetic element can be any segment of a DNA or RNA molecule, including, but not limited to, a gene, a repetitive element, a transposable element, a regulatory element, a telomere, a centromere, or DNA or RNA of unknown function. As nonlimiting examples, genetic assays can be gene expression assays, PCR assays, karyotyping, or FISH. Genetic assays can use nucleic acid hybridization techniques, can comprise nucleic acid sequencing reactions, or can use one or more enzymes such as polymerases, as, for example a genetic assay based on PCR. A genetic assay can use one or more detectable labels, such as, but not limited to, fluorochromes, radioisotopes, or signal generating systems.

"FISH" or "fluorescence in situ hybridization" is an assay wherein a genetic marker can be localized to a chromosome by hybridization. Typically, to perform FISH, a nucleic acid probe that is fluorescently labeled is hybridized to interphase chromosomes that are prepared on a slide. The presence and location of a hybridizing probe can be visualized by fluorescence microscopy. The probe can also include an enzyme and be used in conjunction with a fluorescent enzyme substrate.

"Karyotyping" refers to the analysis of chromosomes that includes the presence and number of chromosomes of each type (for example, each of the 24 chromosomes of the human haplotype (chromosomes 1-22, X, and Y)), and the presence of morphological abnormalities in the chromosomes, such as, for example, translocations or deletions. Karyotyping typically involves performing a chromosome spread of a cell in metaphase. The chromosomes can then be visualized using, foe example, but not limited to, stains or genetic probes to distinguish the specific chromosomes.

A "gene expression assay (or "gene expression profiling assay") is an assay that tests for the presence or quantity of one or more gene expression products, i.e. messenger RNAs. The one or more types of mRNAs can be assayed simultaneously on cells of the interest from a sample. For different applications, the number and/or the types of mRNA molecules to be assayed in the gene expression assays may be different.

A "protein expression assay" (or "protein expression profiling assay") is an assay that tests for the presence or quantity of one or more proteins. One or more types of protein can be assayed simultaneously on the cells of the interest from a sample. For different applications, the number and/or the types of protein molecules to be assayed in the protein expression assays may be different.

"Histological examination" refers to the examination of cells using histochemical or stains or specific binding members (generally coupled to detectable labels) that can determine the type of cell, the expression of particular markers by the cell, or can reveal structural features of the cell (such as the nucleus, cytoskeleton, etc.) or the state or function of a cell. In general, cells can be prepared on slides and "stained" using dyes or specific binding members directly or indirectly bound to detectable labels, for histological examination. Examples of dyes that can be used in histological examination are nuclear stains, such as Hoescht stains, or cell viability stains, such as Trypan blue, or cellular structure stains such as Wright or Giemsa, enzyme activity benzidine for HRP to form visible precipitate. Examples of specific binding members that can be used in histological examination of fetal red blood cells are antibodies that specifically recognize fetal or embryonic hemoglobin.

An "electrode" is a structure of highly electrically conductive material. A highly conductive material is a material with a conductivity greater than that of surrounding structures or materials. Suitable highly electrically conductive materials include metals, such as gold, chromium, platinum, aluminum, and the like, and can also include nonmetals, such as carbon and conductive polymers. An electrode can be any shape, such as rectangular, circular, castellated, etc. Electrodes can also comprise doped semi-conductors, where a semi-conducting material is mixed with small amounts of other "impurity" materials. For example, phosphorous-doped silicon may be used as conductive materials for forming electrodes.

A "well" is a structure in a chip, with a lower surface surrounded on at least two sides by one or more walls that extend from the lower surface of the well or channel. The walls can extend upward from the lower surface of a well or channel at any angle or in any way. The walls can be of an irregular conformation, that is, they may extend upward in a sigmoidal or otherwise curved or multi-angled fashion. The lower surface of the well or channel can be at the same level as the upper surface of a chip or higher than the upper surface of a chip, or lower than the upper surface of a chip, such that the well is a depression in the surface of a chip. The sides or walls of a well or channel can comprise materials other than those that make up the lower surface of a chip.

A "channel" is a structure in a chip with a lower surface and at least two walls that extend upward from the lower surface of the channel, and in which the length of two opposite walls is greater than the distance between the two opposite walls. A channel therefore allows for flow of a fluid along its internal length. A channel can be covered (a "tunnel") or open.

A "pore" is an opening in a surface, such as a filter of the present invention, that provides fluid communication between one side of the surface and the other. A pore can be of any size and of any shape, but preferably a pore is of a size and shape that restricts passage of at least one insoluble sample component from one side of a filter to the other side of a filter based on the size, shape, and deformability (or lack thereof), of the sample component.

A "slot" is an opening in a surface, such as a filter of the present invention. The slot length is longer than its width (slot length and slot width refer to the slots dimensions in the plane or the surface of the filter into which the sample components will go through, and slot depth refers to the thickness of the filter). The term "slot" therefore describes the shape of a pore, which will in most cases be approximately rectangular, ellipsoid, or that of a quadrilateral or parallelogram.

"Bricks" are structures that can be built into or onto a surface that can restrict the passage of sample components between bricks. The design and use of one type of bricks (called "obstacles") on a chip is described in U.S. Pat. No. 5,837,115 issued Nov. 17, 1998 to Austin et al., herein incorporated by reference in its entirety.

A "dam" is a structure built onto the lower surface of a chamber that extends upward toward the upper surface of a chamber leaving a space of defined width between the top of the dam and the top of the chamber. Preferably, the width of the space between the top of the dam and the upper wall of the chamber is such that fluid sample can pass through the space, but at least one sample component is unable to pass through the space based on its size, shape, or deformability (or lack thereof). The design and use of one type of dam structure on a chip is described in U.S. Pat. No. 5,928,880 issued Jul. 27, 1999 to Wilding et al., herein incorporated by reference in its entirety.

"Continuous flow" means that fluid is pumped or injected into a chamber of the present invention continuously during the separation process. This allows for components of a sample that are not selectively retained in a chamber to be flushed out of the chamber during the separation process.

"Binding partner" refers to any substances that both bind to the moieties with desired affinity or specificity and are manipulatable with the desired physical force(s). Non-limiting examples of the binding partners include microparticles.

A "microparticle" is a structure of any shape and of any composition that is manipulatable by desired physical force(s). The microparticles used in the methods could have a dimension from about 0.01 micron to about ten centimeters. Preferably, the microparticles used in the methods have a dimension from about 0.1 micron to about several hundred microns. Such particles or microparticles can be comprised of any suitable material, such as glass or ceramics, and/or one or more polymers, such as, for example, nylon, polytetrafluoroethylene (TEFLON™), polystyrene, polyacrylamide, separaharose, agarose, cellulose, cellulose derivatives, or dextran, and/or can comprise metals. Examples of microparticles include, but are not limited to, magnetic beads, magnetic particles, plastic particles, ceramic particles, carbon particles, polystyrene microbeads, glass beads, hollow glass spheres, metal particles, particles of complex compositions, microfabricated free-standing microstructures, etc. The examples of microfabricated free-standing microstructures may include those described in "Design of asynchronous dielectric micromotors" by Hagedorn et al., in Journal of Electrostatics, Volume: 33, Pages 159-185 (1994). Particles of complex compositions refer to the particles that comprise or consists of multiple compositional elements, for example, a metallic sphere covered with a thin layer of non-conducting polymer film.

"A preparation of microparticles" is a composition that comprises microparticles of one or more types and can optionally include at least one other compound, molecule, structure, solution, reagent, particle, or chemical entity. For example, a preparation of microparticles can be a suspension of microparticles in a buffer, and can optionally include specific binding members, enzymes, inert particles, surfactants, ligands, detergents, etc.

Other technical terms used herein have their ordinary meaning in the art that they are used, as exemplified by a variety of technical dictionaries.

Introduction

The present invention recognizes that analysis of complex fluids, such as biological fluid samples, can be confounded by many sample components that can interfere with the analysis. Sample analysis can be even more problematic when the target of the analysis is a rare cell type, for example, when the target cells are fetal cells present in maternal blood or malignant cells present in the blood or urine of a patient. In processing such samples, it is often necessary to both "debulk" the sample, by reducing the volume to a manageable level, and to enrich the population of rare cells that are the target of analysis. Procedures for the processing of fluid samples are often time consuming and inefficient. The present invention provides efficient methods and automated systems for the enrichment of rare cells from fluid samples.

As a non-limiting introduction to the breath of the present invention, the present invention includes several general and useful aspects, including:

1) a microfabricated filter for filtering a fluid sample. A microfabricated filter of the present invention comprises at least one tapered pore, and preferably comprises at least two tapered pores whose variation in size is 20% or less.

2) a method of enriching rare cells of a fluid sample using a microfabricated filter of the present invention.

3) solutions for the selective sedimentation of red blood cells (RBCs) from a blood sample comprising a red blood cell aggregating agent and at least one specific binding member that selectively binds RBCs. The solution could also comprise at least one specific binding member that selectively binds other undesired components from a blood sample. Solutions of the present invention include a combined solution for rare cell enrichment that comprise dextran, at least one specific binding member that selectively binds RBCs, and at least one additional specific binding member for the removal of undesirable sample components other than RBCs such as but not limiting to the following examples, e.g. WBCs, platelets or serum proteins).

4) methods of using selective RBC sedimentation solutions and combined solutions for enriching rare cells of a fluid sample.

5) an automated system for processing a fluid sample that includes: at least one filtration chamber that comprises or engages one or more microfabricated filters of the present invention; automated means for directing fluid flow through the one or more filtration chambers of the automated system, and means for collecting enriched rare cells.

6) a method of using an automated system for separating rare cells from a fluid sample that includes: introducing a fluid sample into an automated system of the present invention, filtering the fluid sample using at least one filtration chamber of the automated system; and collecting enriched rare cells from at least one outlet or at least one vessel of the automated system. Preferably, the method also includes removing undesirable components of the fluid sample or separating rare cells of the sample in at least one vessel, chamber, or column of the present invention. A preferred fluid sample is an effusion, blood, or urine sample, and rare cells that can be enriched from such sample include nucleated fetal cells, stem cells and cancer cells.

7) an automated system for processing a fluid sample that includes: automated fluid volume sensing means for sensing the volume of at least one sample or a portion thereof provided in a tube or vessel; at least one filtration chamber that comprises or engages one or more microfabricated filters of the present invention; automated means for directing fluid flow through the one or more filtration chambers of the automated system, and means for collecting enriched rare cells.

8) a method of using an automated system for separating rare cells from a fluid sample that includes: providing a fluid sample in a tube or vessel; using automated fluid sensing means of the automated system to determine the volume of the sample, or a portion thereof; filtering the fluid sample using at least one filtration chamber of the automated system; and collecting enriched rare cells from at least one outlet or at least one vessel of the automated system. Preferably, the method also includes removing undesirable components of the fluid sample or separating rare cells of the sample in at least one vessel, chamber, or column of the present invention. A preferred fluid sample is an effusion, blood, or urine sample, and rare cells that can be enriched from such sample include nucleated fetal cells, stem cells, and cancer cells.

9) a method of enriching a rare cell, such as a cancer cell, from a biological sample including performing at least one debulking step on a blood sample and selectively removing at least one type of undesirable component from the blood sample to enrich a rare cell of interest in the blood sample. Selective removal may occur by contacting the blood sample with one or more specific binding members that are specific to one or more types of undesirable components, the specific binding members being optionally coupled to a solid support such as a microbead or magnetic bead. Examples of suitable specific binding members are antibodies or antibody fragments such as those capable of binding CD3, CD11b, CD14, CD17, CD31, CD36, CD41, CD42 (a, b, c), CD45, CD50, CD51, CD51/61, CD53, CD63, CD69, CD81, CD84, CD102 or CD166. White blood cells are one type of undesirable component. Debulking, such as removing red blood cells, may be performed using nonlimiting methods such as sedimentation, lysis, centrifugation and the like. Rare cells, such a cancer cells or other non-hematopietic cells may be labeled and/or further isolated.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

I Microfabricated Filter

The present invention includes a microfabricated filter that comprises at least one tapered pore, where a pore is an opening in the filter. A pore can be of any shape and any dimensions. For example, a pore can be quadrilateral, rectangular, ellipsoid, or circular in shape, or of other geometric or non-geometric shape. A pore can have a diameter (or widest dimension) from about 0.1 micron to about 1000 microns, preferably from about 20 to about 200 microns, depending on the filtering application. Preferably, a pore is made during the machining of a filter, and is microetched or bored into the filter material that comprises a hard, fluid-impermeable material such as glass, silicon, ceramics, metal or hard plastic such as acrylic, polycarbonate, or polyimide. It is also possible to use a relatively nonhard surface for the filter that is supported on a hard solid support. Another aspect of this invention is to modify the material (for example but not limited to chemically or thermally modifying the material to silicon oxide or silicon nitride). Preferably, however, the filter comprises a hard material that is not deformable by the pressure (such as suction pressure) used in generating fluid flow through the filter.

A slot is a pore with a length that is greater than its width, where "length" and "width" are dimensions of the opening in the plane of the filter. (The "depth" of the slot corresponds to the thickness of the filter.) That is, "slot" describes the shape of the opening, which will in most cases be approximately rectangular or ellipsoid, but can also approximate a quadrilateral or parallelogram. In preferred embodiments of the present invention in which slot width is the critical dimension in determining which sample components flow through or are retained by the filter, the shape of the slot can vary at the ends (for example, be regular or irregular in shape, curved or angular), but preferably the long sides of the slot are a consistent distance from one another for most of the length of the slot, that distance being the slot width. Thus the long sides of a slot will be parallel or very nearly parallel, for most of the length of the slot.

Preferably, the filters used for filtration in the present invention are microfabricated or micromachined filters so that the pores or the slots within a filter can achieve precise and uniform dimensions. Such precise and uniform pore or slot dimensions are a distinct advantage of the microfabricated or micromachined filters of the present invention, in comparison with the conventional membrane filters made of materials such as nylon, polycarbonate, polyester, mixed cellulose ester, polytetrafluoroethylene, polyethersulfone, etc. In the filters of the present invention, individual pores are isolated, have similar or almost identical feature sizes, and are patterned on a filter. Such filters allow precise separation of particles based on their sizes and other properties.

The filtration area of a filter is determined by the area of the substrate comprising the pores. The filtration area for microfabricated filters of the present invention can be between about 0.01 mm$^2$ and about 0.1 mm$^2$. Preferably, the filtration area is between about 0.25 mm$^2$ and about 25 cm$^2$, and more preferably is between about 0.5 mm$^2$ and about 10 cm$^2$. The large filtration areas allow the filters of the invention to process sample volumes from about 100 microliters to about 10 liters. The percent of the filtration area encompassed by pores can be from about 1% to about 70%, preferably is from about 10% to about 50%, and more preferably is from about 15 to about 40%. The filtration area of a microfabricated filter of the present invention can comprise any number of pores, and preferably comprises at least two pores, but more preferably the number of pores in the filtration area of a filter of the present invention ranges from about 4 to about 1,000,000, and even more preferably ranges from about 100 to about 250,000. The thickness of the filter in the filtration area can range from about 10 to about 500 microns, but is preferably in the range of between about 40 and about 100 microns.

The microfabricated filters of the present invention have slots or pores that are etched through the filter substrate itself. The pores or openings of the filters can be made by using microfabrication or micromachining techniques on substrate materials, including, but not limited to, silicon, silicon dioxide, ceramics, glass, polymers such as polyimide, polyamide, etc. Various fabrication methods, as known to those skilled in the art of microlithography and microfabrication (See, for example, Rai-Choudhury P. (Editor), Handbook of Microlithography, Micromachining and Microfabrication, Volume 2: Micromachining and microfabrication. SPIE Optical Engineering Press, Bellingham, Wash., USA (1997)), may be used. In many cases, standard microfabrication and micromachining methods and protocols may be involved. One example of suitable fabrication methods is photolithography involving single or multiple photomasks. The protocols in the microfabrication may include many basic steps, for example, photolithographic mask generation, deposition of photoresist, deposition of "sacrificial" material layers, photoresist patterning with masks and developers, or "sacrificial" material layer patterning. Pores can be made by etching into the substrate under certain masking process so that the regions that have been masked are not etched off and the regions that have not been mask-protected are etched off. The etching method can be dry-etching such as deep RIE (reactive ion etching), laser ablation, or can be wet etching involving the use of wet chemicals.

Figure 4:
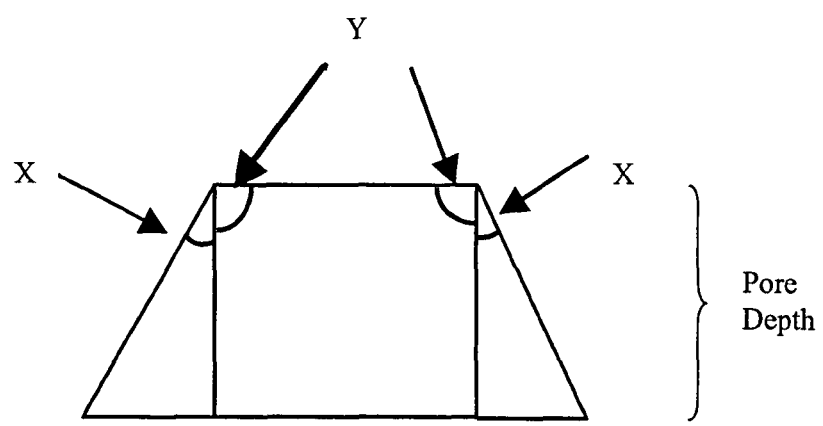
FIG. 4 depicts a cross section of a pore in a microfabricated filter of the present invention. The pore depth corresponds to the filter thickness. Y represents the right angle between the surface of the filter and the side of a pore cut perpendicularly through the filter, while X is the tapering angle by which a tapered pore differs in its direction or orientation through the filter from a nontapered pore.

Preferably, appropriate microfabrication or micromachining techniques are chosen to achieve a desired aspect ratio for the filter pores. The aspect ratio refers to the ratio of the slot depth (corresponding to the thickness of the filter in the region of the pores) to the slot width or slot length. The fabrication of filter slots with higher aspect ratios (i.e., greater slot depth) may involve deep etching methods. Many fabrication methods, such as deep RIE, useful for the fabrication of MEMS (micro electronic mechanical systems) devices can be used or employed in making the microfabricated filters. The resulting pores can, as a result of the high aspect ratio and the etching method, have a slight tapering, such that their openings are narrower on one side of the filter than the other. For example, in FIG. 4, the angle Y, of a hypothetical pore bored straight through the filter substrate is 90 degrees, and the tapering angle X by which a tapered pore of a microfabricated filter of the present invention differs from the perpendicular is between about 0 degree and about 90 degrees, and preferably between 0.1 degrees and 45 degrees and most preferably between about 0.5 degrees and 10 degrees, depending on the thickness of the filter (pore depth).

The present invention includes microfabricated filters comprising two or more tapered pores. The substrate on which the filter pores, slots or openings are fabricated or machined may be silicon, silicon dioxide, plastic, glass, ceramics or other solid materials. The solid materials may be porous or non-porous. Those who are skilled in microfabrication and micromachining fabrication may readily choose and determine the fabrication protocols and materials to be used for fabrication of particular filter geometries.

Using the microfabrication or micromachining methods, the filter slots, pores or openings can be made with precise geometries. Depending on the fabrication methods or materials used, the accuracy of a single dimension of the filter slots (e.g. slot length, slot width) can be within 20%, or less than 10%, or less than 5%. Thus, the accuracy of the critical, single dimension of the filter pores (e.g. slot width for oblong or quadrilateral shaped slots) for the filters of the present invention are made within, preferably, less than 2 microns, more preferably, less than 1 micron, or even more preferably less than 0.5 micron.

Preferably, filters of the present invention can be made using the track-etch technique, in which filters made of glass, silicon, silicon dioxides, or polymers such as polycarbonate or polyester with discrete pores having relatively-uniform pore sizes are made. For example, the filter can be made by adapting and applying the track-etch technique described at whatman.com/products/nucleopore/tech$_{13}$ frame.htm for Nucleopore Track-etch membranes to filter substrates. In the technique used to make membrane filters, a thin polymer film is tracked with energetic heavy ions to produce latent tracks on the film. The film is then put in an etchant to produce pores.

Preferred filters for the cell separation methods and systems of the present invention include microfabricated or micromachined filters that can be made with precise geometries for the openings on the filters. Individual openings are isolated with similar or almost identical feature sizes and are patterned on a filter. The openings can be of different shapes such as, for example, circular, quadrilateral, or elliptical. Such filters allow precise separation of particles based on their sizes and other properties.

In a preferred embodiment of a microfabricated filter, individual pores are isolated and of a cylindrical shape, and the pore size is within a 20% variation, where the pore size is calculated by the smallest and largest dimension of the pore (width and length, respectively).

Filter Treatment or Modification

The present invention also includes methods of treating a microfabricated filter to improve its filtering efficiency. In these methods, one or both surfaces of the filter is treated or coated or modified to increase its filtering efficiency. In a preferred method, one or both surfaces of the filter is treated or modified to reduce the possibility of sample components (such as but not limited to cells) interacting with or adhering to the filter.

A filter can be physically or chemically treated, for example, to alter its surface properties (e.g. hydrophobic, hydrophilic). For example, a filter can be heated or treated with oxygen plasma, modified to silicon nitride or can be treated with at least one acid or at least one base, to increase its hydrophilicity or surface charge. For example, a glass or silica filter can be heated to oxidize the surface of the filter. Heating times and temperatures can vary depending on the filter material and the degree of oxidation desired. In one example, a glass filter can be heated to a temperature of from about 200 to 1000 degrees Celsius for from about thirty minutes to twenty-four hours.

In another example, a filter can be treated with one or more acids or one or more bases to increase the hydrophilicity of the filter surface. In preferred embodiments, a filter that comprises glass or silica is treated with at least one acid.

An acid used in treating a filter of the present invention can be any acid. As nonlimiting examples, the acid can be HCl, $H_2SO_4$, $NaHSO_4$, $HSO_4$, $HNO_3$, HF, $H_3PO_4$, HBr, HCOOH, or $CH_3COOH$. The acid can be of a concentration about 0.1 N or greater, and preferably is about 0.5 N or higher in concentration, and more preferably is greater than about 1 N in concentration. For example, the concentration of acid preferably is from about 1 N to about 10 N. The incubation time can be from one minute to days, but preferably is from about 5 minutes to about 2 hours.

Optimal concentrations and incubation times for treating a microfabricated filter to increase its hydrophilicity can be determined empirically. The microfabricated filter can be placed in a solution of acid for any length of time, preferably for more than one minute, and more preferably for more than about five minutes. Acid treatment can be done under any non-freezing and non-boiling temperature, preferably at a temperature greater than or equal to room temperature.

Alternatively or in addition, a microfabricated filter of the present invention can be treated with a base, such as a basic solution, that can comprise, as nonlimiting examples, NaOH, KOH, Ba(OH)$_2$, LiOH, CsOH, or Ca(OH)$_2$. The basic solution can be of a concentration of about 0.01 N or greater, and preferably is greater than about 0.05 N, and more preferably greater than about 0.1 N in concentration. The ion transport measuring means can be placed in a solution of base for any length of time, preferably for more than one minute, and more preferably for more than about five minutes. Base treatment can be done under any non-frozen and non-boiling temperature, preferably at a temperature greater than or equal to room temperature.

Figure 5:
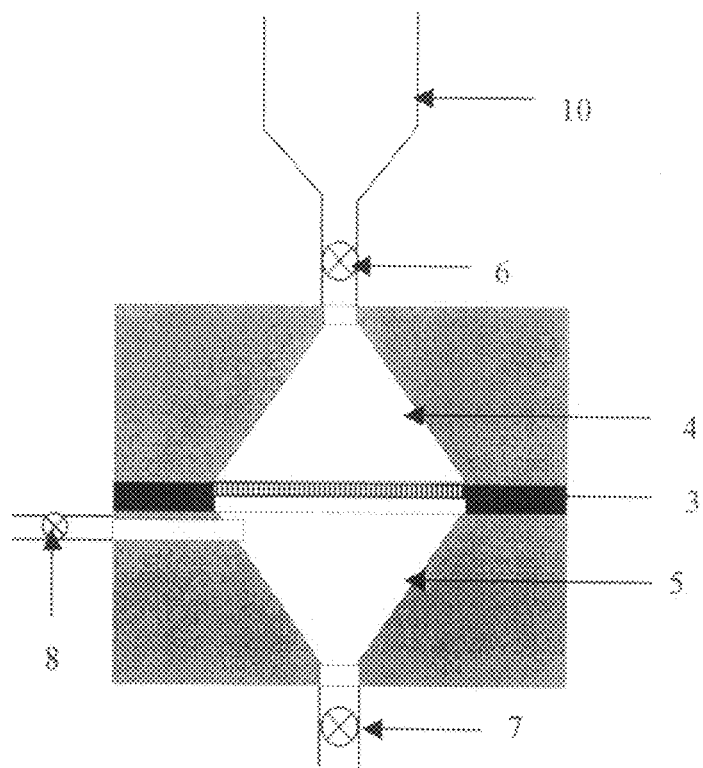
FIG. 5 depicts a filtration unit of the present invention having a microfabricated filter (3) separating the filtration chamber into an upper antechamber (4) and a post-filtration subchamber (5). The unit has valves to control fluid flow into and out of the unit: valve A (6) controls the flow of sample from the loading reservoir (10) into the filtration unit, valve B (7) controls fluid flow through the chamber by connection to a syringe pump, and valve C (8) is used for the introduction of wash solution into the chamber.

The effectiveness of a physical or chemical treatment in increasing the hydrophilicity of a filter surface can be tested by measuring the spread of a drop of water placed on the surface of a treated and non-treated filter, where increased spreading of a drop of uniform volume indicates increased hydrophilicity of a surface (FIG. 5). The effectiveness of a filter treatment can also be tested by incubating a treated filter with cells or biological samples to determine the degree of sample component adhesion to the treated filter.

In another embodiment, the surface of a filter, such as but not limited to a polymeric filter, can chemically treated to alter the surface properties of the filter. For example, the surface of a glass, silica, or polymeric filter can be derivatized by any of various chemical treatments to add chemical groups that can decrease the interaction of sample components with the filter surface One or more compounds can also be adsorbed onto or conjugated to the surface of a microfabricated filter made of any suitable material, such as, for example, one or more metals, one or more ceramics, one or more polymers, glass, silica, silicon dioxide, or combinations thereof. In preferred embodiments of the present invention, the surface or surfaces of a microfabricated filter of the present invention is coated with a compound to increase the efficiency of filtration by reducing the interaction of sample components with the filter surface.

For example, the surface of a filter can be coated with a molecule, such as, but not limited to, a protein, peptide, or polymer, including naturally occurring or synthetic polymers. The material used to coat the filter is preferably biocompatible, meaning it does not have deleterious effects on cells or other components of biological samples, such as proteins, nucleic acids, etc. Albumin proteins, such as bovine serum albumin (BSA) are examples of proteins that can be used to coat a microfabricated filter of the present invention. Polymers used to coat a filter can be any polymer that does not promote cell sticking to the filter, for example, nonhydrophobic polymers such as, but not limited to, polyethylene glycol (PEG), polyvinylacetate (PVA), and polyvinylpyrrolidone (PVP), and a cellulose or cellulose-like derivative.

A filter made of, for example, metal, ceramics, a polymer, glass, or silica can be coated with a compound by any feasible means, such as, for example, adsorption or chemical conjugation.

In many cases, it can be advantageous to surface-treat the filter prior to coating with a compound or polymer. Surface treatment can increase the stability and uniformity of the coating. For example, a filter can be treated with at least one acid or at least one base, or with at least one acid and at least one base, prior to coating the filter with a compound or polymer. In preferred aspects of the present invention, a filter made of a polymer, glass, or silica is treated with at least one acid and then incubated in a solution of the coating compound for a period of time ranging from minutes to days. For example, a glass filter can be incubated in acid, rinsed with water, and then incubated in a solution of BSA, PEG, or PVP.

In some aspects of the present invention, it can be preferred to rinse the filter, such as in water (for example, deionized water) or a buffered solution before acid or base treatment or treatment with an oxidizing agent, and, preferably again before coating the filter with a compound or polymer. Where more than one type of treatment is performed on a microfabricated filter, rinses can also be performed between treatments, for example, between treatment with an oxidizing agent and an acid, or between treatment with an acid and a base. A filter can be rinsed in water or an aqueous solution that has a pH of between about 3.5 and about 10.5, and more preferably between about 5 and about 9. Nonlimiting examples of suitable aqueous solutions for rinsing ion transport measuring means can include salt solutions (where salt solutions can range in concentration from the micromolar range to 5M or more), biological buffer solutions, cell media, or dilutions or combinations thereof. Rinsing can be performed for any length of time, for example from minutes to hours.

The concentration of a compound or polymer solution used to coat a filter can vary from about 0.02% to 20% or more, and will depend in part on the compound used. The incubation in coating solution can be from minutes to days, and preferably is from about 10 minutes to two hours.

After coating, the filter can be rinsed in water or a buffer.

The treatment methods of the present invention can also be applied to chips other than those that comprise pores for filtration. For example, chips that comprises metals, ceramics, one or more polymers, silicon, silicon dioxide, or glass can be physically or chemically treated using the methods of the present invention. Such chips can be used, for example, in separation, analysis, and detection devices in which biological species such as cells, organelles, complexes, or biomolecules (for example, nucleic acids, proteins, small molecules) are separated, detected, or analyzed. The treatment of the chip can enhance or reduce the interaction of the biological species with the chip surface, depending of the treatment used, the properties of the biological species being manipulated, and the nature of the manipulation. For example, a chip can be coated with a hydrophilic or hydrophobic polymer, depending on the biological species being manipulated and the nature of the manipulation. As a further example, coating the surface of the chip with a hydrophilic polymer (for example but not limited to coating the chip with PVP or PVA) may reduce or minimize the interaction between the surface of the chip and the cells.

Filter Comprising Electrodes

In some preferred embodiments, traveling-wave dielectrophoretic forces can be generated by electrodes built onto a chip that is part of a filtration chamber, and can be used to move sample components such as cells away from a filter. In this case, the microelectrodes are fabricated onto the filter surfaces and the electrodes are arranged so that the traveling wave dielectrophoresis can cause the sample components such as cells to move on the electrode plane or the filter surface through which the filtration process occur. A full description of the traveling wave dielectrophoresis is provided in U.S. application Ser. No. 09/679,024, entitled "Apparatuses Containing Multiple Active Force Generating Elements and Uses Thereof" filed Oct. 4, 2000, herein incorporated by reference in its entirety.

Figure 2A:
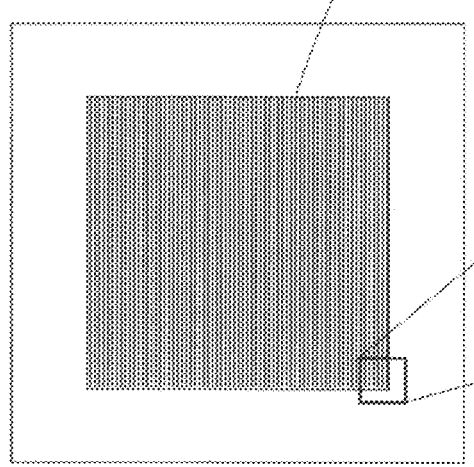
FIG. 2 is a schematic representation of a microfabricated filter of the present invention. A) the top view, showing an 18×18 mm$^2$ microfabricated filter having a filtration area (1) of 10×10 mm$^2$. B) an enlargement of a section of the top view, showing the slots (2) having dimensions of 4 microns×50 microns, with the center to center distance between slots of 12 microns, and their parallel alignment. C) a cross-sectional view of the microfabricated filter, with the slots extending through the filter substrate.
Figure 2B:
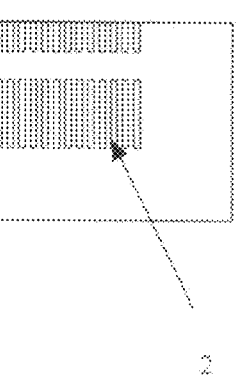
Figure 2C:

In one embodiment of the filters, interdigitated microelectrodes are fabricated onto the filter surfaces such as those shown in FIG. 2 or described in "Novel dielectrophoresis-based device of the selective retention of viable cells in cell culture media" by Docoslis et al., in Biotechnology and Bioengineering, Vol. 54, No. 3, pages 239-250, 1997, and in the U.S. Pat. No. 5,626,734, issued to Docoslis et al. on May 7, 1997. For this embodiment, the negative dielectrophoretic forces generated by the electrodes can repel the sample components such as the cells from the filter surface or from the filter slots so that the collected cells on the filters are not clogging the filters during the filtration process. Where traveling-wave dielectrophoresis or negative dielectrophoresis is used to enhance filtration, electrode elements can be energized periodically throughout the filtration process, during periods when fluid flow is halted or greatly reduced.

Figure 3A:
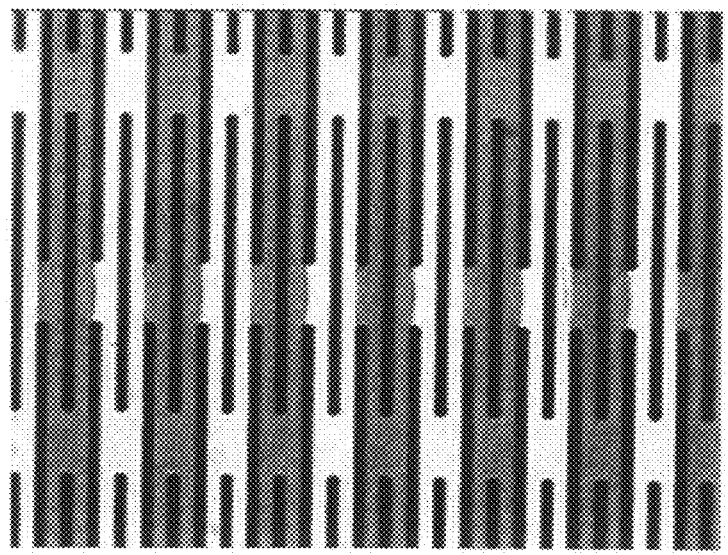
FIG. 3 depicts filters of the present invention having electrodes incorporated into their surfaces. A) a 20-fold magnification of a portion of a microfabricated filter having 2 micron slot widths. B) a 20-fold magnification of a portion of a microfabricated filter having 3 micron slot widths.
Figure 3B:
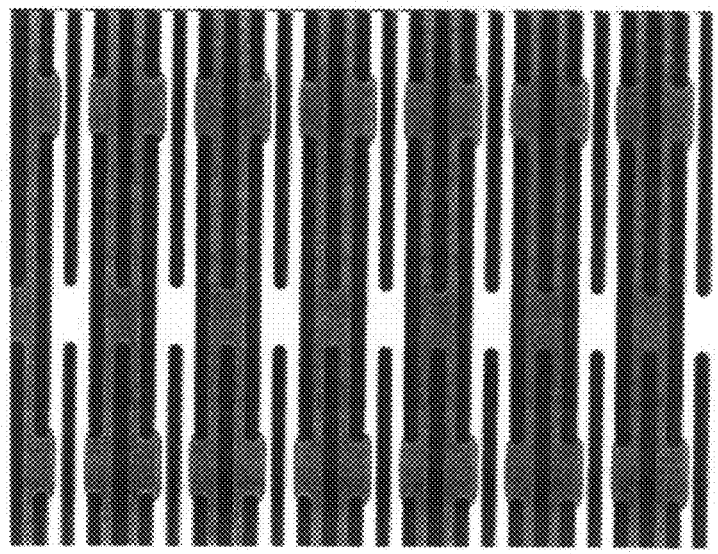

Filters having slots in the micron range that incorporate electrodes that can generate dielectrophoretic forces are illustrated in FIG. 3 (A and B). For example, filters have been made in which the interdigitated electrodes of 18 micron width and 18 micron gaps were fabricated on the filters, which were made on silicon substrates. Individual filter slots were of rectangular shape with dimensions of 100 micron (length) by 2-3.8 micron (width). Each filter had a unique slot size (e.g. length by width: 100 micron by 2.4 micron, 100 micron by 3 micron, 100 micron by 3.8 micron). Along the length direction, the gap between the adjacent filter slots was 20 micron. Along the width direction, the adjacent slots were not aligned; instead, they were offset. The offset distance between neighboring columns of the filter slots were 50 micron or 30 micron, alternatively. The filter slots were positioned with respect to the electrodes so that the slot center lines along the length direction were aligned with the center line of the electrodes, or the electrode edges, or the center line of the gaps between the electrodes.

The following discussion and references can provide a framework for the design and use of electrodes to facilitate filtration by translocating sample components, such as non-filterable cells, away from a filter:

Dielectrophoresis refers to the movement of polarized particles in a non-uniform AC electrical field. When a particle is placed in an electrical field, if the dielectric properties of the particle and its surrounding medium are different, the particle will experience dielectric polarization. Thus, electrical charges are induced at the particle/medium interface. If the applied field is non-uniform, then the interaction between the non-uniform field and the induced polarization charges will produce net force acting on the particle to cause particle motion towards the region of strong or weak field intensity. The net force acting on the particle is called dielectrophoretic force and the particle motion is dielectrophoresis. Dielectrophoretic force depends on the dielectric properties of the particles, particle surrounding medium, the frequency of the applied electrical field and the field distribution.

Traveling-wave dielectrophoresis is similar to dielectrophoresis in which the traveling-electric field interacts with the field-induced polarization and generates electrical forces acting on the particles. Particles are caused to move either with or against the direction of the traveling field. Traveling-wave dielectrophoretic forces depend on the dielectric properties of the particles and their suspending medium, the frequency and the magnitude of the traveling-field. The theory for dielectrophoresis and traveling-wave dielectrophoresis and the use of dielectrophoresis for manipulation and processing of microparticles may be found in various publications (e.g., "Non-uniform Spatial Distributions of Both the Magnitude and Phase of AC Electric Fields determine Dielectrophoretic Forces by Wang et al., in *Biochim Biophys Acta* Vol. 1243, 1995, pages 185-194", "Dielectrophoretic Manipulation of Particles" by Wang et al., in IEEE Transaction on Industry Applications, Vol. 33, No. 3, May/June, 1997, pages 660-669, "Electrokinetic behavior of colloidal particles in traveling electric fields: studies using yeast cells" by Huang et al., in J. Phys. D: Appl. Phys., Vol. 26, pages 1528-1535, "Positioning and manipulation of cells and microparticles using miniaturized electric field traps and traveling waves" By Fuhr et al., in Sensors and Materials. Vol. 7: pages 131-146, "Dielectrophoretic manipulation of cells using spiral electrodes" by Wang, X-B. et al., in *Biophys. J.* Volume 72, pages 1887-1899, 1997, "Separation of human breast cancer cells from blood by differential dielectric affinity" by Becker et al., in Proc. Natl. Acad. Sci., Vol., 92, January 1995, pages 860-864). The manipulation of microparticles with dielectrophoresis and traveling wave dielectrophoresis include concentration/aggregation, trapping, repulsion, linear or other directed motion, levitation, separation of particles. Particles may be focused, enriched and trapped in specific regions of the electrode reaction chamber. Particles may be separated into different subpopulations over a microscopic scale. Relevant to the filtration methods of the present invention, particles may be transported over certain distances. The electrical field distribution necessary for specific particle manipulation depends on the dimension and geometry of microelectrode structures and may be designed using dielectrophoresis theory and electrical field simulation methods.

The dielectrophoretic force $F_{DEPz}$ acting on a particle of radius r subjected to a non-uniform electrical field can be given by $$F_{DEPz}=2\pi \in_m r^3 \chi_{DEP} \nabla E^2_{rms} \cdot \bar{a}_z$$

where $E_{rms}$ is the RMS value of the field strength, $\in_m$ is the dielectric permitivity of the medium. $\chi_{DEP}$ is the particle dielectric polarization factor or dielectrophoresis polarization factor, given by $$\chi_{DEP} = \text{Re}\left(\frac{\varepsilon_p^* - \varepsilon_m^*}{\varepsilon_p^* + 2\varepsilon_m^*}\right),$$

"Re" refers to the real part of the "complex number". The symbol $$\varepsilon_x^* = \varepsilon_x - j\frac{\sigma_x}{2\pi f}$$

is the complex permitivity (of the particle x=p, and the medium x=m). The parameters $\in_p$ and $\sigma_p$ are the effective permitivity and conductivity of the particle, respectively. These parameters may be frequency dependent. For example, a typical biological cell will have frequency dependent, effective conductivity and permitivity, at least, because of cytoplasm membrane polarization.

The above equation for the dielectrophoretic force can also be written as $$F_{DEPz}=2\pi \in_m r^3 \chi_{DEP} V^2 p(z) \bar{a}_z$$

where p(z) is the square-field distribution for a unit-voltage excitation (V=1 V) on the electrodes, V is the applied voltage.

There are generally two types of dielectrophoresis, positive dielectrophoresis and negative dielectrophoresis. In positive dielectrophoresis, particles are moved by dielectrophoresis forces towards the strong field regions. In negative dielectrophoresis, particles are moved by dielectrophoresis forces towards weak field regions. Whether particles exhibit positive and negative dielectrophoresis depends on whether particles are more or less polarizable than the surrounding medium. In the filtration methods of the present invention, electrode patterns on one or more filters of a filtration chamber can be designed to cause sample components such as cells to exhibit negative dielectrophoresis, resulting in sample components such as cells being repelled away from the electrodes on the filter surfaces.

Traveling-wave DEP force refers to the force that is generated on particles or molecules due to a traveling-wave electric field. A traveling-wave electric field is characterized by the non-uniform distribution of the phase values of AC electric field components.

Here we analyze the traveling-wave DEP force for an ideal traveling-wave field. The dielectrophoretic force $F_{DEP}$ acting on a particle of radius r subjected to a traveling-wave electrical field $E_{TWD}=E\cos(2\pi(ft-z/\lambda_0))\bar{a}_x$ (i.e., a x-direction field is traveling along the z-direction) is given by $$F_{TWD} = -2\pi \epsilon_m r^3 \zeta_{TWD} E^2 \cdot \bar{a}_z$$

where E is the magnitude of the field strength, $\epsilon_m$ is the dielectric permittivity of the medium. $\zeta_{TWD}$ is the particle polarization factor, given by $$\zeta_{TWD} = \text{Im}\left(\frac{\varepsilon_p^* - \varepsilon_m^*}{\varepsilon_p^* + 2\varepsilon_m^*}\right),$$

"Im" refers to the imaginary part of the "complex number". The symbol $$\varepsilon_x^* = \varepsilon_x - j\frac{\sigma_x}{2\pi f}$$

is the complex permittivity (of the particle x=p, and the medium x=m). The parameters $\epsilon_p$ and $\sigma_p$ are the effective permittivity and conductivity of the particle, respectively. These parameters may be frequency dependent.

Particles such as biological cells having different dielectric property (as defined by permittivity and conductivity) will experience different dielectrophoretic forces. For traveling-wave DEP manipulation of particles (including biological cells), traveling-wave DEP forces acting on a particle of 10 micron in diameter can vary somewhere between 0.01 and 10000 pN.

A traveling wave electric field can be established by applying appropriate AC signals to the microelectrodes appropriately arranged on a chip. For generating a traveling-wave-electric field, it is necessary to apply at least three types of electrical signals each having a different phase value. An example to produce a traveling wave electric field is to use four phase-quardrature signals (0, 90, 180 and 270 degrees) to energize four linear, parallel electrodes patterned on the chip surfaces. Such four electrodes form a basic, repeating unit. Depending on the applications, there may be more than two such units that are located next to each other. This will produce a traveling-electric field in the spaces above or near the electrodes. As long as electrode elements are arranged following certain spatially sequential orders, applying phase-sequenced signals will result in establishing traveling electrical fields in the region close to the electrodes.

Both dielectrophoresis and traveling-wave dielectrophoresis forces acting on particles depend on not only the field distributions (e.g., the magnitude, frequency and phase distribution of electrical field components; the modulation of the field for magnitude and/or frequency) but also the dielectric properties of the particles and the medium in which particles are suspended or placed. For dielectrophoresis, if particles are more polarizable than the medium (e.g., having larger conductivities and/or permittivities depending on the applied frequency), particles will experience positive dielectrophoresis forces and are directed towards the strong field regions. The particles that are less polarizable than the surrounding medium will experience negative dielectrophoresis forces and are directed towards the weak field regions. For traveling wave dielectrophoresis, particles may experience dielectrophoresis forces that drive them in the same direction as the field traveling direction or against it, dependent on the polarization factor $\zeta_{TWD}$. The following papers provide basic theories and practices for dielectrophoresis and traveling-wave-dielectrophoresis: Huang, et al., *J. Phys. D: Appl. Phys.* 26:1528-1535 (1993); Wang, et al., *Biochim. Biophys. Acta.* 1243:185-194 (1995); Wang, et al., *IEEE Trans. Ind. Appl.* 33:660-669 (1997).

Filtration Chamber

A filtration chamber or the present invention is any chamber that can contain a fluid sample that comprises or engages at least one microfabricated filter of the present invention. A filtration chamber of the present invention can comprise one or more fluid-impermeable materials, such as but not limited to, metals, polymers, plastics, ceramics, glass, silicon, or silicon dioxide. Preferably, a filtration chamber of the present invention has a volumetric capacity of from about 0.01 milliliters to about ten liters, more preferably from about 0.2 milliliters to about two liters. In some preferred embodiments of the present invention, a filtration chamber can have a volume of from about 1 milliliter to about 80 milliliters.

Figure 6:
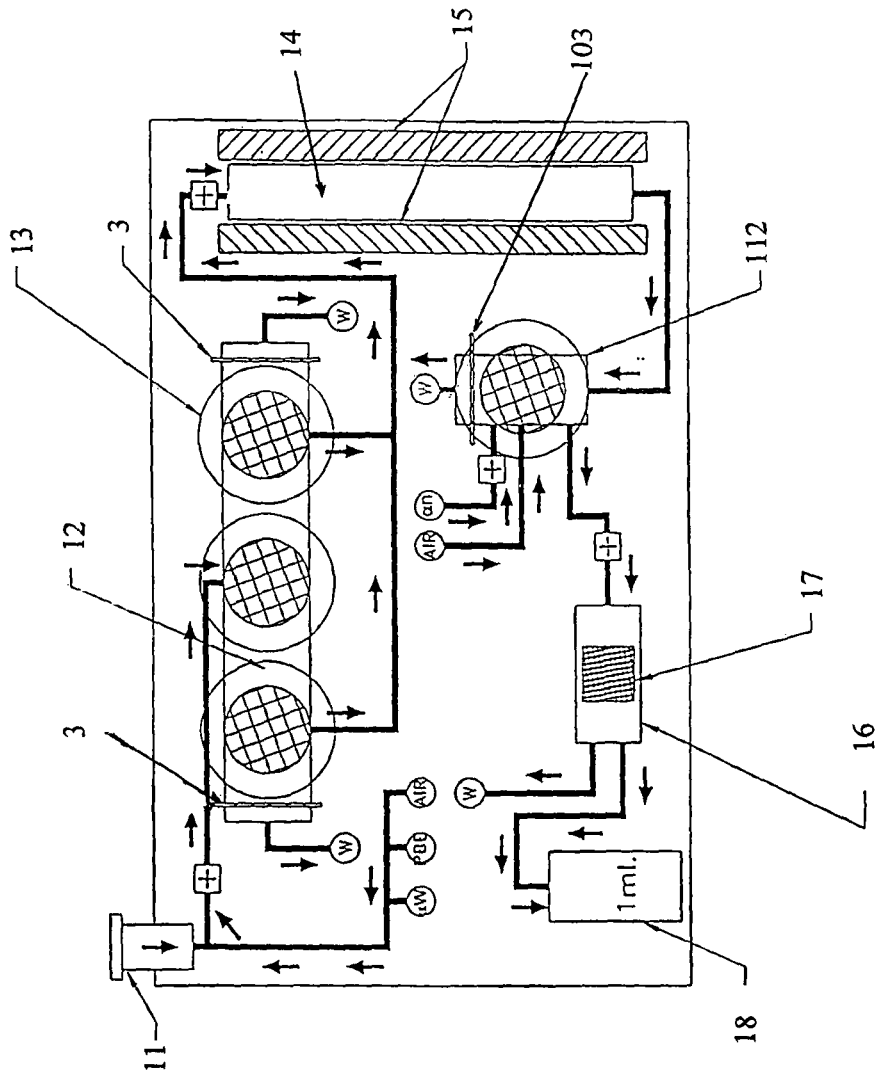
FIG. 6 is a diagram of an automated system of the present invention that comprises an inlet for the addition of a blood sample (11); a filtration chamber (12) that comprises acoustic mixing chips (13) and microfabricated filters (103); a magnetic capture column (14) having adjacent magnets (15); a mixing/filtration chamber (112); a magnetic separation chamber (16) comprising an electromagnetic chip (17), and a vessel for rare cell collection (18).

A filtration chamber of the present invention can comprise or engage any number of filters. In one preferred embodiment of the present invention, a filtration chamber comprises one filter (see, for example FIG. 5 and FIG. 14. In another preferred embodiment of the present invention, a filtration chamber comprises more than one filter, such as the chamber exemplified in FIG. 6 and FIG. 7. Various filter chamber configurations are possible. For example, it is within the scope of the present invention to have a filtration chamber in which one or more walls of the filter chamber comprises a microfabricated filter. It is also within the scope of the present invention to have a filtration chamber in which a filter chamber engages one or more filters. In this case, the filters can be permanently engaged with the chamber, or can be removable (for example, they can be inserted into slots or tracks provided on the chamber). A filter can be provided as a wall of a chamber, or internal to a chamber, and filters can optionally be provided in tandem for sequential filtering. Where filters are inserted into a chamber, they are inserted to form a tight seal with the walls of a chamber, such that during the filtration operation, fluid flow through the chamber (from one side of a filter to the other) must be through the pores of the filter.

In embodiments in which a filtration chamber of the present invention comprises one or more microfabricated filters that are internal to the chamber, the filter or filters can divide the chamber into subchambers. Where a filtration chamber comprises a single internal microfabricated filter, for example, the filtration chamber can comprise a prefiltration "antechamber", or where appropriate, "upper subchamber" and a "post-filtration subchamber", or, where appropriate, "lower subchamber". In other cases, a microfabricated filter can form a wall of a filtration chamber, and during filtration, filterable sample components exit the chamber via the filter.

In some preferred embodiments of the present invention, a filtration chamber of the present invention has at least one port that allows for the introduction of a sample into the chamber, and conduits can transport sample to and from a filtration chamber of the present invention. When fluid flow commences, sample components that flow through one or more filters can flow into one or more areas of the chamber and then out of the chamber through conduits, and, preferably but optionally, from the conduits into a vessel, such as a waste vessel. The filtration chamber can also optionally have one or more additional ports for the additions of one or more reagents, solutions, or buffers.

In some preferred embodiments, a filtration chamber of the present invention is part of a filtration unit in which valves control fluid flow through the chamber. For example, one preferred filtration unit of the present invention, depicted in FIG. 5, comprises a valve-controlled inlet for the addition of sample (valve A (6)), a valve connected to a conduit through which negative pressure is applied for the filtration of the sample (valve B (7)), and a valve controlling the flow of wash buffer into the filtration chamber for washing the chamber (valve C (8)). In some preferred embodiments of the present invention, a filtration unit can comprise valves that can optionally be under automatic control that allow sample to enter the chamber, waste to exit the chamber, and negative pressure to provide fluid flow for filtration.

In order to transfer a solution or supernatant to the filtration chamber, a needle (but not limited to stated object) can be used. A needle may be connected to the container (e.g. tubing or chamber) that can hold a volume. The needle may collect cells from a tube containing a solution and dispenses the solution into another chamber using a device to push or pull a solution (e.g. pump or syringe).

The chamber may include one or more surface contours to affect the flow of a sample, a solution such as wash or elution solution or both. For example contours may deflect, disperse or direct a sample to assist in the spreading of the sample along the chip. Alternatively, contours may deflect, disperse or direct a wash solution such that the wash solution washes the chamber or chip with greater efficiency. Such surface contours may be in any appropriate configuration. The contours may include surfaces that project generally toward the chip or may project generally away from the chip. They may generally encircle the chip. Contours may include but are not limited to projections, recessed portions, slots, deflection structures such as ball-like portions, bubbles (formed from e.g. air, detergent, or polymers), and the like. Contours such as two or more slots may be configured generally parallel to one another yet generally angled when viewing the chamber upright to direct flow in a generally spiraled path.

In a preferred embodiment of the present invention, a filtration chamber of, for example, approximately one centimeter by one centimeter by 0.2 to ten centimeters in dimensions can have one or more filters comprising from four to 1,000,000 slots, preferably from 100 to 250,000 slots. In this preferred embodiment, the slots are preferably of rectangular shape, with a slot length of from about 0.1 to about 1,000 microns, and slot width is preferably from about 0.1 to about 100 microns, depending on the application.

Figure 7:
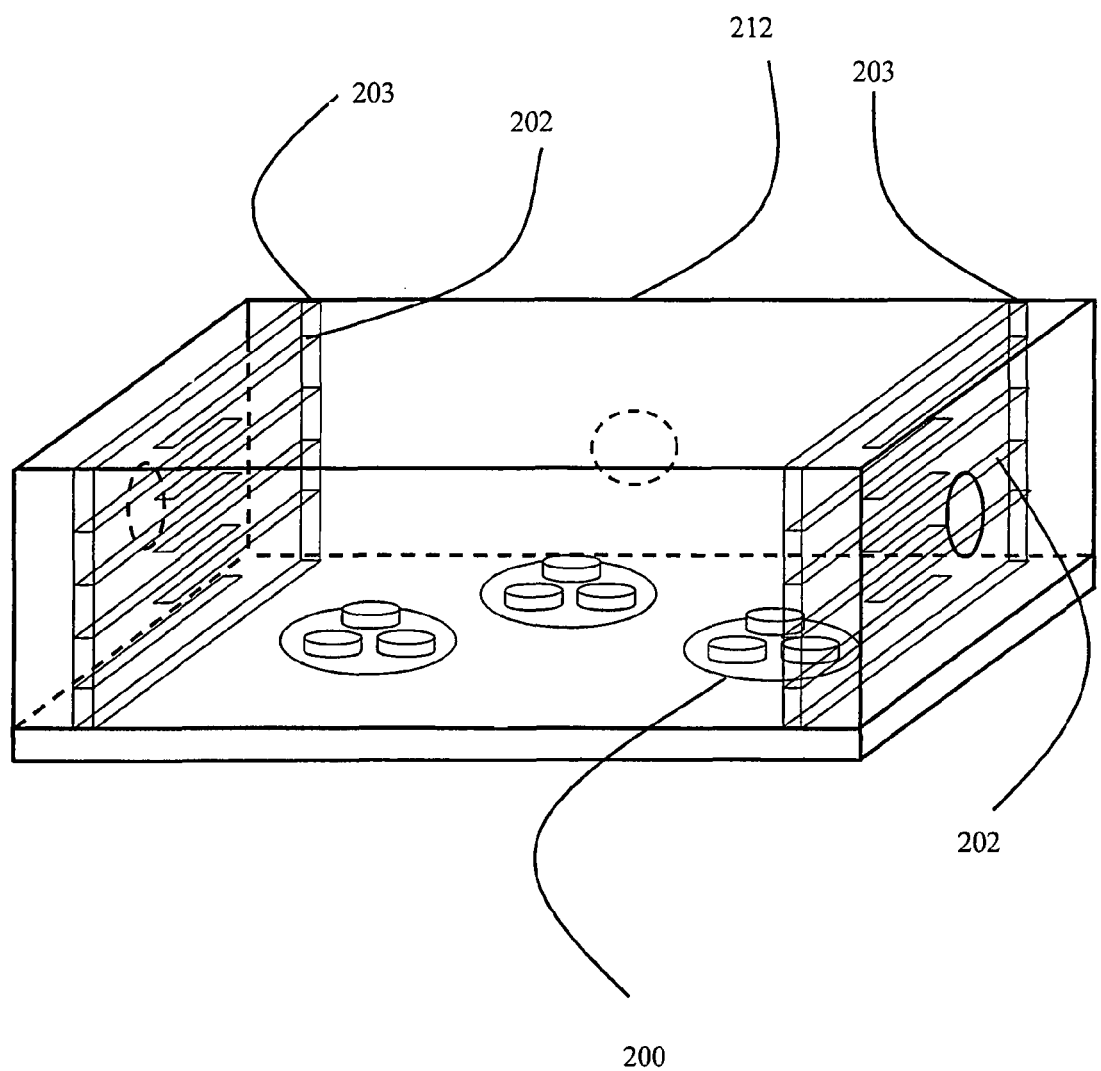
FIG. 7 depicts a three-dimensional perspective view of a filtration chamber of the present invention that has two filters (203) that comprise slots (202) and a chip having acoustic elements (200)(the acoustic elements may not be visible on the chip surface, but are shown here for illustrative purposes). In this simplified depiction, the width of the slots is not shown.
Figure 8:
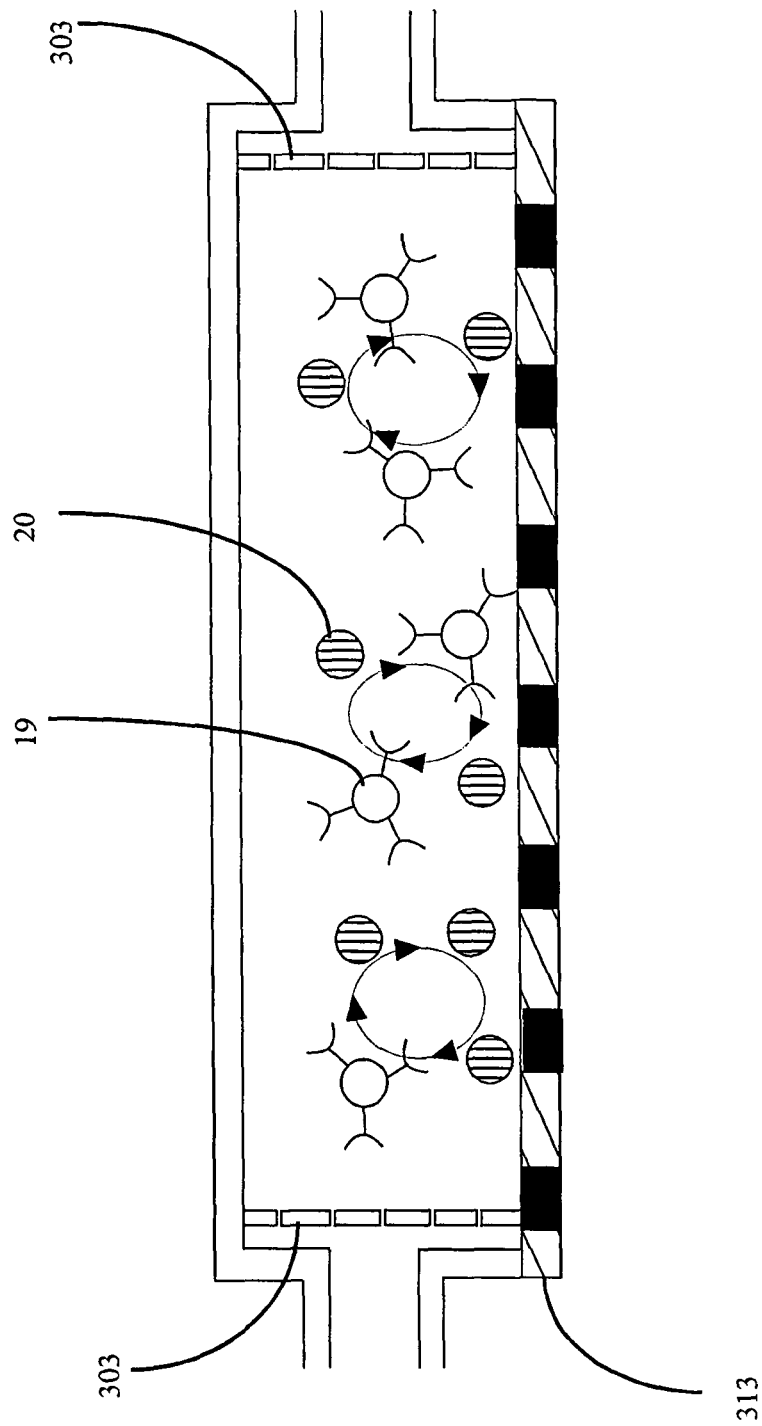
FIG. 8 depicts a cross-sectional view of a filtration chamber of the present invention having two filters (303) after filtering has been completed, and after the addition of magnetic beads (19) to a sample comprising target cells (20). The acoustic elements are turned on during a mixing operation.
Figure 9:
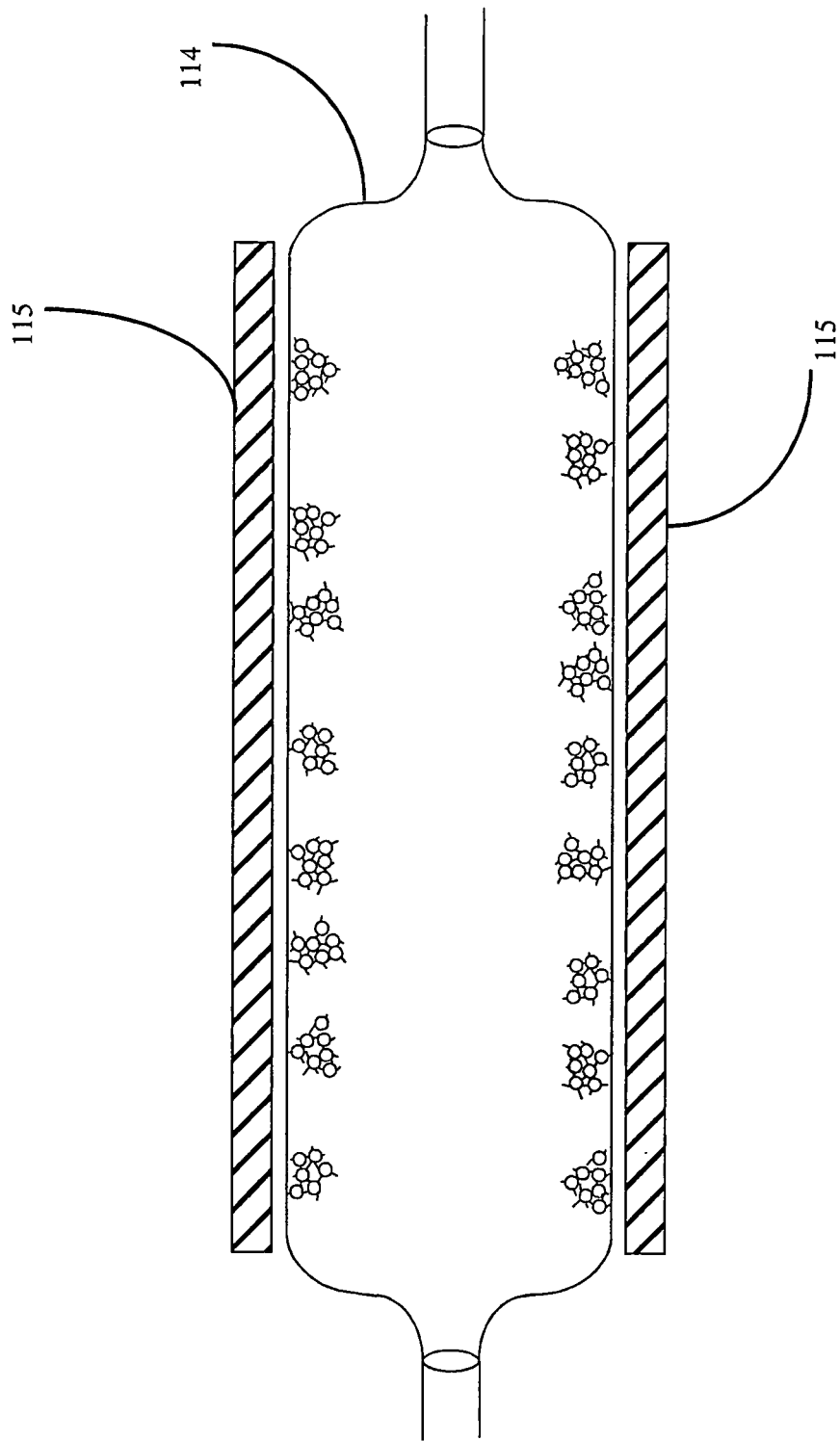
FIG. 9 depicts a cross-sectional view of a feature of an automated system of the present invention: a magnetic capture column (114). Magnets (115) are positioned adjacent to the separation column.
Figure 10:
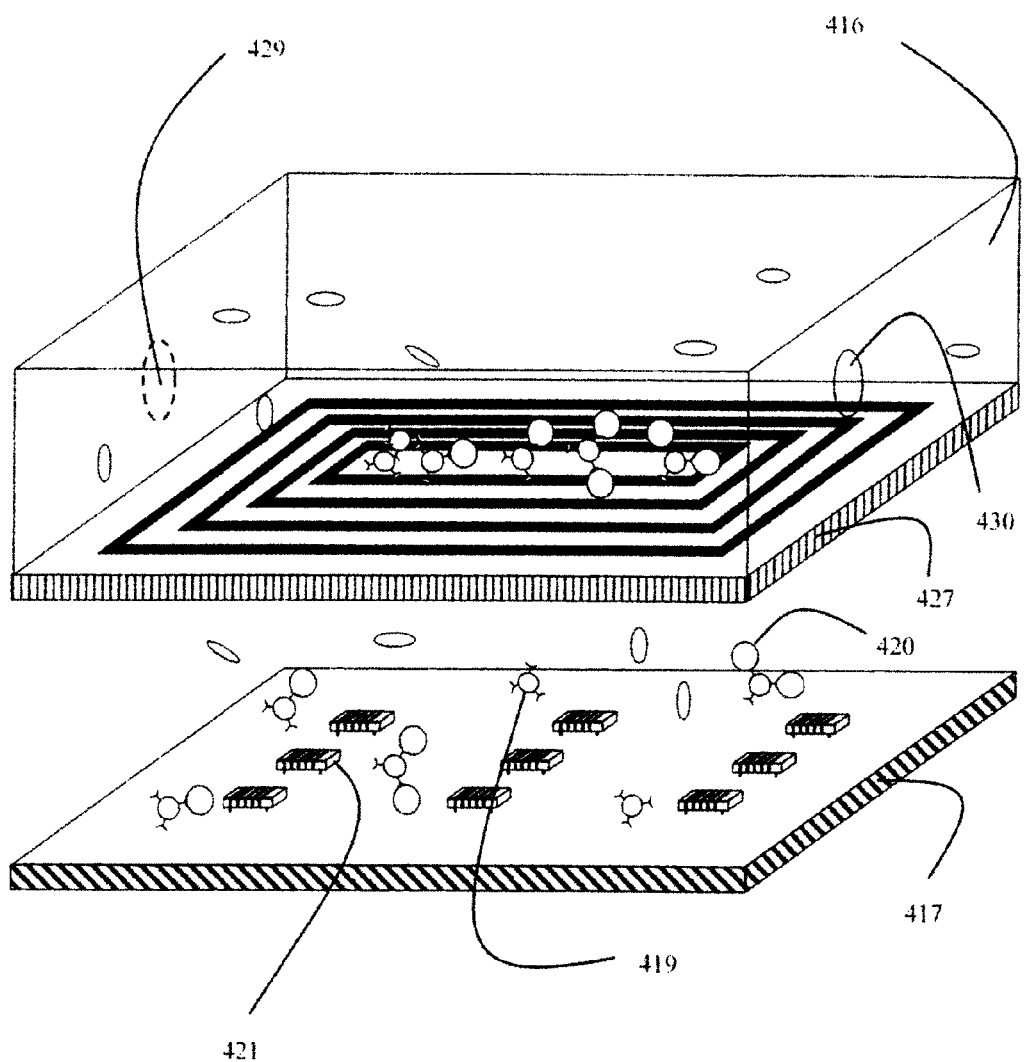
FIG. 10 depicts a three-dimensional perspective view of a chamber (416) of an automated system of the present invention that comprises a multiple force chip that can separate rare cells from a fluid sample. The chamber has an inlet (429) and an outlet (430) for fluid flow through the chamber. A cut-away view shows the chip has an electrode layer (427) that comprises an electrode array for dielectrophoretic separation and an electromagnetic layer (417) that comprises electromagnetic units (421) an electrode array on another layer. Target cells (420) are bound to magnetic beads (419) for electromagnetic capture.
Figure 11:
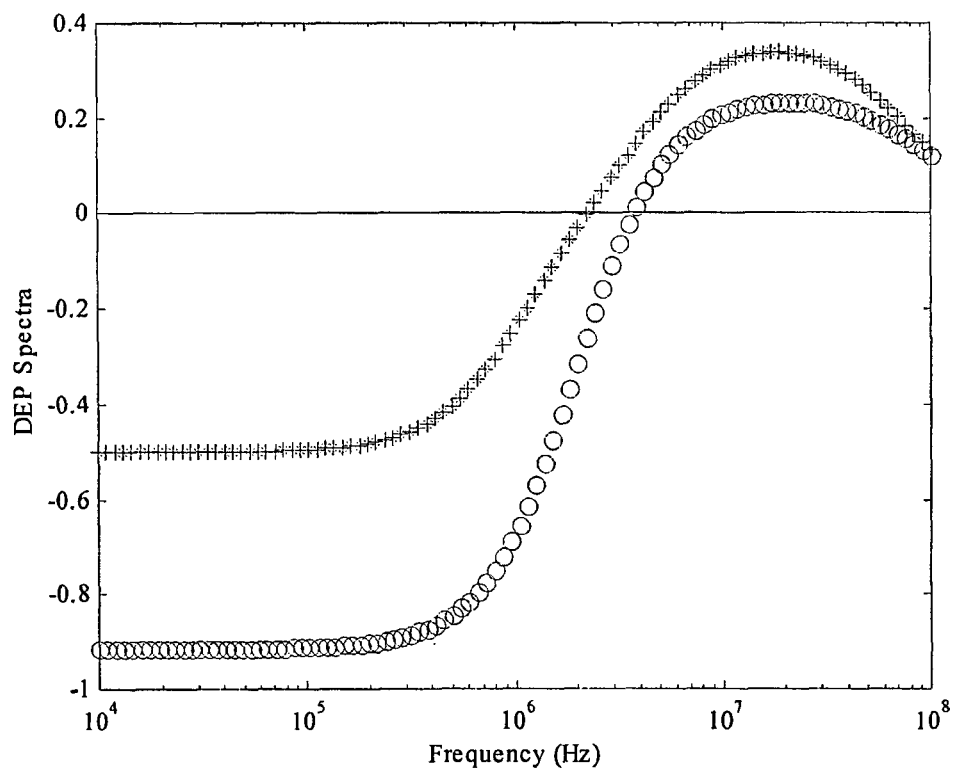
FIG. 11 shows a graph illustrating the theoretical comparison between the DEP spectra for an nRBC (Xs) and a RBC (circles) when the cells are suspended in a medium of electrical conductivity of 0.2 S/m.
Figure 12:
FIG. 12 shows FISH analysis of nucleated fetal cells isolated using the methods of the present invention using a Y chromosome marker that has detected a male fetal cell in a maternal blood sample.
Figure 14:
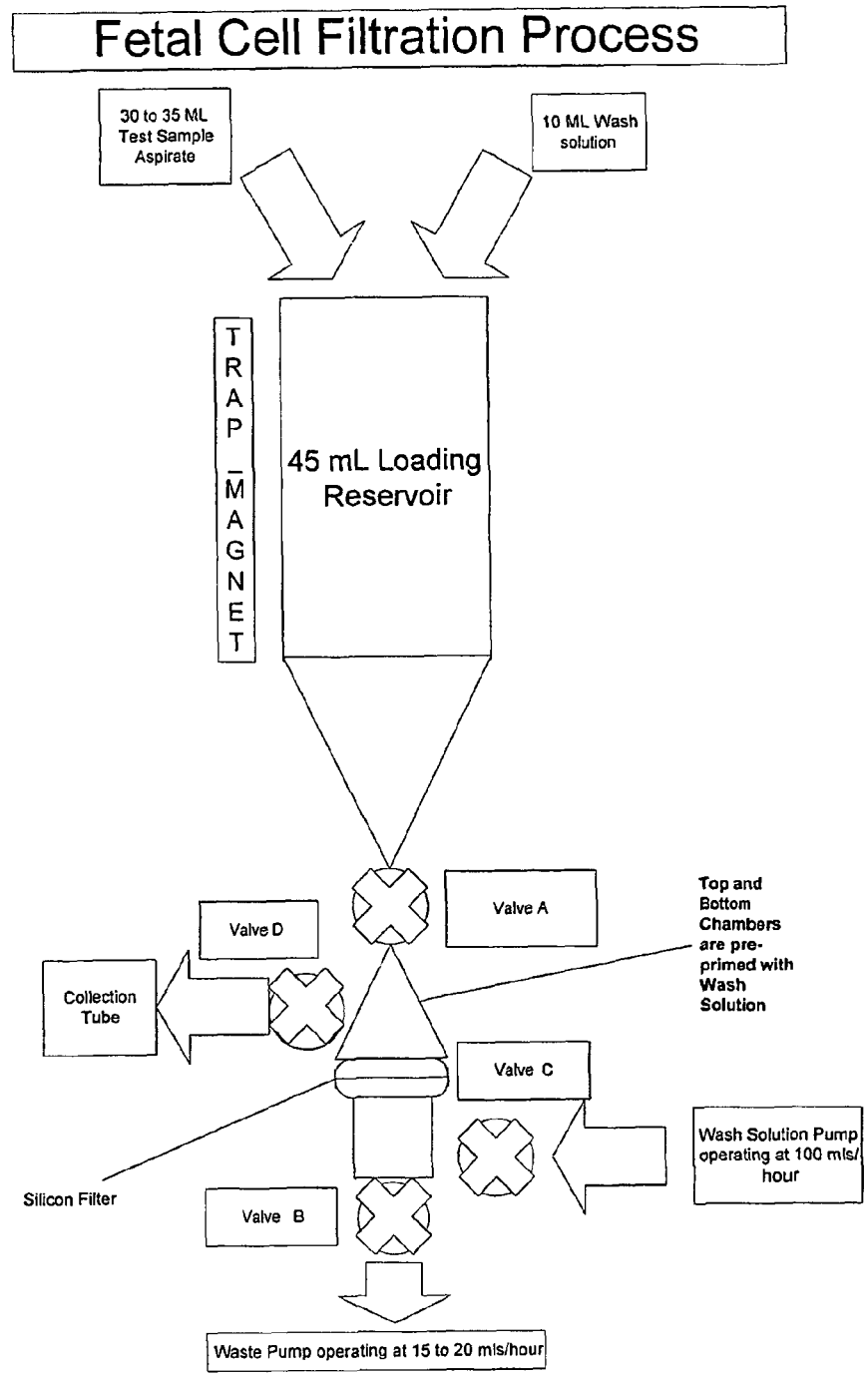
FIG. 14 is a schematic depiction of a filtration unit of the present invention.
Figure 15:
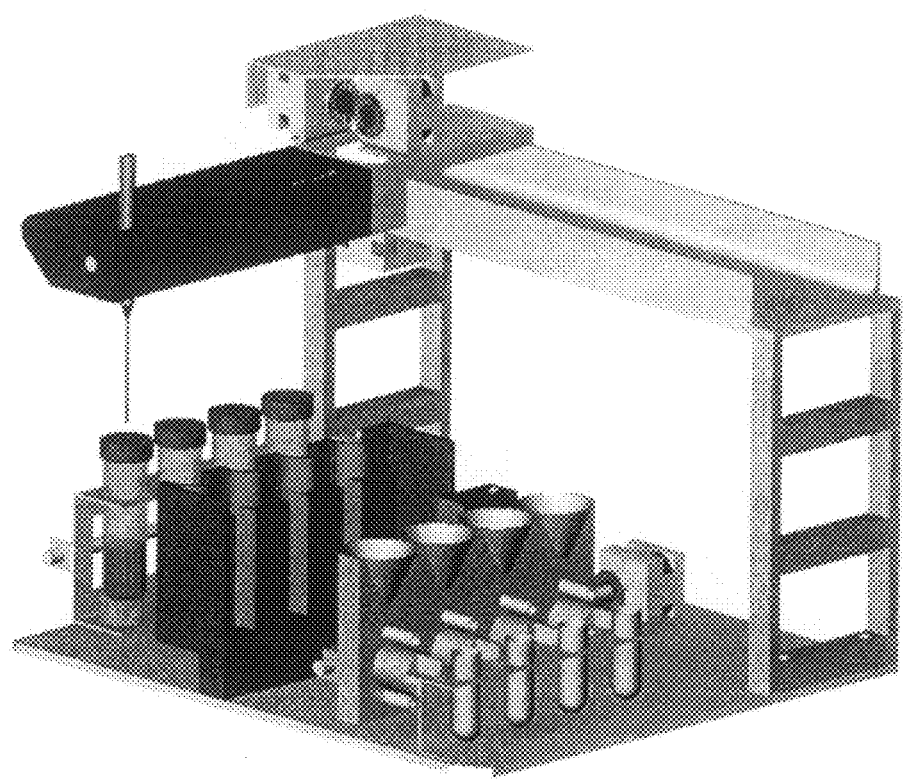
FIG. 15 shows a model of an automated system of the present invention.
Figure 16A:
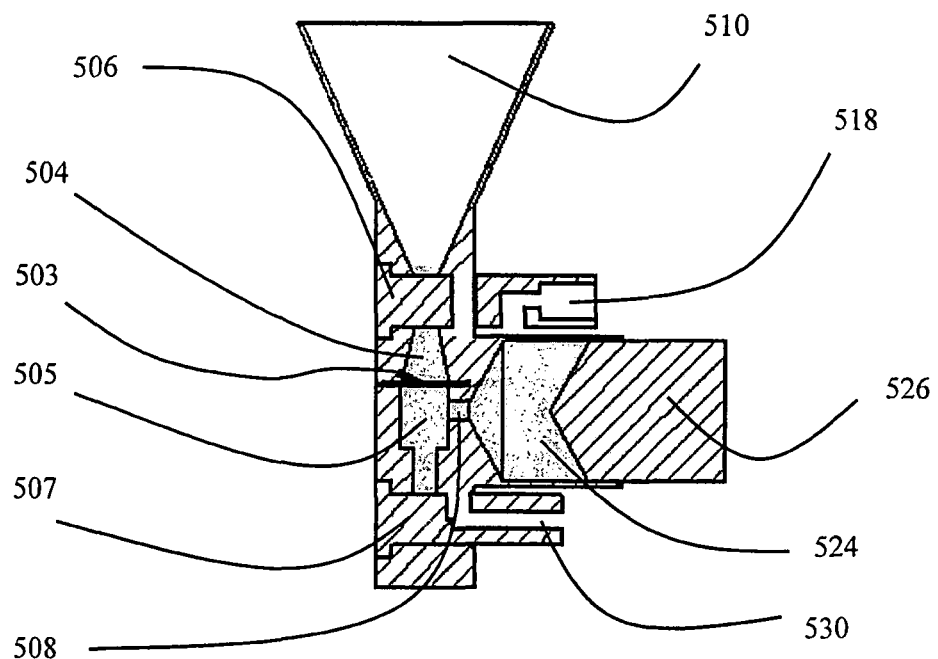
FIG. 16 depicts the filtration process of an automated system of the present invention. A) shows the filtration unit having a loading reservoir (510) connected through a valve (506) to a filtration chamber that comprises an antechamber (504) separated from a post-filtration subchamber (505) by a microfabricated filter (503). A wash pump (526) is connected to the lower chamber through a valve (508) for pumping wash buffer (524) through the lower subchamber. Another valve (507) leads to another negative pressure pump used to promote fluid flow through the filtration chamber and out through an exit conduit (530). A collection vessel (518) can reversibly engage the upper chamber (504). B) shows a blood sample (525) loaded into the loading reservoir (510). In C) the valve (507) that leads to a negative pressure pump used to promote fluid flow through the filtration chamber is open, and D) and E) show the blood sample being filtered through the chamber. In F) wash buffer introduced through the loading reservoir is filtered through the chamber. In G), valve (508) is open, while the loading reservoir valve (506) is closed, and wash buffer is pumped from the wash pump (526) into the lower chamber. In H) the filtration valve (507) and wash pump valve (508) are closed and in I) and J) the chamber is rotated 90 degrees. K) shows the collection vessel (518) engaging the antechamber (504) so that fluid flow generated by the wash pump (526) causes rare target cells (520) retained in the antechamber to flow into the collection tube.
Figure 16B:
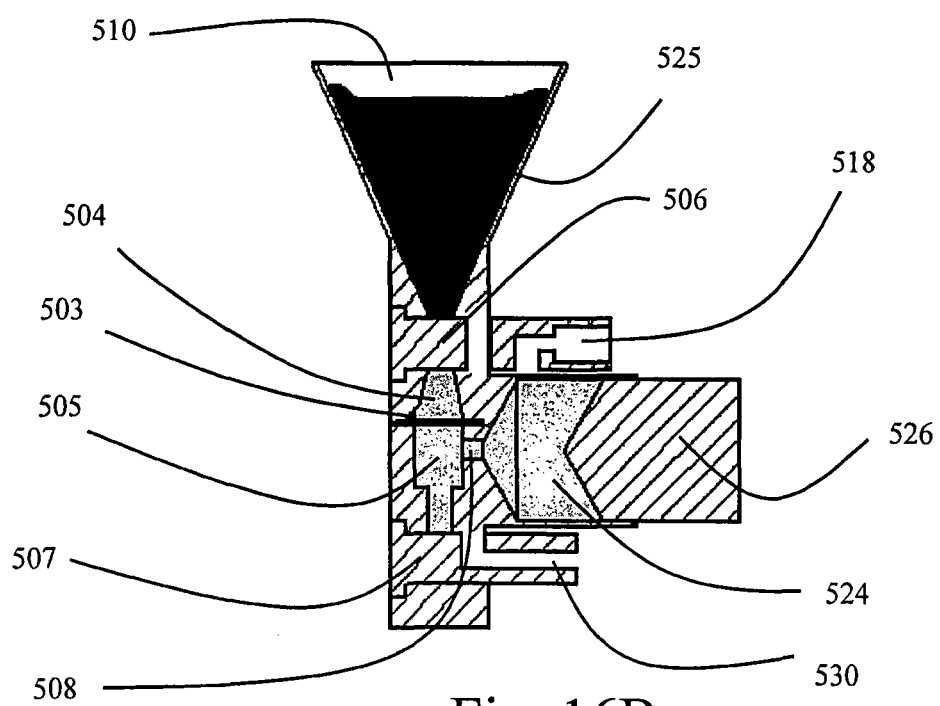
Figure 16C:
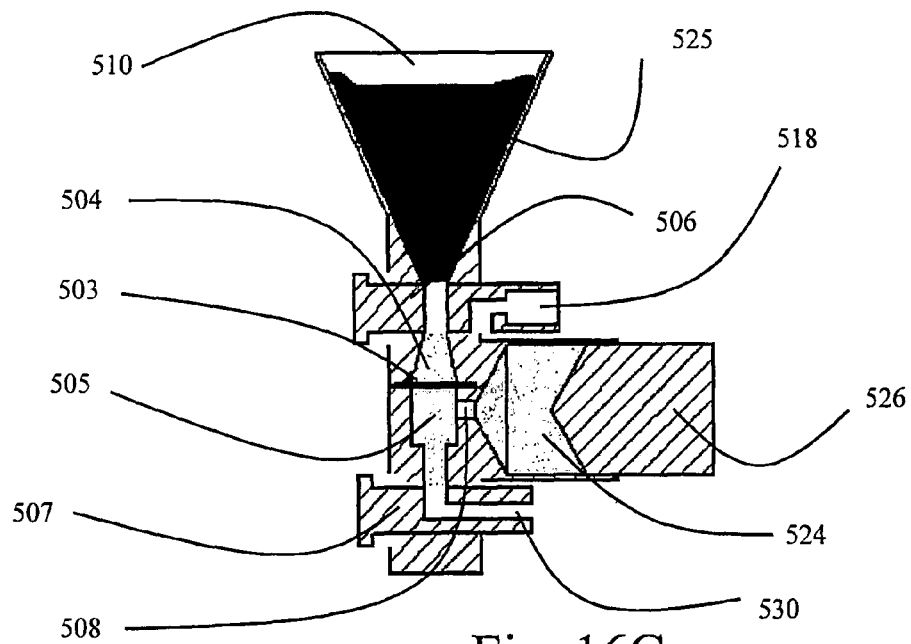
Figure 16D:
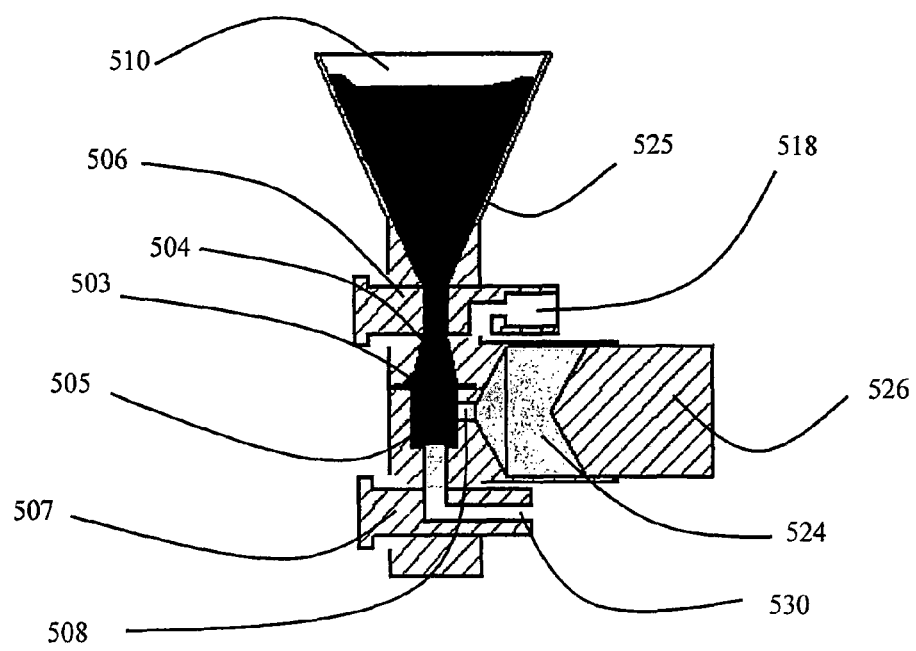
Figure 16E:
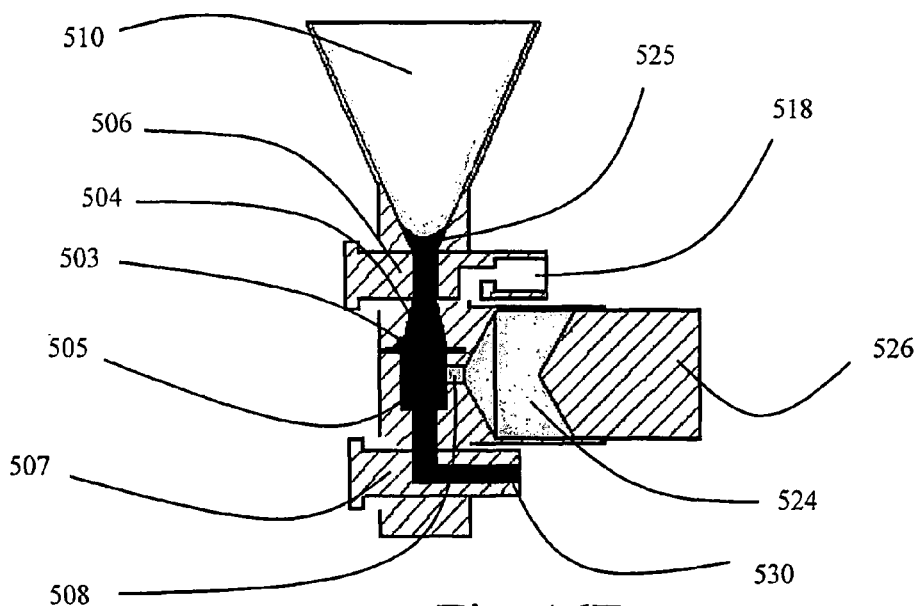
Figure 16F:
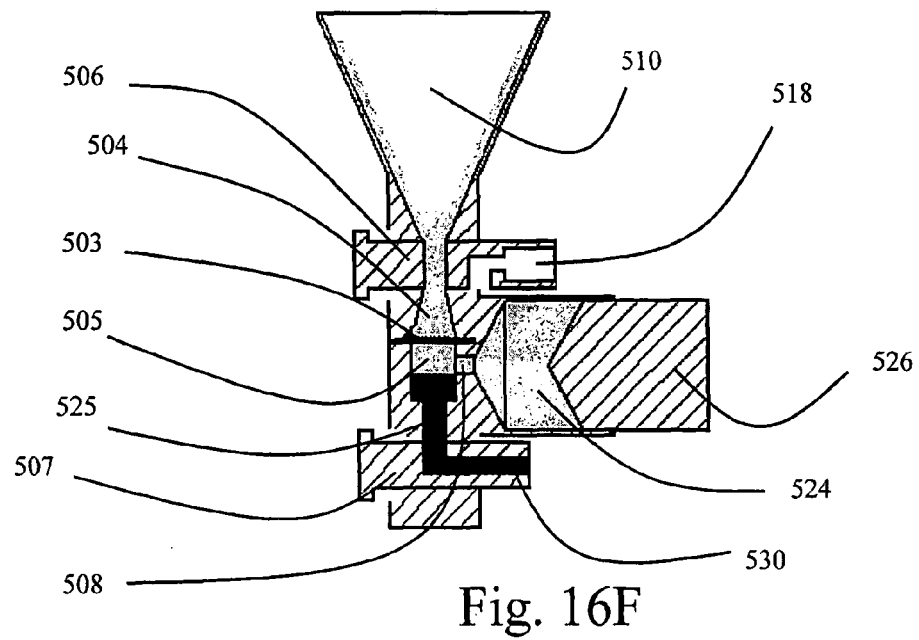
Figure 16G:
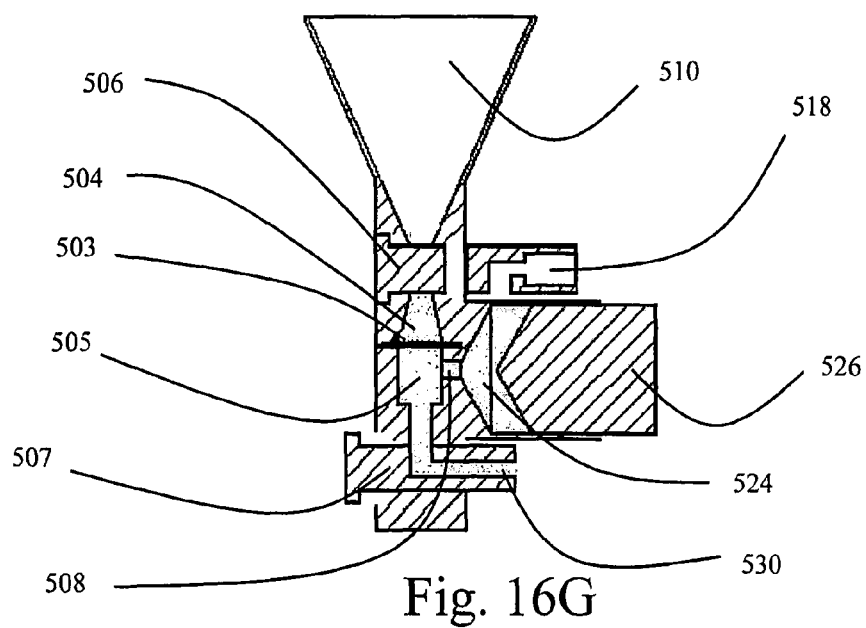
Figure 16H:
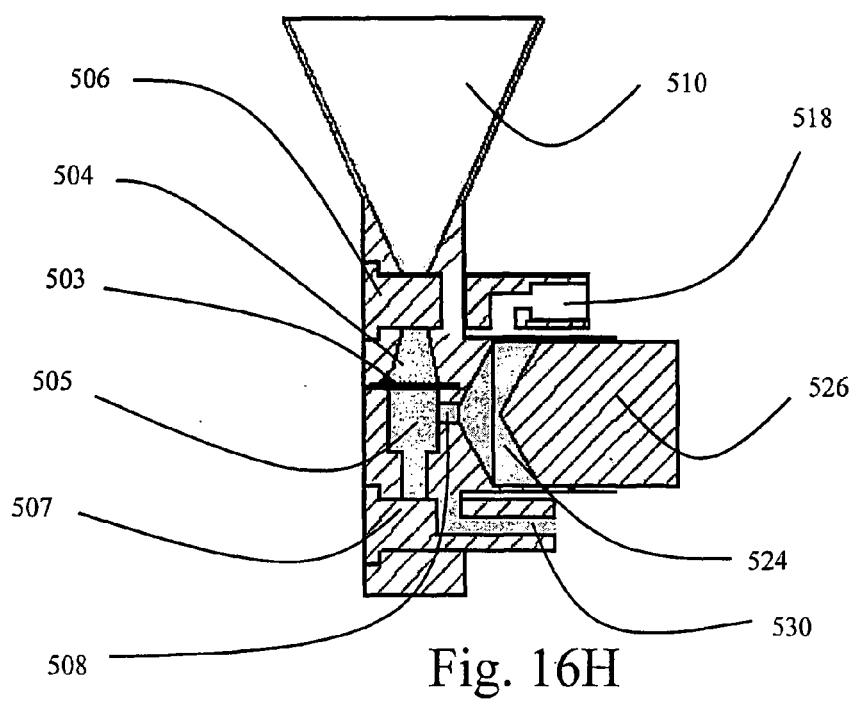
Figure 16I:
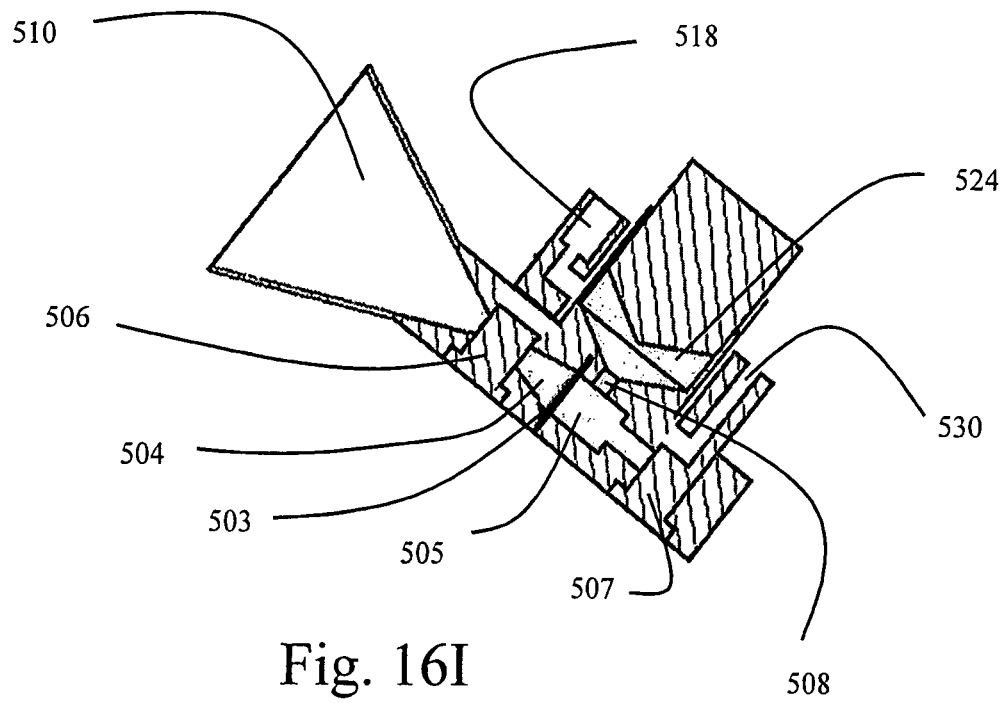
Figure 16J:
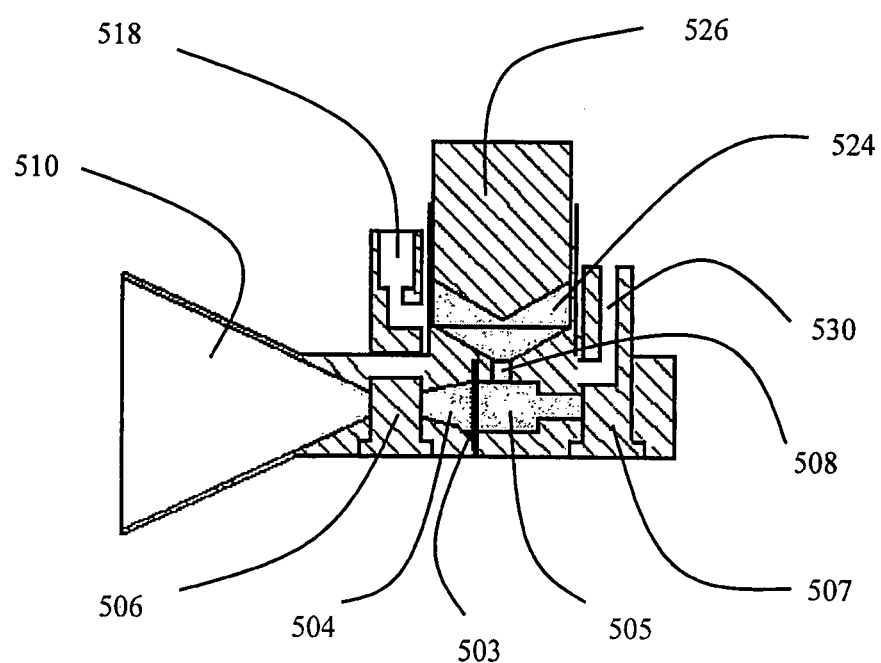
Figure 16K:
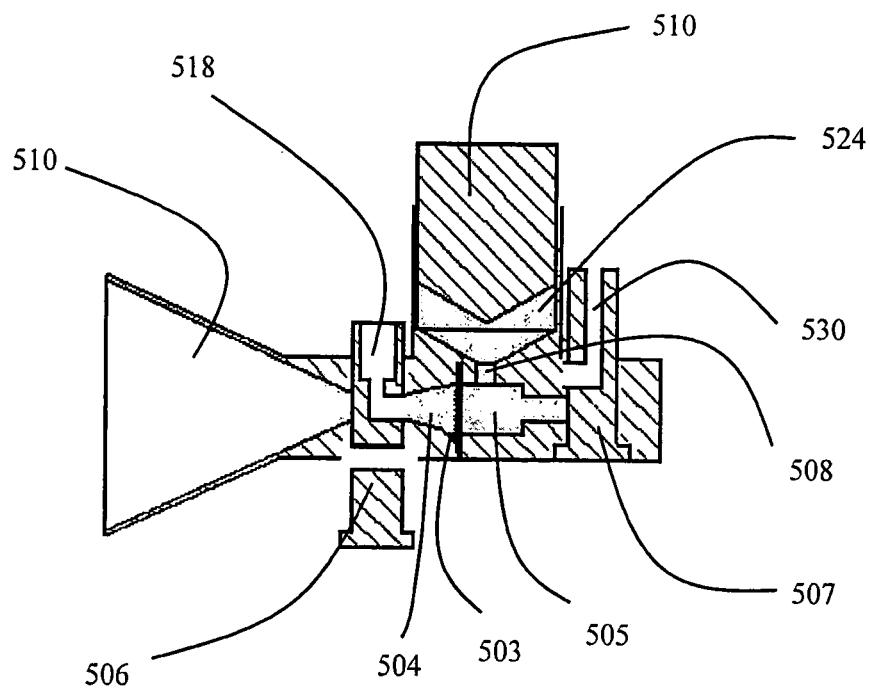
Figure 16L:
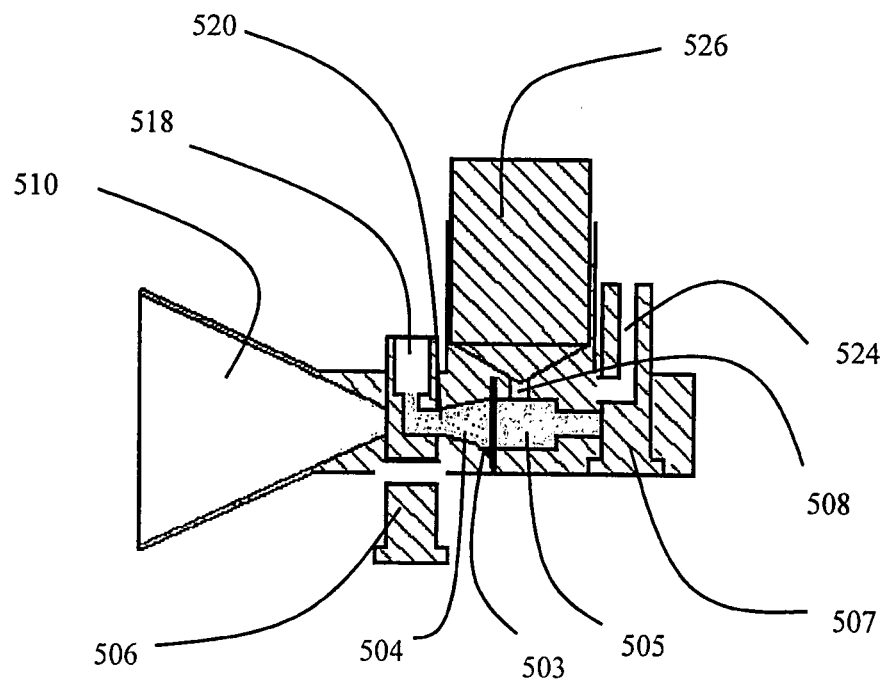
Figure 16M:
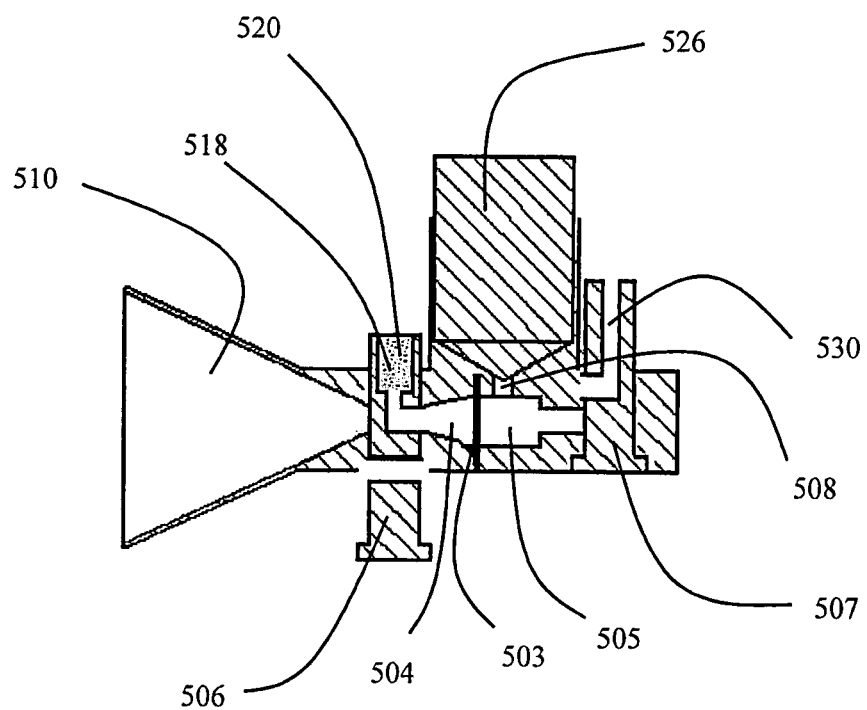
Figure 17A:
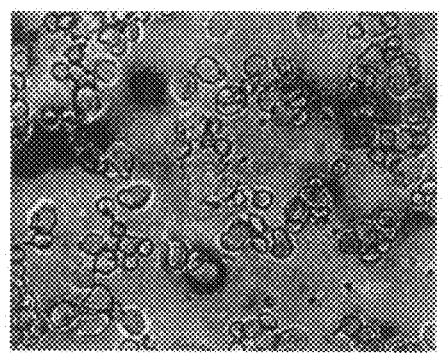
FIG. 17 depicts a fluorescently labeled breast cancer cell in a background of unlabeled blood cells after enrichment by microfiltration. A) phase contrast microscopy of filtered blood sample. B) fluorescence microscopy of the same field shown in A.
Figure 17B:
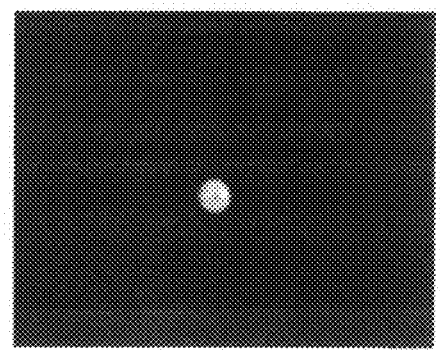
Figure 18A:
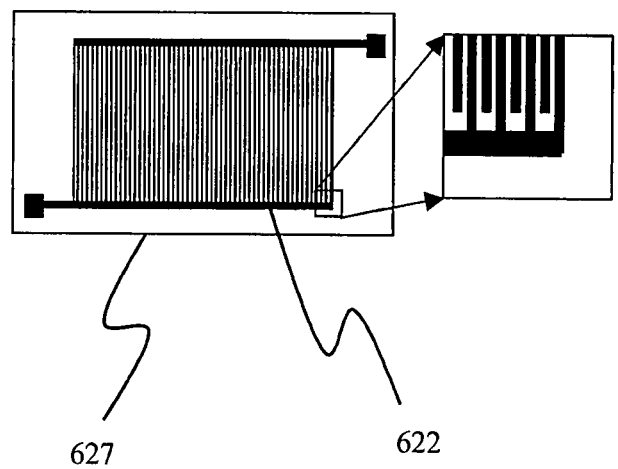
FIG. 18 depicts two configurations of dielectrophoresis chips of the present invention. A) chip with interdigitated electrode geometry; B) chip with castellated electrode geometry.
Figure 18B:
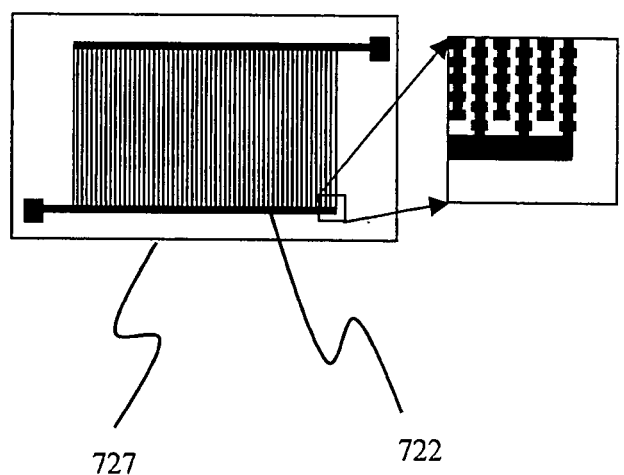
Figures 19A, 19B:
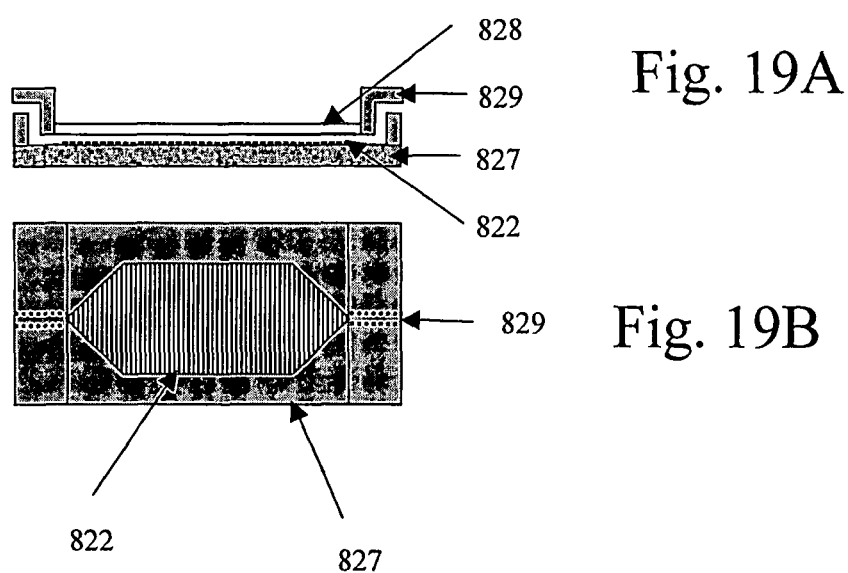
FIG. 19 depicts a separation chamber of the present invention comprising a dielectrophoresis chip. A) Cross-sectional view of the chamber, B) top view showing the chip.
Figure 20:
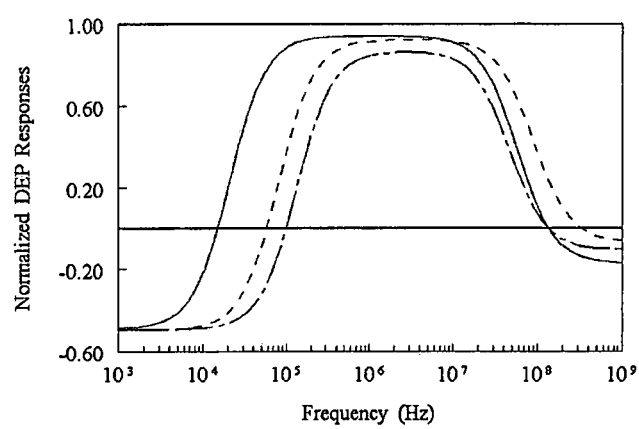
FIG. 20 is a graph illustrating the theoretical comparison between the DEP spectra for MDA231 cancer cells (solid line) T-lymphocytes (dashed line) and erythrocytes (small dashes) when the cells are suspended in a medium of electrical conductivity of 10 mS/m.
Figure 21A:
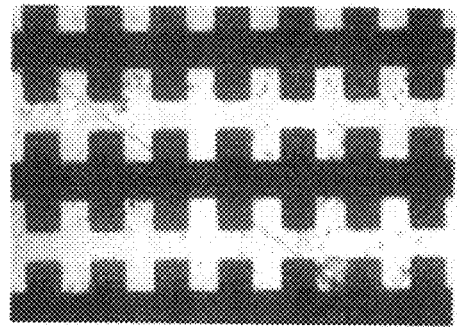
FIG. 21 depicts breast cancer cells from a spiked blood sample retained on electrodes of a dielectrophoresis chip.
Figure 21B:
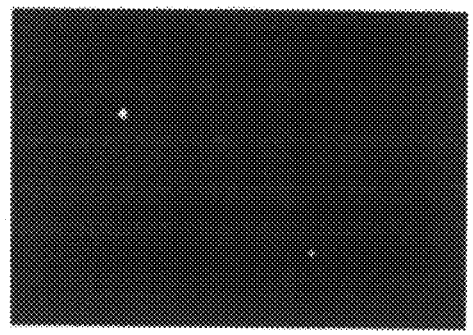

Preferably, slots can allow for the passage of mature red blood cells (lacking nuclei) through the channels and thus out of the chamber, while not or minimally allowing cells having a greater diameter or shape (for example but not limited to, nucleated cells such as white blood cells and nucleated red blood cells) to exit the chamber. A filtration chamber that can allow the removal of red blood cells by fluid flow through the chamber, while retaining other cells of a blood sample, is illustrated in FIG. 7, FIG. 14, and FIG. 16. For example, for removing matured red blood cells from nucleated RBCs and white blood cells, slot widths between 2.5 and 6.0 microns, more preferably between 2.5 and 4.0 microns, could be used. Slot length could vary between, for example, 20 and 200 microns. Slot depth (i.e., filter membrane thickness) can vary between 40 and 100 microns. The slot width between 2.0 and 4.0 microns would allow the double-discoid-shaped RBCs to go through the slots while primarily retaining the nucleated RBCs and WBCs with diameters or shapes larger than 7 micron.

Filtration Chamber Comprising Active Chip

A filtration chamber can also preferably comprise or engage at least a portion of at least one active chip, where an active chip is a chip that uses applied physical forces to promote, enhance, or facilitate processing or desired biochemical reactions of a sample, or and to decrease or reduce any undesired effects that might otherwise occur to or in a sample. An active chip of a filtration chamber of the present invention preferably comprises acoustic elements, electrodes, or even electromagnetic elements. An active chip can be used to transmit a physical force that can prevent clogging of the slots or around the structures used to create a filter (for example, blocks, dams, or channels, slots etched into and through the filter substrate) by components of the sample that are too large to go through the pores or slots or openings, or become aggregated at the pores or slots or openings. For example, when an electric signal is applied, acoustic elements can cause mixing of the components within the chamber, thereby dislodging nonfilterable components from the slots or pores. In an alternative embodiment, a pattern of electrodes on a chip can provide negative dielectrophoresis of sample components to move the nonfilterable components from the vicinity of the slots, channels, or openings around structures and allow access of filterable sample components to the slots or openings. Example of such electrode arrays fabricated onto a filter under a different operating mechanism of "dielectrophoretic-base selective retention" have been described in "Novel dielectrophoresis-based device of the selective retention of viable cells in cell culture media" by Docoslis et al., in Biotechnology and Bioengineering, Vol. 54, No. 3, pages 239-250, 1997, herein incorporated by reference and in the U.S. Pat. No. 5,626,734, issued to Docoslis et al on May 7, 1997, herein incorporated by reference. Active chips, including chips that can be used to mix samples by acoustic forces and chips that can be used to move moieties, including sample components, by dielectrophoretic forces, are described in U.S. application Ser. No. 09/636,104, filed Aug. 10, 2000, entitled "Methods for Manipulating Moieties in Microfluidic Systems", U.S. provisional application 60/239,299, entitled "An Integrated Biochip System for Sample Preparation and Analysis", filed Oct. 10, 2000, and U.S. application Ser. No. 09/686,737, filed Oct. 10, 2000 entitled "Compositions and Methods for Separation of Moieties on Chips", all herein incorporated by reference.

The incorporation of electrodes that can be used for traveling wave dielectrophoresis on a filter of the present invention, as well as principles of dielectrophoresis and traveling wave dielectrophoresis, has been described herein in a previous description of microfabricated filters. Electrodes can also be incorporated onto active chips that are used in filtration chambers of the present invention to improve filtration efficiency.

A filtration chamber can also comprise a chip that comprises electromagnetic elements. Such electromagnetic elements can be used for the capture of sample components before or, preferably, after, filtering of the sample. Sample components can be captured after being bound to magnetic beads. The captured sample components can be either undesirable components to be retained in the chamber after the sample containing desirable components has already been removed from the chamber, or the captured sample components can be desirable components captured in the chamber after filtration.

An acoustic force chip can engage or be part of a filtration chamber, or one or more acoustic elements can be provided on one or more walls of a filtration chamber. Mixing of a sample by the activation of the acoustic force chip can occur during the filtration procedure. Preferably, a power supply is used to transmit an electric signal to the acoustic elements of one or more acoustic chips or one or more acoustic elements on one or more walls or a chamber. One or more acoustic elements can be active continuously throughout the filtration procedure, or can be activated for intervals (pulses) during the filtration procedure.

Sample components and, optionally, solutions or reagents added to the sample can be mixed by acoustic forces that act on both the fluid and the moieties, including, but not limited to, molecules, complexes, cells, and microparticles, in the chamber. Acoustic forces can cause mixing by acoustic streaming of fluid that occurs when acoustic elements, when energized by electrical signals generate mechanical vibrations that are transmitted into and through the fluid. In addition, acoustic energy can cause movement of sample components and/or reagents by generating acoustic waves that generate acoustic radiation forces on the sample components (moieties) or reagents themselves.

The following discussion and references can provide a framework for the design and use of acoustic elements to provide a mixing function:

Acoustic force refers to the force that is generated on moieties, e.g., particles and/or molecules, by an acoustic wave field. (It may also be termed acoustic radiation forces.) The acoustic forces can be used for manipulating, e.g., trapping, moving, directing, handling, mixing, particles in fluid. The use of the acoustic force in a standing ultrasound wave for particle manipulation has been demonstrated for concentrating erythrocytes (Yasuda et al., *J. Acoust. Soc. Am.,* 102(1): 642-645 (1997)), focusing micron-size polystyrene beads (0.3 to 10 micron in diameter, Yasuda and Kamakura, *Appl. Phys. Lett,* 71(13):1771-1773 (1997)), concentrating DNA molecules (Yasuda et al., *J. Acoust. Soc. Am.,* 99(2):1248-1251, (1996)), batch and semicontinuous aggregation and sedimentation of cells (Pui et al., *Biotechnol. Prog.,* 11:146-152 (1995)). By competing electrostatic and acoustic radiation forces, separation of polystyrene beads of different size and charges have been reported (Yasuda et al., *J. Acoust. Soc. Am.,* 99(4):1965-1970 (1996); and Yasuda et al., *Jpn. J. Appl. Phys.,* 35(1):3295-3299 (1996)). Furthermore, little or no damage or harming effect was observed when acoustic radiation force was used to manipulate mammalian cells, as characterized in terms of ion leakage (for erythrocytes, Yasuda et al., *J. Acoust. Soc. Am.,* 102(1):642-645 (1997)) or antibody production (for hybridoma cells, Pui et al., *Biotechnol. Prog.,* 11:146-152 (1995)).

An acoustic wave can be established by an acoustic transducer, e.g., piezoelectric ceramics such as PZT material. The piezoelectric transducers are made from "piezoelectric materials" that produce an electric field when exposed to a change in dimension caused by an imposed mechanical force (piezoelectric or generator effect). Conversely, an applied electric field will produce a mechanical stress (electrostrictive or motor effect) in the materials. They transform energy from mechanical to electrical and vice-versa. When AC voltages are applied to the piezoelectric transducers, the vibration occurs to the transducers and such vibration can be coupled into a fluid that is placed in the chamber comprising the piezoelectric transducers.

An acoustic chip can comprise acoustic transducers so that when AC signals at appropriate frequencies are applied to the electrodes on the acoustic transducers, the alternating mechanical stress is produced within the piezoelectric materials and is transmitted into the liquid solutions in the chamber. In a situation where the chamber is set up so that a standing acoustic wave is established along the direction (e.g.: z-axis) of wave propagation and reflection, the standing wave spatially varying along the z axis in a fluid can be expressed as:

$$\Delta p(z) = p_0 \sin(kz) \cos(\omega t)$$

where $\Delta p$ is acoustic pressure at z, $p_0$ is the acoustic pressure amplitude, k is the wave number ($2\pi/\lambda$, where $\lambda$ is the wavelength), z is the distance from the pressure node, $\omega$ is the angular frequency, and t is the time. In one example, the standing-wave acoustic field may be generated by the superimposition of an acoustic wave generated from an acoustic transducer that forms a major surface of a chamber and the reflective wave from another major surface of the chamber that is positioned in parallel with the acoustic transducer and reflects the acoustic wave from the transducer. According to the theory developed by Yosioka and Kawasima (Acoustic Radiation Pressure on a Compressible Sphere by Yosioka K. and Kawasima Y. in Acustica, Volume 5, pages 167-173, 1955), the acoustic force $Fn_{acoustic}$ acting on a spherical particle in the stationary standing wave field is given by $$F_{acoustic} = -\frac{4\pi}{3} r^3 k E_{acoustic} A \sin(2kz)$$

where r is the particle radius, $E_{acoustic}$ is the average acoustic energy density, A is a constant given by $$A = \frac{5\rho_p - 2\rho_m}{2\rho_p + \rho_m} - \frac{\gamma_p}{\gamma_m}$$

where $\rho_m$ and $\rho_p$ are the density of the particle and the medium, $\gamma_m$ and $\gamma_p$ are the compressibility of the particle and medium, respectively. The compressibility of a material is the product of the density of the material and the velocity of acoustic-wave in the material. The compressibility is sometimes termed acoustic impedance. A is termed as the acoustic-polarization-factor.

When A>0, the particle moves towards the pressure node (z=0) of the standing wave.

When A<0, the particle moves away from the pressure node.

The acoustic radiation forces acting on particles depend on acoustic energy density distribution and on particle density and compressibility. Particles having different density and compressibility will experience different acoustic-radiation-forces when they are placed into the same standing acoustic wave field. For example, the acoustic radiation force acting on a particle of 10 micron in diameter can vary somewhere between <0.01 and >1000 pN, depending on the established acoustic energy density distribution.

The above analysis considers the acoustic radiation forces exerted on particles in a standing acoustic wave. Further analysis may be extended to the case of the acoustic radiation forces exerted on particles in a traveling-wave case. Generally, an acoustic wave field may consist of both standing and traveling-wave components. In such cases, particles in the chamber will experience acoustic radiation forces in the form other than those described by above equations. The following papers provide detailed analysis of acoustic radiation forces on spherical particles by traveling acoustic wave and standing acoustic waves: "Acoustic Radiation Pressure on a Compressible Sphere" by Yosioka K. and Kawasima Y. in Acustica, Volume 5, pages 167-173, 1955; and "Acoustic-Radiation force on a solid elastic sphere" by Hasegawa T. and Yosioka K. in Journal of Acoustic Society of America.

The acoustic radiation forces on particles may also be generated by various special cases of acoustic waves. For example, acoustic forces may be produced by a focused beam ("Acoustic radiation force on a small compressible sphere in a focused beam" by Wu and Du, *J. Acoust. Soc. Am.*, 87:997-1003 (1990)), or by acoustic tweezers ("Acoustic tweezers" by Wu *J. Acoust. Soc. Am.*, 89:2140-2143 (1991)).

Acoustic wave field established in a fluid can also induce a time-independent fluid flow, as termed acoustic streaming. Such fluid flow may also be utilized in biochip applications or microfluidic applications for transporting or pumping fluids. Furthermore, such acoustic-wave fluid flow may be exploited for manipulating molecules or particles in fluids. The acoustic streaming depends on acoustic field distributions and on fluid properties ("Nonlinear phenomena" by Rooney J. A. in "Methods of Experimental Physics: Ultrasonics, Editor: P. D. Edmonds", Chapter 6.4, pages 319-327, Academic Press, 1981; "Acoustic Streaming" by Nyborg W. L. M. in "Physical Acoustics, Vol. II-Part B, Properties of Polymers and Nonlinear Acoustics, Chapter 11, pages 265-330).

Thus, one or more active chips, such as one or more acoustic force chips, can also be used to promote mixing of reagents, solutions, or buffers, that can be added to a filtration chamber, before, during, or after the addition of a sample and the filtration process. For example, reagents, such as, but not limited to specific binding members that can aid in the removal of undesirable sample components, or in the capture of desirable sample components, can be added to a filtration chamber after the filtration process has been completed and the conduits have been closed off. The acoustic elements of the active chip can be used to promote mixing of one or more specific binding members with the sample whose volume has been reduced by filtration. One example is the mixing of sample components with magnetic beads that comprise antibodies that can bind particular cell types (for example, white blood cells, or fetal nucleated red blood cells) within the sample. The magnetic beads can be used to selectively remove or separate (capture) undesirable or desirable sample components, respectively, in subsequent steps of a method of the present invention. The acoustic elements can be activated for a continuous mixing period, or in pulses.

II. Method of Enriching Rare Cells of a Fluid Sample Using Microfiltration

The present invention provides methods of enriching rare cells of a fluid sample using filtration through a microfabricated filter of the present invention that comprises at least one tapered pore. The method includes: dispensing a sample into a filtration chamber that comprises or engages at least one microfabricated filter that comprises at least one tapered pore; providing fluid flow of the sample through the filtration chamber, such that components of the fluid sample flow through or are retained by the one or more microfabricated filters based on the size, shape, or deformability of the components; and collecting enriched rare cells from said filtration chamber. In some embodiments, filtration can separate soluble and small components of a sample from at least a portion of the cells that are in the sample, in order to concentrate the retained cells to facilitate further separation and analysis. In some aspects, filtration can remove undesirable components from a sample, such as, but not limited to, undesirable cell types. Where filtration reduces the volume of a sample by at least 50% or removes greater than 50% of the cellular components of a sample, filtration can be considered a debulking step. The present invention contemplates the use of filtration for debulking as well as other functions in the processing of a fluid sample, such as, for example, concentration of sample components or separation of sample components (including, for example, removal of undesirable sample components and retention of desirable sample components).

Sample

A sample can be any fluid sample, such as an environmental sample, including air samples, water samples, food samples, and biological samples, including suspensions, extracts, or leachates of environmental or biological samples. Biological samples can be blood, a bone marrow sample, an effusion of any type, ascities fluid, pelvic wash fluid, or pleural fluid, spinal fluid, lymph, serum, mucus, sputum, saliva, urine, semen, occular fluid, extracts of nasal, throat or genital swabs, cell suspension from digested tissue, or extracts of fecal material. Biological samples can also be samples of organs or tissues, including tumors, such as fine needle aspirates or samples from perfusions of organs or tissues. Biological samples can also be samples of cell cultures, including both primary cultures and cell lines. The volume of a sample can be very small, such as in the microliter range, and may even require dilution, or a sample can be very large, such as up to about two liters for ascities fluid. A preferred sample is a blood sample.

A blood sample can be any blood sample, recently taken from a subject, taken from storage, or removed from a source external to a subject, such as clothing, upholstery, tools, etc. A blood sample can therefore be an extract obtained, for example, by soaking an article containing blood in a buffer or solution. A blood sample can be unprocessed or partially processed, for example, a blood sample that has been dialyzed, had reagents added to it, etc. A blood sample can be of any volume. For example, a blood sample can be less than five microliters, or more than 5 liters, depending on the application. Preferably, however, a blood sample that is processed using the methods of the present invention will be from about 10 microliters to about 2 liters in volume, more preferably from about one milliliter to about 250 milliliters in volume, and most preferably between about 5 and 50 milliliters in volume.

The rare cells to be enriched from a sample can be of any cell type present at less than one million cells per milliliter of fluid sample or that constitute less than 1% of the total nucleated cell population in a fluid sample. Rare cells can be, for example, bacterial cells, fungal cells, parasite cells, cells infected by parasites, bacteria, or viruses, or eukaryotic cells such as but not limited to fibroblasts or blood cells. Rare blood cells can be RBCs (for example, if the sample is an extract or leachate containing less than one million red blood cells per milliliter), subpopulations of blood cells and blood cell types, such as WBCs, or subtypes of WBCs (for example, T cells or macrophages), nucleated red blood cells, or can be fetal cells (including but not limited to nucleated red blood cells, trophoblasts, granulocytes, or monocytes). Rare cells can be stem or progenitor cells of any type. Rare cells can also be cancer cells, including but not limited to neoplastic cells, malignant cells, and metastatic cells. Rare cells may be candidate cancer cells, such as a rare cell in a blood sample that could be enriched and subjected to the process of detection, identification, characterization and the like that may specify a cancer cell. Rare cells of a blood sample can also be non-hematopoietic cells, such as but not limited to epithelial cells.

Dispensing of Sample into Filtration Chamber

A sample can be dispensed into a filtration chamber of the present invention by any convenient means. As nonlimiting examples, sample can be introduced using a conduit (such as tubing) through which a sample is pumped or injected into the chamber, or can be directly poured, injected, or dispensed or pipeted manually, by gravity feed, or by a machine. Dispensing of a sample into a filtration chamber of the present invention can be directly into the filtration chamber, via a loading reservoir that feeds directly or indirectly into a filtration chamber, or can be into a conduit that leads to a filtration chamber, or into a vessel that leads, via one or more conduits, to a filtration chamber. A needle (or any fluid drawing device) in fluid communication with tubing or a chamber can also be used to enter a tube. The needle may collect cells from a tube containing a solution and dispense the solution into another chamber using a device to push or pull a solution (e.g. pump or syringe).

Filtering

Following the addition to a filtration chamber of the present invention, filtering is effected by providing fluid flow through the chamber. Fluid flow can be provided by any means, including positive or negative pressure (for example, by a manual or machine operated syringe-type system), pumping, or even gravity. The filtration chamber can have ports that are connected to conduits through which a buffer or solution and the fluid sample or components thereof can flow. A filtration unit can also have valves that can control fluid flow through the chamber. When the sample is added to the filtration chamber, and fluid flow is directed through the chamber, filter slots can allow the passage of fluid, soluble components of the samples, and filterable non-soluble components of a fluid sample through a filter, but, because of the slot dimensions, can prevent the passage of other components of the fluid sample through the filter.

Preferably, fluid flow through a filtration chamber of the present invention is automated, and performed by a pump or positive or negative pressure system, but this is not a requirement of the present invention. The optimal flow rate will depend on the sample being filtered, including the concentration of filterable and nonfilterable components in the sample and their ability to aggregate and clog the filter. For example, the flow rate through the filtration chamber can be from less than 1 milliliter per hour to more than 1000 milliliters per hour, and flow rate is in no way limiting for the practice of the present invention. Preferably, however, filtration of a blood sample occurs at a rate of from 5 to 500 milliliters per hour, and more preferably at a rate of between about 10 and about 50 milliliters per hour.

In fabricating the filter slots through the filter substrate, slight tapering of the slot along the slot depth direction can occur. Thus a particular slot width may not be maintained constant throughout the entire depth of the filter and the slot width on one surface of the filter is typically larger than the width on the opposite surface. In utilizing such filters with tapered slot width, it is preferred to have the narrow-slot side of the filter facing the sample, so that during filtering the sample goes through the narrow-width side of the slot first and then filtered cells exit at the wide-width side of the slot. This avoids trapping cells that are being filtered within the funnel-shaped slots. However, the orientation of a filter with one or more tapered slots is not a restriction in using the filters of the present invention. Depending on specific applications, the filters can also be used in the orientation such that the wide-width side of the filter slots faces the sample.

In the methods of the present invention, preferably desirable components, such as rare cells whose enrichment is desired, are retained by the filter. Preferably, in the methods of the present invention as rare cells of interest of the sample are retained by the filter and one or more undesirable components of the sample flow through the filter, thereby enriching the rare cells of interest of the sample by increasing the proportion of the rare cells to total cells in the filter-retained portion of the sample, although that is not a requirement of the present invention. For example, in some embodiments of the present invention, filtration can enrich rare cells of a fluid sample by reducing the volume of the sample and thereby concentrating rare cells.

After filtering of the sample, optionally buffer can be washed through the filtration chamber to wash through any residual filterable cells. The buffer can be conveniently directed through the filtration chamber in the same manner as the sample, that is, preferably by automated fluid flow such as by a pump or pressure system, or by gravity, or the buffer can use a different fluid flow means that the sample. Typically the speed at which the wash buffer flows through the chamber will be greater than that of a sample, but this need not be the case. One or more washes can be performed, using the same or different wash buffers. In addition, optionally air can be forced through the filtration chamber, for example by positive pressure or pumping, to push residual cells through the filtration chamber. Also, it is possible to have one or more washes back flushed into the filtration chamber to assist in the washing of the chamber or removal of undesirable cells or assist in the recovery of desirable cells.

Additional Enrichment Steps

The present invention also contemplates using filtration in combination with other steps that can be used in enriching rare cells of a fluid sample. For example, debulking steps or separation steps can be used prior to or following filtration, such as but not limited to as disclosed in U.S. patent application Ser. No. 10/701,684, entitled "Methods, Compositions, and Automated Systems for Separating Rare Cells from Fluid Samples" filed Nov. 4, 2003, U.S. patent application Ser. No. 10/268,312, entitled "Methods, Compositions, and Automated Systems for Separating Rare Cells from Fluid Samples" filed Oct. 10, 2002, both of which are incorporated herein by reference for all disclosure relating to debulking and separation procedures that can be used in enriching rare cells of a fluid sample.

III. Methods of Enriching Rare Cells from a Blood Sample

The present invention includes novel and improved designs and methods for isolating rare cells from a blood sample. Blood sample preparation and rare cell enrichment methods known in the art and disclosed U.S. patent application Ser. No. 10/701,684, filed Nov. 4, 2003, U.S. patent application Ser. No. 10/268,312, filed Oct. 10, 2002, hereby incorporated by reference for all disclosure of blood sample preparation and rare cell isolation from blood samples, can be combined with the methods and designs disclosed herein.

Maternal Blood Sample Selection for Fetal Cell Isolation

The present invention includes methods for rare cell isolation from blood samples that include the selection of a blood sample of a particular gestational age for isolation of particular fetal cell types.

In one preferred embodiment of the present invention, a maternal blood sample for the isolation of fetal nucleated cells is selected to be from the gestational age of between about 4 weeks and about 37 weeks, preferably about 7 weeks and about 24 weeks, and more preferably between about 10 weeks and about 20 weeks. In this embodiment, a maternal blood sample for the isolation of fetal nucleated cells is drawn from a pregnant subject at the gestational age of between about 4 weeks and about 37 weeks, preferably about 7 weeks and about 24 weeks, and more preferably between about 10 weeks and about 20 weeks. As used herein, a pregnant subject can also include a woman of the given gestational age that has aborted within twenty-four hours of the blood sample draw.

Use of the Second Wash Supernatant for Isolation Fetal Cells from a Maternal Blood Sample The present invention also includes methods for isolating fetal cells from a maternal blood sample in which the supernatant of a second centrifugation performed on the blood sample to wash the cells prior to a debulking or separation step is used as at least a part of the sample from which fetal cells are isolated.

Use of an Antibody to Remove Platelets from a Blood Sample

The present invention also includes the use of an antibody or molecule capable of specifically binding a platelet or a molecule associated with a platelet. As a nonlimiting example, antibodies or molecules or the present invention may specifically bind CD31, CD36, CD41, CD42(a, b, c), CD51 or CD51/61. CD31 is an endothelial and platelet cell marker that has minimal binding to fetal cells. Its use in separating platelets from a blood sample is described in the examples.

Improved Magnet Configurations for Capture of Sample Components

A debulked sample, such as a debulked blood sample, can be incubated with one or more specific binding members, such as, but not limited to, antibodies, that specifically recognize one or more undesirable components of a fluid sample. Where a filtration chamber has been used for debulking the sample, mixing and incubation of one or more specific binding members with the sample can optionally be performed in a filtration chamber. The one or more undesirable components can be captured, either directly or indirectly, via their binding to the specific binding member. For example, a specific binding member can be bound to a solid support, such as a bead, membrane, or column matrix, and following incubation of the fluid sample with the specific binding member, the fluid sample, containing unbound components, can be removed from the solid support. Alternatively, one or more primary specific binding members can be incubated with the fluid sample, and, preferably following washing to remove unbound specific binding members, the fluid sample can be contacted with a secondary specific binding member that can bind or is bound to a solid support. In this way the one or more undesirable components of the sample can become bound to a solid support, enabling separation of the undesirable components from the fluid sample.

In a preferred aspect of the present invention, a debulked blood sample from a pregnant individual is incubated with magnetic beads that are coated with antibody that specifically binds white blood cells and does not appreciably bind fetal nucleated cells. The magnetic beads are collected using capture by activated electromagnetic units (such as on an electromagnetic chip), or capture by at least one permanent magnet that is in physical proximity to a vessel, such as a tube or column, that contains the fluid sample. After capture of the magnetic beads by the magnet, the remaining fluid sample is removed from the vessel. The sample can be removed manually, such as by pipeting, or by physical forces such as gravity, or by fluid flow through a separation column. In this way, undesirable white blood cells can be selectively removed from a maternal blood sample. The sample can optionally be further filtered using a microfabricated filter of the present invention. Filtration preferably removes residual red blood cells from the sample and can also further concentrate the sample.

In one preferred embodiment, after incubation of magnetic beads that comprise a specific binding member that specifically bind undesirable components with a sample, the sample is transported through a separation column that comprises or engages at least one magnet. As the sample flows through the column, undesirable components that are bound to the magnetic beads adhere to one or more walls of the tube adjacent to the magnet or magnets. An alternative embodiment uses a magnetic separator, such as the magnetic separator manufactured by Immunicon. Magnetic capture can also employ electromagnetic chips that comprise electromagnetic physical force-generating elements, such as those described in U.S. Pat. No. 6,355,491 entitled "Individually Addressable Micro-Electromagnetic Unit Array Chips" issued Mar. 12, 2002 to Zhou et al., U.S. application Ser. No. 09/955,343, filed Sep. 18, 2001, entitled "Individually Addressable Micro-Electromagnetic Unit Array Chips" and U.S. application Ser. No. 09/685,410, filed Oct. 10, 2000, entitled "Individually Addressable Micro-Electromagnetic Unit Array Chips in Horizontal Configurations". In yet another preferred embodiment, a tube that contains the sample and magnetic beads is positioned next to one or more magnets for the capture of nondesirable components bound to magnetic beads. The supernatant, depleted of the one or more nondesirable components, can be removed from the tube after the beads have collected at the tube wall.

In some preferred embodiments of the present invention, removal of white blood cells from a sample is performed simultaneously with debulking the blood sample by selective sedimentation of red blood cells. In these embodiments, a solution that selectively sediments red blood cells is added to a blood sample, and a specific binding member that specifically binds white blood cells that is bound to a solid support, such as magnetic beads, is added to the blood sample. After mixing, red blood cells are allowed to settle, and white blood cells are captured, such as by magnetic capture. This can be conveniently performed in a tube to which a sedimenting solution and the specific binding member, preferably bound to magnetic beads, can be added. The tube can be rocked for a period of time for mixing the sample, and then positioned next to one or more magnets for the capture of the magnetic beads. In this way, in a single incubation and separation step, approximately 99% of RBCs and 99% of WBCs can be removed from a sample. The supernatant can be removed from the tube and subjected to filtration using a microfabricated filter of the present invention. Filtration removes remaining RBCs, resulting in a sample in which rare cells, such as, for example, fetal cells, cancer cells, candidate cancer cells, non-hematopoietic cells, or stem cells, have been enriched.

Figure 22:
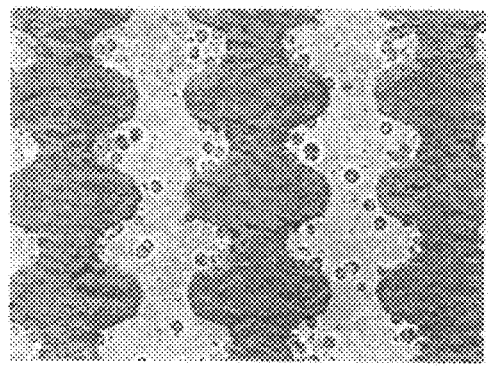
FIG. 22 depicts white blood cells of a blood sample retained on electrodes of a dielectrophoresis chip.

Undesirable components of a sample can be removed by methods other than those using specific binding members. For example, the dielectrical properties of particular cell types can be exploited to separate undesirable components dielectrophoretically. For example, FIG. 22 depicts white blood cells of a diluted blood sample retained on electrodes of a dielectrophoresis chip after red blood cells have been washed through the chamber.

Combined Solution for Sedimenting Red Blood Cells and Selectively Removing Undesirable Sample Components of a Blood Sample In preferred embodiments of the present invention, a solution that sediments red blood cells can also include one or more additional specific binding members that can be used to selectively remove undesirable sample components other than red blood cells from the blood sample. In this regard, the present invention includes a combined sedimenting solution for enriching rare cells of a blood sample that sediments red blood cells and provides reagents for the removal of other undesirable components of the sample. Thus a combined solution for processing a blood sample comprises: dextran; at least one specific binding member that can induce agglutination of red blood cells; and at least one additional specific binding member that can specifically bind undesirable components of the sample other than RBCs.

Specific Binding Member for Removing Undesirable Components

In addition to the components of a sedimenting solution of the present invention, a combined solution of the present invention can comprise at least one specific binding member that can selectively bind undesirable components of a blood sample (such as but not limited to white blood cells, platelets, serum proteins) and have less binding to desirable components. One or more specific binding members that can selectively bind non-RBC undesirable components of a blood sample can be used to remove the undesirable components of the sample, increasing the relative proportion of rare cells in the sample, and thus contribute to the enrichment of rare cells of the sample. By "selectively binds" is meant that a specific binding member used in the methods of the present invention to remove one or more undesirable sample components does not appreciably bind to rare cells of interest of the fluid sample. By "does not appreciably bind" is meant that not more than 30%, preferably not more than 20%, more preferably not more than 10%, and yet more preferably not more than 1.0% of one or more rare cells of interest are bound by the specific binding member used to remove non-RBC undesirable components from the fluid sample. In many cases, the undesirable components of a blood sample will be white blood cells. In preferred embodiments of the present invention, a combined solution of the present invention can be used for sedimenting red blood cells and selectively removing white blood cells from a blood sample.

A specific binding member that can specifically bind white blood cells can be as nonlimiting examples, an antibody, a ligand for a receptor, transporter, channel or other moiety of the surface of a white blood cell, or a lectin or other protein that can specifically bind particular carbohydrate moieties on the surface of a white blood cell (for example, a selectin).

Preferably, a specific binding member that selectively binds white blood cells is an antibody that binds white blood cells but does not appreciably bind fetal nucleated cells, such as, for example, an antibody to CD3, CD11b, CD14, CD17, CD31, CD45, CD50, CD53, CD63, CD69, CD81, CD84, CD102, or CD166. Antibodies can be purchased commercially from suppliers such as, for example Dako, BD Pharmingen, Antigenix America, Neomarkers, Leinco Technologies, Research & Diagnostic Systems, Serotec, United States Biological, Bender Medsystems Diagnostics, Ancell, Leinco Technologies, Cortex Biochem, CalTag, Biodesign, Biomeda, Accurate Chemicals & Scientific and Chemicon International. Antibodies can be tested for their ability to bind an efficiently remove white blood cells and allow for the enrichment of rare cells of interest from a sample using capture assays well known in the art.

Specific binding members that selectively bind to one or more undesirable components of the present invention can be used to capture one or more non-RBC undesirable components, such that one or more desirable components of the fluid sample can be removed from the area or vessel where the undesirable components are bound. In this way, the undesirable components can be separated from other components of the sample that include the rare cells to be separated. The capture can be affected by attaching the specific binding members that recognize the undesirable component or components to a solid support, or by binding secondary specific binding members that recognize the specific binding members that bind the undesirable component or components, to a solid support, such that the undesirable components become attached to the solid support. In preferred embodiments of the present invention, specific binding members that selectively bind undesirable sample components provided in a combined solution of the present invention are coupled to a solid support, such as microparticles, but this is not a requirement of the present invention.

Magnetic beads are preferred solid supports for use in the methods of the present invention to which specific binding members that selectively bind undesirable sample components can be coupled. Magnetic beads are known in the art, and are available commercially. Methods of coupling molecules, including proteins such as antibodies and lectins, to microparticles such as magnetic beads are known in the art. Preferred magnetic beads of the present invention are from 0.02 to 20 microns in diameter, preferably from 0.05 to 10 microns in diameter, and more preferably from 0.05 to 5 microns in diameter, and even more preferably from 0.05 to 3 microns in diameter and are preferably provided in a combined solution of the present invention coated with a primary specific binding member, such as an antibody that can bind a cell that is to be removed from the sample, or a secondary specific binding member, such as streptavidin, that can bind primary specific binding members that bind undesirable sample components (such as biotinylated primary specific binding members).

In preferred embodiments of the present invention, the fluid sample is a maternal blood sample, the rare cells whose separation is desirable are fetal cells, and the undesirable components of the sample to be removed from the sample are white blood cells. In these embodiments, a specific binding member that selectively binds white blood cells is used to remove the white blood cells from the sample by magnetic capture. Preferably, the specific binding member provided is attached to magnetic beads for direct capture, or, is provided in biotinylated form for indirect capture of white blood cells by streptavidin-coated magnetic beads.

A combined solution for enriching rare cells of a blood sample of the present invention can also include other components, such as, but not limited to, salts, buffering agents, agents for maintaining a particular osmolality, chelators, proteins, lipids, small molecules, anticoagulants, etc. For example, in some preferred aspects of the present invention, a combined solution comprises physiological salt solutions, such as PBS, PBS lacking calcium and magnesium or Hank's balanced salt solution. In some preferred aspects of the present invention, EDTA or heparin are present to prevent red blood cell clotting.

IV. Method of Enriching Rare Cells of a Blood Sample Using a Solution that Selectively Sediments Red Blood Cells The present invention also includes a method of enriching rare cells of a blood sample (including but not limited to e.g. peripheral blood) using a solution that selectively sediments red blood cells. The method includes: adding a red blood cell sedimenting solution of the present invention to a blood sample, mixing the blood sample and the red blood cell sedimenting solution, allowing red blood cells to sediment from the sample, and removing a supernatant that comprises enriched rare cells.

Blood Sample

A blood sample can be any blood sample, recently taken from a subject, taken from storage, or removed from a source external to a subject, such as clothing, upholstery, tools, etc. A blood sample can therefore be an extract obtained, for example, by soaking an article containing blood in a buffer or solution. A blood sample can be unprocessed or partially processed, for example, a blood sample that has been dialyzed, had reagents added to it, etc. In some cases, it can be preferable to use a washed blood sample, in which blood cells have been pelleted and resuspended in a blood-compatible buffer (for example, PBE) at least once. A blood sample can be of any volume. For example, a blood sample can be less than five microliters, or more than 5 liters, depending on the application. Preferably, however, a blood sample that is processed using the methods of the present invention will be from about 10 microliters to about 2 liters in volume, more preferably from about one milliliter to about 250 milliliters in volume, and most preferably between about 5 and 50 milliliters in volume.

Addition of Sedimenting Solution to Sample

A red blood cell sedimenting solution can be added to a blood sample by any convenient means, such as pipeting, automatic liquid uptake/dispensing devices or systems, pumping through conduits, etc. In most cases, the blood sample will be in a tube that provides for optimal separation of sedimented cells, but it can be in any type of vessel for holding a liquid sample, such as a plate, dish, well, or chamber. The amount of sedimenting solution that is added to a blood sample can vary, and will largely be determined by the concentration of dextran and specific binding members in the sedimenting solution (as well as other components), so that their concentrations will be optimal when mixed with the blood sample. Optimally, the volume of a blood sample is assessed, and an appropriate proportional volume of sedimenting solution, ranging from 0.01 to 100 times the sample volume, preferably ranging from 0.1 times to 10 times the sample volume, and more preferably from 0.25 to 5 times the sample volume, and even more preferably from 0.5 times to 2 times the sample volume, is added to the blood sample. (It is also possible to add a blood sample, or a portion thereof, to a red blood cell sedimenting solution. In this case, a known volume of sedimenting solution can be provided in a tube or other vessel, and a measured volume of a blood sample can be added to the sedimenting solution.)

Mixing

The blood sample and red blood cell sedimenting solution are mixed so that the chemical RBC aggregating agent (such as a polymer, such as, for example, dextran) and one or more specific binding members of the sedimenting solution, as well as the components of the blood sample are distributed throughout the sample vessel. Mixing can be achieved means such as electrically powered acoustic mixing, stirring, rocking, inversion, agitation, etc., with methods such as rocking and inversion, that are least likely to disrupt cells, being favored.

Incubation of Blood Sample and Sedimenting Solution

The sample mixed with sedimenting solution is allowed to incubate to allow red blood cells to sediment. Preferably the vessel comprising the sample is stationary during the sedimentation period so that the cells can settle efficiently. Sedimentation can be performed at any temperature from about 5 degrees C. to about 37 degrees C. In most cases, it is convenient to perform the steps of the method from about 15 degrees C. to about 27 degrees C. The optimal time for the sedimentation incubation can be determined empirically for a given sedimenting solution, while varying such parameters as the concentration of dextran and specific binding members in the solution, the dilution factor of the blood sample after adding the sedimenting solution, and the temperature of incubation. Preferably, the sedimentation incubation is from five minutes to twenty four hours in length, more preferably from ten minutes to four hours in length, and most preferably from about fifteen minutes to about one hour in length. In some preferred aspects of the present invention, the incubation period is about thirty minutes.

Collecting Enriched Cells

Removing a supernatant (or a portion thereof) from the sample after the red blood cells have sedimented can be performed by pouring, pipeting, pumping, or a fluid uptake device. The supernatant comprises enriched rare cells of the blood sample, such as, but not limited to, stem cells, fetal cells, nucleated red blood cells, mesenchymal cells, subpopulations of blood cells (including but not limited to e.g. T cells, dendritic cells), non-hematopoietic cells (including but not limited to e.g. epithelial cells, endothelial cells), cancer cells, candidate cancer cells, pre-neoplastic cells, neoplastic cells, metastatic cells, virus-infected cells, parasite-infected cells, parasitic cells, or bacterial cells. Following RBC sedimentation with a RBC sedimenting solution of the present invention, the proportion of the rare cells to the other cell types in the sample has increased, thus resulting in enriched rare cells.

Method of Enriching Rare Cells of a Blood Sample Using a Combined Sedimenting Solution The present invention also includes a method of enriching rare cells of a blood sample using a combined solution for enriching rare cells of a blood sample. The method comprises: adding a combined solution for enriching rare cells of the present invention to a blood sample in a tube or vessel; mixing the blood sample and combined solution of the present invention; allowing red blood cells to sediment from the blood sample; allowing undesirable components to bind a solid support; and removing a supernatant from said blood sample that comprises enriched rare cells.

Blood Sample

A blood sample can be any blood sample, recently taken from a subject, taken from storage, or removed from a source external to a subject, such as clothing, upholstery, tools, etc. A blood sample can therefore be an extract obtained, for example, by soaking an article containing blood in a buffer or solution. A blood sample can be unprocessed or partially processed, for example, a blood sample that has been dialyzed, had reagents added to it, etc. In some cases, it can be preferably to use a washed blood sample, in which blood cells have been pelleted and resuspended in a blood-compatible buffer (for example, PBE) at least once. A blood sample can be of any volume. For example, a blood sample can be less than five microliters, or more than 5 liters, depending on the application. Preferably, however, a blood sample that is processed using the methods of the present invention will be from about 10 microliters to about 2 liters in volume, more preferably from about one milliliter to about 250 milliliters in volume, and most preferably between about 5 and 50 milliliters in volume.

Addition of Sedimenting Solution to Sample

A combined sedimenting solution can be added to a blood sample by any convenient means, such as pipeting, automatic liquid uptake/dispensing devices or systems, pumping through conduits, etc. In most cases, the blood sample will be in a tube that provides for optimal separation of sedimented cells, but it can be in any type of vessel for holding a liquid sample, such as a plate, dish, well, or chamber. The amount of combined sedimenting solution that is added to a blood sample can vary, and will largely be determined by the concentration of dextran and specific binding members in the combined solution (as well as other components), so that their concentrations will be optimal when mixed with the blood sample. Optimally, the volume of a blood sample is assessed, and an appropriate proportional volume of combined solution, preferably ranging from 0.1 times to 10 times the sample volume, and more preferably from 0.25 to 5 times the sample volume, and even more preferably from 0.5 times to 2 times the sample volume, is added to the blood sample. (It is also possible to add a blood sample, or a portion thereof, to a combined solution. In this case, a known volume of combined solution can be provided in a tube or other vessel, and a measured volume of a blood sample can be added to the combined solution.)

Mixing

The blood sample and combined sedimenting solution are mixed so that the dextran and specific binding members of the combined solution, as well as the components of the blood sample, are distributed throughout the sample vessel, and specific binding members can bind to sample components. Mixing can be achieved means such as electrically powered acoustic mixing, stirring, rocking, inversion, agitation, etc., with methods such as rocking and inversion, that are least likely to disrupt cells, being favored.

Incubation of Blood Sample and Combined Solution

The sample mixed with combined sedimenting solution is allowed to incubate to allow red blood cells to sediment. Preferably the vessel comprising the sample is stationary during the sedimentation period so that the red blood cells can settle efficiently. Sedimentation can be performed at any temperature from about 5 degrees C. to about 37 degrees C. In most cases, it is convenient to perform the steps of the method from about 15 degrees C. to about 27 degrees C. The optimal time for the sedimentation incubation can be determined empirically for a given combined sedimenting solution, while varying such parameters as the concentration of dextran and specific binding members in the solution, the dilution factor of the blood sample after adding the combined solution, and the temperature of incubation. Preferably, the sedimentation incubation is from ten minutes to twenty four hours in length, more preferably from fifteen minutes to one hour in length. In some preferred aspects of the present invention, the incubation period is about thirty minutes.

Allowing Undesirable Sample Components or Rare Cells Bound by Specific Binding Members to Bind a Solid Support Allowing undesirable components or rare cells bound by specific binding members to bind a solid support can be performed in any of several ways, depending on the nature of the specific binding member that binds undesirable sample components, the type of solid support, and the overall format of the enrichments procedure (whether it is performed in one or more vessels, whether fluid flow is involved, etc.). In some embodiments, after the sedimentation step, the supernatant can be passed through or over a solid support that comprises secondary specific binding members that can bind the primary specific binding members (for example, streptavidin, if the primary specific binding member is biotinylated). For example, the supernatant can be pipetted or pumped through a column or over a membrane that can capture the undesirable components or rare cells bound by specific binding members. In other embodiments, one or more specific binding members that can bind undesirable sample components or rare cells can be bound to a solid support, such as beads, that can be sedimented along with the red blood cells, with or without a centrifugation step.

In preferred embodiments of the present invention, magnetic beads are solid supports, and one or more specific binding members that bind undesirable sample components are bound to magnetic beads in a combined sedimenting solution of the present invention. The magnetic beads can be captured using a magnet before, during or after the sedimentation step. In preferred aspects of the present invention, during the sedimentation step magnetic beads comprising primary or secondary specific binding members for the capture of undesirable components or rare cells of the blood sample are collected by placing the vessel that contains the sample next to a magnet. Magnetic capture can also be performed when the combined solution comprises a specific binding member that can specifically bind undesirable components or rare cells or interest can be bound by magnetic beads that are coated with, for example, streptavidin (where the specific binding member is biotinylated).

Preferably, magnetic capture uses one or more permanent magnets, such as permanent magnets positioned within or alongside a tube, dish, or vessel that contains the target cell-magnetic bead complexes, and occurs during the sedimentation step. Commercially available magnetic separators that include permanent magnets (such as those sold by Immunicon (Huntington Valley, Pa.)) can also be used, however, or magnetic capture can also employ electromagnetic chips that comprise electromagnetic physical force-generating elements, such as those described in U.S. Pat. No. 6,355,491 entitled "Individually Addressable Micro-Electromagnetic Unit Array Chips" issued Mar. 12, 2002 to Zhou et al., U.S. application Ser. No. 09/955,343, filed Sep. 18, 2001, entitled "Individually Addressable Micro-Electromagnetic Unit Array Chips", and U.S. application Ser. No. 09/685,410, entitled "Individually Addressable Micro-Electromagnetic Unit Array Chips in Horizontal Configurations".

In preferred embodiments, combined solution of the present invention comprises at least one specific binding member that selectively binds white blood cells as undesirable components of the sample. The specific binding member is bound to, or is able to bind to, magnetic beads. The tube containing the sample mixed with the combined solution is positioned next to a magnet during sedimentation of red blood cells, and white blood cells are collected at the wall of the tube as red blood cells settle to the bottom of the tube. The supernatant comprises enriched rare cells.

Collecting Enriched Rare Cells

The process of collecting enriched cells will vary depending on whether a combined sedimenting solution comprises a specific binding member that selectively binds undesirable sample components or a specific binding member that selectively binds rare cells of interest. In embodiments in which a combined sedimenting solution comprises a specific binding member that selectively binds undesirable sample components, removing a supernatant (or a portion thereof) from the sample after the red blood cells have sedimented and undesirable sample components have been separated can be performed by pouring, pipetting, pumping, or a fluid uptake device. The supernatant comprises enriched rare cells of the blood sample, such as, but not limited to, stem cells, fetal cells, nucleated red blood cells, cancer cells, candidate cancer cells, virus-infected cells, parasite-infected cells, parasitic cells, or bacterial cells. The proportion of these cells relative to the total cell population in the collected supernatant has increased over their proportion of the total cell population in the pre-sedimented blood sample.

Further Enrichment Steps

The use of sedimenting solutions of the present invention, including combined solutions for enriching rare cells of a blood sample, can be combined with other processing steps such as debulking, or separation steps. Debulking steps that can be combined with the use of a combined solution include: as nonlimiting examples, selective lysis, filtration, and centrifugation steps. Additional separation steps that can be used include separations that include capture of sample components to solid supports using specific binding members, and separations performed on active chips, such as dielectrophoretic and traveling wave dielectrophoretic separations, and separations using electromagnetic capture on an electromagnetic chip.

The present invention also includes methods of enriching rare cells from a blood sample in which selective sedimentation of RBCs is combined with filtration, such as filtration through a microfabricated filter of the present invention.

A method for enriching rare cells of the present invention that comprises a RBC sedimentation step and at least one filtration step using a microfabricated filter of the present invention can also include other steps, such as, but not limited to: selectively removing further undesirable components from said fluid sample, separating rare cells of the sample, additional filtration steps, or additional debulking steps, such as, for example, selective lysis of one or more sample components.

In a particularly preferred embodiment, a blood sample can be processed to enrich rare cells, which may include but are not limited to fetal cells, stem cells, cancer cells or candidate cancer cells, or non-hematopoietic cells. Red blood cells can be removed by selective sedimentation of RBCs using a solution of the present invention. White blood cells can be removed by adding magnetic beads that are coated with one or more specific binding members that specifically bind white blood cells to the post-sedimentation supernatant, or, preferably, a combined solution of the present invention is used to sediment red blood cells and removes white blood cells using magnetic capture. The blood sample can then be dispensed into a filtration chamber that comprises at least one microfabricated filter of the present invention that comprises slots having dimension that allow RBCs to pass through the filter. Fluid flow through the chamber removes additional residual red blood cells and further reduces sample volume, resulting in a sample having enriched rare cells. Depending on the source of the sample, the enriched rare cells can be stem cells, fetal cells, cancer cells, candidate cancer cells, subtypes of white blood cells, bacterial cells, parasite cells, or bacteria-, parasite-, or virus-infected cells.

Additional Debulking Steps

As used herein, "debulking" refers to a step in the processing of a sample in which the volume of the sample is significantly reduced by at least fifty percent or greater than 50% of the cellular components of a sample are removed. For example, in preferred aspects of the present invention in which the fluid sample is a blood sample, a majority of the non-nucleated red blood cells (RBCs) that make up more than 90% of the cellular components of a blood sample are removed during a debulking step.

Additional debulking steps used before or after sedimenting red blood cells with a solution of the present invention can be, as nonlimiting examples, an additional sedimentation step, a concentration step, a centrifugation step, or a filtration step. Centrifugation and filtration are preferred debulking steps that reduce the volume of a fluid sample and at the same time allow the technician to select fractions of the centrifuged or filtered product that retain desirable components and do not retain at least a portion of some undesirable components.

Filtration using a microfabricated filter of the present invention has been disclosed earlier in the application. Other types of filtration steps can also be used. These include, as nonlimiting examples, filtration using columns packed with various resins or polymeric materials, filtration using membranes of pore sizes that allow retention of desirable components, filtration using channels that are microetched into one or more chips, by using "bricks" or dams that are built onto the surface of a chip, or by using slots or pores that are microetched into a solid surface that can be within a chamber or form a wall of a chamber as disclosed earlier in the application (see, for example, U.S. Pat. No. 5,837,115 issued Nov. 17, 1998 to Austin et al., herein incorporated by reference in its entirety and U.S. Pat. No. 5,726,026 issued Mar. 10, 1998 to Wilding et al., herein incorporated by reference in its entirety).

Another method for debulking blood sample is the use of hypotonic solutions to exploit the differential responses of maternal red blood cells (and reticulocytes) and white blood cells (and nucleated red blood cells). By treating blood samples with hypotonic solutions, red blood cells can be lysed, or red blood cells can be altered significantly so that they become readily separable from white blood cells and other nucleated cells. Alternatively, certain biochemical reagents may be used to selectively lyse red blood cells.

More than one debulking step can be employed in the methods of the present invention. For example, in some applications, undesirable components of the sample can be removed in steps subsequent to a first debulking step. It can then practical and advantageous to further reduce the volume of the remaining sample. This can be done through any of the described debulking methods, using scaled down volumes and areas where appropriate.

Separation Steps

The methods of the present invention can include sedimentation of red blood cells from a blood sample in combination with one or more separation steps. In general, a separation step will selectively remove one or more undesirable components from a sample, or selectively separate one or more desirable components of a sample. These steps will depend on the properties of the particular cells to be removed or separated from the sample, such as their binding properties, physical properties such as size or density, and electrical properties.

Sedimenting RBCs with Selectively Removal of Undesirable Components and Further Selective Removal of Undesirable Components.

The present invention includes methods in which the selective removal of one or more non-RBC undesirable components of a fluid sample is performed simultaneously with sedimenting red blood cells of a sample. However, in some methods of the present invention, in which a sedimenting solution does not comprise a specific binding member that selectively binds non-RBC undesirable components, removal of one or more undesirable components of a fluid sample can be performed before, during, or after sedimenting red blood cells from the blood sample. It is also possible to remove more than one type of undesirable component from a blood sample, and to perform the separations in separate steps.

Preferably, in the methods of the present invention, selective removal of one or more undesirable components of a fluid sample makes use of specific recognition of one or more undesirable components by one or more specific binding members. The use of specific binding members in removing undesirable components of a sample has been disclosed in earlier sections of the application and also applies here. The specific binding member used in the methods of the present invention can be any type of molecule or substrate that can specifically bind one or more undesirable components. Receptor ligands (either naturally occurring, modified, or synthetic), antibodies, and lectins are nonlimiting examples of specific binding members that can be used in the methods of the present invention. More than one different specific binding member can be used to capture one or more undesirable components to a solid support. Preferably, a specific binding member used in the methods of the present invention to selectively remove one or more undesirable components does not appreciably bind to desirable components of the fluid sample. In most applications of the present invention, a specific binding member used in the methods of the present invention to remove one or more undesirable components does not appreciably bind to the rare cells of the fluid sample that are to be separated. By "does not appreciably bind" is meant that not more than 30%, preferably not more than 20%, more preferably not more than 10%, and yet more preferably not more than 1.0% of the rare cell of the fluid sample that are to be enriched using the methods of the present invention are bound by the specific binding member used to selectively remove undesirable components of the fluid sample. Preferred specific binding members used in the methods of the present invention include antibodies, particularly antibodies that recognize and bind cell surface epitopes.

The capture can be affected by attaching antibodies that recognize the undesirable component or components to a solid support, or by binding secondary specific binding members that recognize the antibodies that bind the undesirable component or components, to a solid support, such that the undesirable components become attached to the solid support and become fixed at a particular location. A solid support can be, as nonlimiting examples, a surface, such as a plastic or polymeric surface, a gel or polymer, a membrane, the surface of a chip, or a bead. In the present invention, magnetic beads are preferred solid supports for the capture and selective removal of undesirable components of a sample. The capture of undesirable components of a sample can be direct or indirect. For direct capture, a first specific binding member that binds to one or more undesirable components of a sample can be attached to a solid support. The one or more undesirable components, when contacted with the solid support, then bind to the solid support. For indirect capture, a primary specific binding member that binds to one or more undesirable components of a sample can be contacted with the one or more undesirable components, and a secondary specific binding member that can bind the primary specific binding member can be attached to a solid support. When the undesirable components that have bound the primary specific binding member are contacted with the solid support, the one or more undesirable components of the sample can bind the solid support via the primary and secondary specific binding members. In certain preferred embodiments of the present invention where selective removal of one or more undesirable components of a sample is performed, direct capture is preferred, as direct capture comprises fewer steps.

The capture of undesirable components of a sample could also be done using specific binding members that recognize cell surface antigens or recognize the antibodies that bind the cell surface antigens and removed by other manipulations. An example but not limited to would be an antibody that recognizes an undesirable cell surface antigen, where the antibody could be labeled but are not limited to with markers that are chromophore, fluorescent, emit a signal, nanocrystal, microparticle, colloid, metal particle or other detectable reagent. This labeling of undesired components can be utilized before, during or after either the debulking or separation step. An example but not limited to utilization could be after the filtration step where the labeled undesirable components are then flow cytometry sorted for separation of unlabeled cells and thus enrichment by further removal of undesirable components.

In preferred embodiments of the present invention, the fluid sample is a maternal blood sample, the rare cells whose separation is desirable are fetal cells, and the undesirable components of the sample to be removed from the sample are white blood cells. In these embodiments, a specific binding member that selectively binds white blood cells is used to remove the white blood cells from the sample by magnetic capture. Preferably, the specific binding member is either used to coat magnetic beads for direct capture, or is used in biotinylated form for indirect capture of white blood cells by streptavidin-coated magnetic beads.

A blood sample from which red blood cells have been sedimented can be incubated with one or more specific binding members, such as, but not limited to, antibodies, that specifically recognize one or more undesirable components of a fluid sample. Mixing and incubation of one or more specific binding members with the sample can be performed in a tube, dish, vessel, or chamber. The one or more undesirable components can be captured, either directly or indirectly, via their binding to the specific binding member. For example, a specific binding member can be bound to a solid support, such as a bead, membrane, or column matrix, and following incubation of the fluid sample with the specific binding member, the fluid sample, containing unbound components, can be removed from the solid support. Alternatively, one or more primary specific binding members can be incubated with the fluid sample, and the fluid sample can be contacted with a secondary specific binding member that can bind or is bound to a solid support. In this way the one or more undesirable components of the sample can become bound to a solid support, enabling separation of the undesirable components from the fluid sample.

In one preferred embodiment, after incubation of magnetic beads that comprise a specific binding member that specifically bind undesirable components with a sample, the sample is transported through a separation column that comprises or engages at least one magnet. As the sample flows through the column, undesirable components that are bound to the magnetic beads adhere to one or more walls of the tube adjacent to the magnet or magnets. An alternative embodiment uses a magnetic separator, such as the magnetic separator manufactured by Immunicon. Magnetic capture can also employ electromagnetic chips that comprise electromagnetic physical force-generating elements, such as those described in U.S. Pat. No. 6,355,491 entitled "Individually Addressable Micro-Electromagnetic Unit Array Chips" issued Mar. 12, 2002 to Zhou et al., U.S. application Ser. No. 09/955,343, entitled "Individually Addressable Micro-Electromagnetic Unit Array Chips", and U.S. application Ser. No. 09/685,410, filed Oct. 10, 2000, entitled "Individually Addressable Micro-Electromagnetic Unit Array Chips in Horizontal Configurations". In yet another preferred embodiment, a tube that contains the sample and magnetic beads is positioned next to one or more magnets for the capture of undesirable components bound to magnetic beads. The supernatant, depleted of the one or more undesirable components, can be removed from the tube after the beads have collected at the tube wall.

Other manipulations that can be performed to remove undesirable components from a blood sample before or preferably after sedimenting red blood cells include passing the sample or sample supernatant over a solid support (which can be, as nonlimiting examples, a membrane or a matrix) that comprises attached specific binding members that capture the undesirable components. The blood sample or blood sample supernatant can be incubated with or passed through or over such a solid support to remove undesirable components, such as, but not limited to, white blood cells. Flow cytometry, dielectrophoretic separation, filtration, or other separation techniques can also optionally be employed to remove undesirable components from blood samples.

Sedimenting RBCs with Selective Removal of Undesirable Components and Further Separating Desirable Components The present invention also includes methods in which sedimenting rare cells is combined with the separation of one or more desirable components, such as rare cells whose enrichment is desired, from a fluid sample. Preferably, separation of rare cells from a fluid sample occurs after red blood cell sedimentation.

In some preferred embodiments of the present invention, separating rare cells uses at least one specific binding member that specifically binds the one or more rare cells and capture of the rare cells to a solid support. Receptor ligands (either of natural sources, modified, or synthetic), antibodies, and lectins are nonlimiting examples of specific binding members that can be used in the methods of the present invention. More than one different specific binding member can be used to capture one or more rare cells to a solid support.

A specific binding member can be any type of molecule or substrate that can selectively bind one or more rare cell types. Preferred specific binding members used in the methods of the present invention include antibodies, particularly antibodies that recognize and bind antigens on the surface of rare cells.

In a particularly preferred embodiment, the fluid sample is a blood sample and fetal nucleated cells are the rare cells to be enriched. In this case, specific binding members such as lectins or antibodies can be used to bind and remove white blood cells.

Antibodies can also be used as specific binding members for other manipulations such as to label fetal nucleated cells from a blood sample. For example, a CD71 antibody can be used. An antibody or antibodies can also be used to enrich other rare cells such as, for example, cancer cells or stem cells from fluid samples such as urine or blood samples. Antibodies, lectins, or other specific binding members can be tested for their ability to bind an efficiently separate particular rare cell types from a sample using capture assays well known in the art.

A blood sample from which red blood cell have been sedimented can be incubated with one or more specific binding members, such as antibodies, that specifically recognize one or more rare cell types of a fluid sample. The one or more rare cell types can be captured, via their direct or indirect binding to the specific binding member, and the remainder of the fluid sample can be removed from the area, surface, or vessel where the rare cells being isolated are bound. For example, a specific binding member can be bound to a solid support, such as a membrane or column matrix, and following incubation of the fluid sample with the specific binding member, the fluid sample, containing unbound components, can be removed from the solid support. A solid support can be, as nonlimiting examples, a surface, such as a plastic surface, a gel or polymer, a membrane, the surface of a chip, or a bead. In the present invention, magnetic beads are preferred solid supports for the separation and capture of rare cells of a sample.

Capture of cells, viruses, molecules, and other moieties to solid supports is well known in the arts of cell biology, biochemistry, and antibody technology, and can use a variety of formats known in the art. The capture of rare cells of a sample can be direct or indirect. For direct capture, a first specific binding member that binds to one or more rare cells of a sample can be attached to a solid support. The rare cells, when contacted with the solid support, then bind to the solid support. For indirect capture, a primary specific binding member that binds to the desirable rare cells of a sample can be contacted with the one or more rare cells, and a secondary specific binding member that can bind the primary specific binding member can be attached to a solid support. When the rare cells that have bound the primary specific binding member are contacted with the solid support, the one or more rare cells of the sample can bind the solid support via the primary and secondary specific binding members.

In many cases it can be preferable to provide the specific binding member that binds the rare cells already bound to a solid support. For example, beads, such as magnetic beads, to which one or more specific binding members that bind the rare cells are attached can be added to the sample, or the sample can be passed over a solid support such as a membrane or the surface of a plate that comprises a specific binding member, or through a solid support such as a column matrix that comprises a specific binding member. Using specific binding members that are directly bound to a solid support can increase the efficiency of the enrichment procedure.

In preferred embodiments, separation of one or more rare cells of the sample using specific binding members to capture the rare cells to a solid support, and can be performed in a dish, well, tube, column, or other vessel. In some preferred embodiments, the solid support comprises magnetic beads.

Magnetic beads are preferred solid supports for use in the methods of the present invention. Magnetic beads are known in the art, and are available commercially. Magnetic beads can be purchased that are coated with secondary specific binding members, for example secondary antibodies or streptavidin. Preferred magnetic beads of the present invention are from 0.02 to 20 microns in diameter, preferably from 0.05 to 10 microns in diameter, and more preferably from 0.05 to 5 microns in diameter, and even more preferably from 0.05 to 3 microns in diameter and are coated with either streptavidin, a secondary antibody, or a primary antibody that can bind a cell that is to be separated from the sample. Where streptavidin coated beads are used, the primary specific binding member is preferably biotinylated (for example a biotinylated primary antibody) such that the streptavidin coated bead will bind a sample component that is bound to the biotinylated antibody through a streptavidin-biotin link. Methods of using magnetic beads in the capture of directly or indirectly bound cells are well known in the art, and are also described in the examples provided. The methods of capture can use permanent magnets, such as permanent magnets positioned within or alongside a tube, dish, or vessel that contains the target cell-magnetic bead complexes, or commercially available magnetic separators that include permanent magnets (Immunicon). Magnetic capture can also employ electromagnetic chips that comprise electromagnetic physical force-generating elements, such as those described in U.S. Pat. No. 6,355,491 entitled "Individually Addressable Micro-Electromagnetic Unit Array Chips" issued Mar. 12, 2002 to Zhou et al., U.S. application Ser. No. 09/955,343, filed Sep. 18, 2001, entitled "Individually Addressable Micro-Electromagnetic Unit Array Chips", and U.S. application Ser. No. 09/685,410, filed Oct. 10, 2000, entitled "Individually Addressable Micro-Electromagnetic Unit Array Chips in Horizontal Configurations".

A discussion and references of the use of electromagnetic forces and their use is separations provided in a previous section of this application on methods of enriching rare cells involving filtration can also be applied to the separation of rare cells following RBC sedimentation.

Rare cells of the present invention can also be separated from a fluid sample using dielectrophoretic forces. The use of dielectrophoretic forces can be employed where the rare target cells have dielectrophoretic properties than are significantly different than other components that remain in the sample. That is, the difference in dielectrophoretic properties between rare target cells and nondesirable sample components must be sufficient to allow dielectrophoretic separation using micro-scale electrodes that can be built into or onto a chip. In most cases in which the fluid sample is a biological fluid sample, the other components of the sample whose dielectric properties must be taken into account are cells, such as cells that are not rare target cells. The feasibility of using dielectrophoresis for the separation of rare target cells can therefore depend on whether nondesirable components having similar dielectrophoretic properties as the target cells. Preferably, then, in applications of the method where a sample comprises a type of non-target cells that have similar dielectrophoretic properties as the target cells, selective removal of the type of non-target cells using methods other than dielectrophoresis has been performed prior to dielectrophoretic separation of target cells. Preferably in such instances, the selective removal of the non-target cells with similar dielectric properties using methods other than dielectrophoresis has been efficient, where efficiency refers to the percentage of non-target cells removed. The level of efficiency can vary with the application, but preferably the efficiency of selective removal of non-target cells with similar dielectric properties is greater than 30% of the non-target cells removed, more preferably greater than 50% of the non-target cells removed, and more preferably yet, greater than 90% of the non-target cells removed, and even more preferably, greater than 99% of the non-target cells removed in the selective removal step.

The previous discussion and references provided for the design and use of micro-electrodes to facilitate filtration by translocating sample components, such as nonfilterable cells, away from a filter using dielectrophoresis are also relevant to the use of micro-electrodes to facilitate dielectrophoretic separation of rare target cells. Various dielectrophoresis separation methods, such as those described in U.S. application Ser. No. 09/686,737, filed Oct. 10, 2000 entitled "Compositions and Methods for Separation of Moieties on Chips", incorporated by reference, and described in U.S. application Ser. No. 09/679,024, entitled "Apparatuses Containing Multiple Active Force Generating Elements and Uses Thereof" filed Oct. 4, 2000, also herein incorporated by reference in its entirety, may be employed for separating rare target cells.

In some applications of the present invention, separation of rare cells from a fluid sample may exploit the differences in cell physical properties. For example, as discussed above, dielectrophoresis may be used to separate nucleated red blood cells from non-nucleated red blood cells By exploiting the differences in their dielectric properties, nucleated red blood cells and mature red blood cells (and reticulocytes) are caused to exhibit positive and negative (or small positive) dielectrophoresis forces, respectively, under certain cell suspension and electric field conditions. When the cell suspension is introduced to a chamber containing microelectrodes on the bottom surface, nucleated red blood cells can be collected and retained on the electrodes while the non-nucleated red blood cells are carried away from the chamber together with the fluid stream.

Other manipulations that can be performed to separate rare cells from a blood sample before or preferably after sedimenting red blood cells include passing the sample or sample supernatant over a solid support (which can be, as nonlimiting examples, a membrane or a matrix) that comprises attached specific binding members that capture the undesirable components. The blood sample or blood sample supernatant can be incubated with or passed through or over such a solid support to collect the rare cells.

In addition to the manipulations set forth above rare cells may be enriched by further methods of manipulation using methods of detection, identification, characterization, culture and the like. These methods may have particular utility when used in combination with debulking of samples such as blood samples.

Fluid Volume Sensing Means

An automated system of the present invention can have means for sensing the volume of a fluid, such as, but not limited to, the volume of a fluid sample, including a fluid sample supernatant. The means for sensing the volume of a fluid preferably relies on optical sensing, such as detection of transmittance, absorption, reflectance, or fluorescence, and can comprise a light source, such as a light bulb, laser, or LED, and a sensing structure such as CCDs or photomultipliers appropriately aligned with the light source or sources. Thus the volume sensing means can comprise a light transmission-light sensing system that does not rely on contacting the sample to detect volume. Wavelengths for particular sensing applications can be readily determined, for example, for turbidity (600 nm), or the absorbance of particular sample components. A light source that is part of a light transmission-light sensing system can transmit light in the non-visible range, such as the ultraviolet or infrared range. For example, the fraction of a sample that comprises red blood cells can be detected using light in the range of 700 to 900 nanometers, more preferably between 750 and 850 nanometers.

In a preferred embodiment of fluid volume sensing means, the light source is a laser that emits collated light, that is, filtered, polarized light that can transmit through a sample tube, and in some preferred embodiments, can transmit through a sample or a fraction of a sample that does not absorb at the wavelength of the emitted light. (The tube, vessel, or other container that holds the sample whose volume is to be determined should be transparent to, or substantially transparent to, the emitted light.)

A light source and detection device can be mobile, so that they can continuously or in graduated fashion scan the length of the tube or column that contains the sample, or the fluid volume sensing means can have multiple light sources and multiple detectors that are oriented vertically and can simultaneously detect optical parameters and thereby determine the volume of a sample (or a subfraction thereof). Because blood samples contain cells such as RBCs and WBCs, a change in the optical characteristics can determine the locus of particular cell types. It is also possible to fluorescently label cells so that fluorescence can be used for localization.

For example, a light source, such as but not limited to a light bulb, laser, or LED, can interrogate the tube or column of sample. The transmittance, absorption or reflectance of the incident light can be measured by appropriate structures, such as CCDs or photomultipliers.

The automated fluid volume sensing means can be used to determine the volume of a sample or a portion thereof at any of various stages in the processing of a sample. In one embodiment, fluid volume sensing means can determine the starting volume of a sample by detecting, for example, absorbance/transmission of light of a given wavelength along the length of a tube, vial, cuvette, etc. This can be used, for example, to calculate the amount of a reagent to add to a sample. In a preferred method for processing a blood sample, the automated system calculates the amount of combined solution to add to each sample tube, and adds the appropriate amounts using an automated fluid dispensing system.

In other embodiments, fluid volume sensing means can be used to determine the volume of a fraction of a sample. For example, a sample precipitate can have different light absorption characteristics than a sample supernatant, or two phases of a separated sample can have different light absorption characteristics. In a preferred example, an interface between sedimented red blood cells and a sample supernatant can be localized using fluid volume sensing means.

Because layers of the sample column with a high density of RBCs are optically dense and do not transmit light well, the interface between high and low RBC densities can be determined by such optical methods. The instrument can localize such interface or zone and calculate the volume of a precipitate, supernatant, or phase of the sample.

In this sense, "calculate a volume" does not require that the system perform a calculation that arrives at a volume per se, although this can be done. In most embodiments, the automated system will determine a height or level or a sample or interface or boundary, and this determination will direct the fluid uptake system to remove a certain amount of sample or add a certain amount of reagent or solution to the sample.

This can be done by using a light source and detection device that are mobile, and either continuously or in graduated fashion scans the length of the tube or column, or by having multiple light sources and detectors that are oriented vertically and can simultaneously detect optical density and thereby determine the volume of the sample (or subfraction thereof). Preferably, a light source moves in a coordinated fashion with a light detection device to scan a sample tube or vessel. In a preferred embodiment, a light transmission-light sensing device comprises a bar oriented essentially horizontally and having on one end a light source, such as a collated light source, and on the other end, a light sensor. The bar is proximal to or can be positioned proximal to the sample tube in a rack, such that the light source is on one side of the tube, and the light sensor is at the opposite end of the tube. The upper level of the bar corresponds to the level of the light source.

To determine the volume of a sample supernatant, the bar moves upward from the level of the bottom of the tube. The detection device records the amount of light through the sample, and, when a boundary is detected (light transmission reaches a threshold value or significant difference in the amount of transmitted light within a short distance), the bar stops at the boundary position, for example, at the interface between fractions of a sample, such as a sample supernatant and a sample precipitate.

The boundary determination can be used to direct a fluid uptake/dispensing system to remove the upper phase or supernatant of the sample. The sample supernatant or upper phase can be removed by directing the tip of a fluid uptake device relative to the level of the detected interface. This can be done by having the collection tip position itself over the bar and move downward to the bar (which has stopped at the level of the interface). When the tip contacts the bar, the tip level is recorded. The collection tip then moves back up, positions itself over the sample tube, and descends into the sample tube. When the tip electronically senses fluid, it begins to take up fluid (supernatant) from the sample. The tip continues to descend into the tube while taking up supernatant until it reaches the level in the tube that corresponds to the level of the bar (which corresponds to the interface or boundary between precipitate and supernatant). At this level, the tip stops taking in fluid, and moves vertically upward and out of the sample tube. In this way, a fluid uptake system can remove essentially all of a sample supernatant.

The sample supernatant can be dispensed into a vessel, or dispensed into another device or chamber of the automated system.

V. Methods of Using Automated Systems for Enriching Rare Cells of a Fluid Sample The present invention also includes methods of enriching rare cells of a fluid sample using an automated system of the present invention. The method includes but is not limited to: introducing a sample into an automated system of the present invention; addition of reagents to sample either before or after the sample is introduced into the system, mixing of sample and reagents; sedimentation of RBCs and removal of undesirable components; collection of supernatant containing desired cells; filtering the sample through at least one filtration chamber of the automated system; and collecting enriched rare cells from at least one vessel or at least one outlet of the automated system.

Sample

A sample can be any fluid sample, such as an environmental sample, including air samples, water samples, food samples, and biological samples, including extracts of biological samples. Biological samples can be blood, a bone marrow sample, an effusion of any type, ascities fluid, pelvic wash fluid, pleural fluid, spinal fluid, lymph, serum, mucus, sputum, saliva, urine, vaginal or uterine washes, semen, occular fluid, extracts of nasal, throat or genital swabs, cell suspension from digested tissue, or extracts of fecal material. Biological samples can also be samples of organs or tissues, including tumors, such as fine needle aspirates or samples from perfusions of organs or tissues. Biological samples can also be samples of cell cultures, including both primary cultures and cell lines. The volume of a sample can be very small, such as in the microliter range, and may even require dilution, or a sample can be very large, such as up to 10 liters for ascites fluid. One preferred sample is a urine sample. Another preferred sample is a blood sample.

A biological sample can be any sample, recently taken from a subject, taken from storage, or removed from a source external to a subject, such as clothing, upholstery, tools, etc. As an example, a blood sample can therefore be an extract obtained, for example, by soaking an article containing blood in a buffer or solution. A biological sample can be unprocessed or partially processed, for example, a blood sample that has been dialyzed, had reagents added to it, etc. A biological sample can be of any volume. For example, a blood sample can be less than five microliters, or more than 5 liters, depending on the application. Preferably, however, a biological sample that is processed using the methods of the present invention will be from about 10 microliters to about 2 liters in volume, more preferably from about one milliliter to about 250 milliliters in volume, and most preferably between about 5 and 50 milliliters in volume.

Introduction of Sample

In some preferred embodiments of the present invention, one or more samples can be provided in one or more tubes that can be placed in a rack of the automated system. The rack can be automatically or manually engaged with the automated system for sample manipulations.

Alternatively, a sample can be dispensed into an automated system of the present invention by pipeting or injecting the sample through an inlet of an automated system, or can be poured, pipeted, or pumped into a conduit or reservoir of the automated system. In most cases, the sample will be in a tube that provides for optimal separation of sedimented cells, but it can be in any type of vessel for holding a liquid sample, such as a plate, dish, well, or chamber.

Prior to the dispensing of a sample into a vessel or chamber of the automated system, solutions or reagents can optionally be added to the sample. Solutions or reagents can optionally be added to a sample before the sample is introduced into an automated system of the present invention, or after the sample is introduced into an automated system of the present invention. If a solution or reagent is added to a sample after the sample is introduced into an automated system of the present invention, it can optionally be added to the sample while the sample is contained within a tube, vessel, or reservoir prior to its mixing or incubation step, the settling step, or its introduction into a filtration chamber. Alternatively, a solution or reagent can be added to a sample through one or more conduits, such as tubing, where the mixing of sample with a solution or reagent takes place in conduits. It is also possible to add one or more solutions or reagents after the sample is introduced into a chamber of the present invention (such as, but not limited to, a filtration chamber), by adding one or more of these directly to the chamber, or through conduits that lead to the chamber.

The sample (and, optionally, any solutions, or reagents) can be introduced into the automated system by positive or negative pressure, such as by a syringe-type pump. The sample can be added to the automated system all at once, or can be added gradually, so that as a portion of the sample is being filtered, additional sample is added. A sample can also be added in batches, such that a first portion of a sample is added and filtered through a chamber, and then further batches of a sample are added and filtered in succession.

Combined Solution for Sedimenting Red Blood Cells and Selectively Removing Undesirable Sample Components of a Blood Sample In preferred embodiments of the present invention, a solution that sediments red blood cells can also include one or more additional specific binding members that can be used to selectively remove undesirable sample components other than red blood cells from the blood sample. In this regard, the present invention includes a combined sedimenting solution for enriching rare cells of a blood sample that sediments red blood cells and provides reagents for the removal of other undesirable components of the sample. Thus a combined solution for processing a blood sample comprises: dextran; at least one specific binding member that can induce agglutination of red blood cells; and at least one additional specific binding member that can specifically bind undesirable components of the sample other than RBCs.

Addition of Sedimenting Solution to Sample

A red blood cell sedimenting solution can be added to a blood sample by any convenient means, such as pipeting, automatic liquid uptake/dispensing devices or systems, pumping through conduits, etc. The amount of sedimenting solution that is added to a blood sample can vary, and will largely be determined by the concentration of dextran and specific binding members in the sedimenting solution (as well as other components), so that their concentrations will be optimal when mixed with the blood sample. Optimally, the volume of a blood sample is assessed, and an appropriate proportional volume of sedimenting solution, ranging from 0.01 to 100 times the sample volume, preferably ranging from 0.1 times to 10 times the sample volume, and more preferably from 0.25 to 5 times the sample volume, and even more preferably from 0.5 times to 2 times the sample volume, is added to the blood sample. (It is also possible to add a blood sample, or a portion thereof, to a red blood cell sedimenting solution. In this case, a known volume of sedimenting solution can be provided in a tube or other vessel, and a measured volume of a blood sample can be added to the sedimenting solution.)

Specific Binding Member for Removing Undesirable Components

In addition to the components of a sedimenting solution of the present invention, a combined solution of the present invention can comprise at least one specific binding member that can selectively bind undesirable components of a blood sample (including but not limited to red blood cells, white blood cells, platelets, serum proteins) and have less binding to desirable components. One or more specific binding members that can selectively bind undesirable components of a sample can be used to remove the undesirable components of the sample, increasing the relative proportion of rare cells in the sample, and thus contribute to the enrichment of rare cells of the sample. By "selectively binds" is meant that a specific binding member used in the methods of the present invention to remove one or more undesirable sample components does not appreciably bind to desirable cells of the sample. By "does not appreciably bind" is meant that not more than 30%, preferably not more than 10%, and more preferably not more than 1.0% of one or more desirable cells are bound by the specific binding member used to remove undesirable components from the sample. In many cases, the undesirable components of a blood sample will be white blood cells. In preferred embodiments of the present invention, a combined solution of the present invention can be used for sedimenting red blood cells and selectively removing white blood cells from a blood sample.

A specific binding member that can specifically bind white blood cells can be as nonlimiting examples, an antibody, a ligand for a receptor, transporter, channel or other moiety of the surface of a white blood cell, or a lectin or other protein that can specifically bind particular carbohydrate moieties on the surface of a white blood cell (for example, sulfated Lewis-type carbohydrates, glycolipids, proteoglycans or selectin).

Preferably, a specific binding member that selectively binds white blood cells is an antibody that binds white blood cells but does not appreciably bind fetal nucleated cells, such as, for example, an antibody to CD3, CD11b, CD14, CD17, CD31, CD45, CD50, CD53, CD63, CD69, CD81, CD84, CD102, or CD166. Antibodies can be purchased commercially from suppliers such as, for example Dako, BD Pharmingen, Antigenix America, Neomarkers, Leinco Technologies, Research & Diagnostic Systems, Serotec, United States Biological, Bender Medsystems Diagnostics, Ancell, Leinco Technologies, Cortex Biochem, CalTag, Biodesign, Biomeda, Accurate Chemicals & Scientific and Chemicon International. Antibodies can be tested for their ability to bind an efficiently remove white blood cells and allow for the enrichment of desirable cells from a sample using capture assays well known in the art.

Specific binding members that selectively bind to one or more undesirable components of the present invention can be used to capture one or more undesirable components, such that one or more desirable components of the fluid sample can be removed from the area or vessel where the undesirable components are bound. In this way, the undesirable components can be separated from other components of the sample that include the rare cells to be separated. The capture can be affected by attaching the specific binding members that recognize the undesirable component or components to a solid support, or by binding secondary specific binding members that recognize the specific binding members that bind the undesirable component or components, to a solid support, such that the undesirable components become attached to the solid support. In preferred embodiments of the present invention, specific binding members that selectively bind undesirable sample components provided in a combined solution of the present invention are coupled to a solid support, such as microparticles, but this is not a requirement of the present invention.

Magnetic beads are preferred solid supports for use in the methods of the present invention to which specific binding members that selectively bind undesirable sample components can be coupled. Magnetic beads are known in the art, and are available commercially. Methods of coupling molecules, including proteins such as antibodies, lectins and avidin and its derivatives, to microparticles such as magnetic beads are known in the art. Preferred magnetic beads of the present invention are from 0.02 to 20 microns in diameter, preferably from 0.05 to 10 microns in diameter, and more preferably from 0.05 to 5 microns in diameter, and even more preferably from 0.05 to 3 microns in diameter and are preferably provided in a combined solution of the present invention coated with a primary specific binding member, such as an antibody that can bind a cell that is to be removed from the sample, or a secondary specific binding member, such as streptavidin or neutravidin, that can bind primary specific binding members that bind undesirable sample components (such as biotinylated primary specific binding members).

In preferred embodiments of the present invention, the fluid sample is a maternal blood sample, the rare cells whose separation are desirable are fetal cells, and the undesirable components of the sample to be removed from the sample are white blood cells and other serum components. In these embodiments, a specific binding member that selectively binds white blood cells is used to remove the white blood cells from the sample by magnetic capture. Preferably, the specific binding member provided is attached to magnetic beads for direct capture, or, is provided in biotinylated form for indirect capture of white blood cells by streptavidin-coated magnetic beads.

A combined solution for enriching rare cells of a blood sample of the present invention can also include other components, such as, but not limited to, salts, buffering agents, agents for maintaining a particular osmolality, chelators, proteins, lipids, small molecules, anticoagulants, etc. For example, in some preferred aspects of the present invention, a combined solution comprises physiological salt solutions, such as PBS, PBS lacking calcium and magnesium or Hank's balanced salt solution. In some preferred aspects of the present invention, EDTA or heparin or ACD are present to prevent red blood cell clotting.

Mixing

The blood sample and red blood cell sedimenting solution are mixed so that the chemical RBC aggregating agent (such as a polymer, such as, for example, dextran) and one or more specific binding members of the sedimenting solution, as well as the components of the blood sample are distributed throughout the sample vessel. Mixing can be achieved means such as electrically powered acoustic mixing, stirring, rocking, inversion, agitation, etc., with methods such as rocking and inversion, that are least likely to disrupt cells, being favored.

Incubation of Blood Sample and Sedimenting Solution

The sample mixed with sedimenting solution is allowed to incubate to allow red blood cells to sediment. Preferably the vessel comprising the sample is stationary during the sedimentation period so that the cells can settle efficiently. Sedimentation can be performed at any temperature from about 5° C. to about 37° C. In most cases, it is convenient to perform the steps of the method from about 15° C. to about 27° C. The optimal time for the sedimentation incubation can be determined empirically for a given sedimenting solution, while varying such parameters as the concentration of dextran and specific binding members in the solution, the dilution factor of the blood sample after adding the sedimenting solution, and the temperature of incubation. Preferably, the sedimentation incubation is from five minutes to twenty four hours in length, more preferably from ten minutes to four hours in length, and most preferably from about fifteen minutes to about one hour in length. In some preferred aspects of the present invention, the incubation period is about thirty minutes.

Filtering the Sample Through a Chamber of the Automated System

A sample can be filtered in an automated system of the present invention before or after undergoing one or more debulking steps or one or more separation steps. These debulking or separation steps can include but are not limited to a RBC sedimentation step or removal by specific binding members. The sample can be directly transferred to a filtration chamber (such as by manual or automated dispensing) or can enter a filtration chamber through a conduit. After a sample is added to a filtration chamber, it is filtered to reduce the volume of the sample, and, optionally, to remove undesirable components of a sample. To filter the sample, fluid flow is directed through the chamber. Fluid flow through the chamber is preferably directed by automatic rather than manual means, such as by an automatic syringe-type pump. The pump can operate by exerting positive or negative pressure through conduits leading to the filtration chamber. The rate of fluid flow through a filtration chamber can be any rate that allows for effective filtering, and for a whole blood sample is preferably between about one and about 1000 milliliters per hour, more preferably between about five and about 500 milliliters per hour, and most preferably between about ten and about fifty milliliters per hour. Following the addition of a sample to a filtration chamber, a pump or fluid dispensing system can optionally direct fluid flow of a buffer or solution into the chamber to wash additional filterable sample components through the chamber.

When the sample is added to the filtration chamber, and fluid flow is directed through the chamber, pores or slots in the filter or filters can allow the passage of fluid, soluble components of the samples, and some non-soluble components of a fluid sample through one or more filters, but, because of their dimensions, can prevent the passage of other components of the fluid sample through the one or more filters.

For example, in preferred embodiments a fluid sample can be dispensed into a filtration chamber that comprises at least one filter that comprises a plurality of slots. The chamber can have ports that are optionally connected to conduits through which a buffer or solution and the fluid sample or components thereof can flow. When the sample is added to the chamber, and fluid flow is directed through the chamber, the slots can allow the passage of fluid and, optionally, some components of a fluid sample through the filter, but prevent the passage of other components of the fluid sample through the filter.

In some embodiments of the present invention, an active chip that is part of the filtration chamber can be used to mix the sample during the filtration procedure. For example, an active chip can be an acoustic chip that comprises one or more acoustic elements. When an electric signal from a power supply activates the acoustic elements, they provide vibrational energy that causes mixing of the components of a sample. An active chip that is part of a filtration chamber of the present invention can also be a dielectrophoresis chip that comprises microelectrodes on the surface of a filter. When an electric signal from a power supply is transmitted to the electrodes, they provide a negative dielectrophoretic force that can repel components of a sample from the filter surface. In this embodiment, the electrodes on the surface of the filter/chip are preferably activated intermittently, when fluid flow is halted or greatly reduced.

Mixing of a sample during filtration is performed to avoid reductions in the efficiency of filtration based on aggregation of sample components, and in particular their tendency to collect, in response to fluid flow through the chamber, at positions in the chamber where filtering based on size or shape occurs, such as dams, slots, etc. Mixing can be done continuously through the filtration procedure, such as through a continuous activation of acoustic elements, or can be done in intervals, such as through brief activation of acoustic elements or electrodes during the filtration procedure. Where dielectrophoresis is used to mix a sample in a filtration chamber, preferably the dielectrophoretic force is generated in short intervals (for example, from about two seconds to about 15 minutes, preferably from about two to about 30 seconds in length) during the filtration procedure; for example, pulses can be given every five seconds to about every fifteen minutes during the filtration procedure, or more preferably between about every ten seconds to about every one minute during the filtration procedure. The dielectrophoretic forces generated serve to move sample components away from features that provide the filtering function, such as, but not limited to, slots.

During the filtration procedure, filtered sample fluid can be removed from the filtration chamber by automated fluid flow through conduits that lead to one or more vessels for containing the filtered sample. In preferred embodiments, these vessels are waste receptacles. After filtration, fluid flow can optionally be directed in the reverse direction through the filter to suspend retained components that may have settled or lodged against the filter.

After the filtration procedure (and optionally, a mixing and incubation with one or more specific binding members), sample components that remain in the filtration chamber after the filtration procedure can be directed out of the chamber through additional ports and conduits that can lead to collection tubes or vessels or to other elements of the automated system for further processing steps, or can be removed from the filtration chamber or a collection vessel by pipeting or a fluid uptake means. Ports can have valves or other mechanisms for controlling fluid flow. The opening and closing of ports can be automatically controlled. Thus, ports that can allow the flow of debulked (retained) sample out of a filtration chamber (such as to other chambers or collection vessels) can be closed during the filtration procedure, and conduits that allow the flow of filtered sample out of a filtration chamber can optionally be closed after the filtration procedure to allow efficient removal of remaining sample components.

Further Enrichment of Desired Cells

Selective Removal of Undesirable Components of a Sample

Optionally, sample components that remain in the filtration chamber either before, during, or after the filtration procedure can be directed by fluid flow to an element of the automated system in which undesirable components of a sample can be separated from the sample. In some embodiments of the present invention, prior to either adding the sample to the filtration chamber or removing the debulked sample retained in the filtration chamber, one or more specific binding members can be added to the debulked sample and either mixed before the and afterwards in the filtration chamber, using, for example, one or more active chips that engage or are a part of the filtration chamber to provide physical forces for mixing. Preferably, one or more specific binding member is added to the debulked sample in the filtration chamber, ports of the chamber are closed, and acoustic elements are activated either continuously or in pulsed, during the incubation of debulked sample and specific binding members. Preferably, one or more specific binding members are antibodies that are bound to magnetic beads. The specific binding members can be antibodies that bind desirable sample components, such as fetal nucleated cells, but preferably the specific binding members are antibodies that bind undesirable sample components, such as white blood cells while having minimal binding to desirable sample components.

In preferred embodiments of the present invention, sample components that remain in the filtration chamber after the filtration procedure are incubated with magnetic beads, and following incubation, are directed by fluid flow to a separation column. Preferably, a separation column used in the methods of the present invention is a cylindrical glass, plastic, or polymeric column with a volumetric capacity of between about one milliliter and ten milliliters, having entry and exit ports at opposite ends of the column. Preferably, a separation column used in the methods of the present invention comprises or can be positioned alongside at least one magnet that runs along the length of the column. The magnet can be a permanent magnet, or can be one or more electromagnetic units on one or more chips that is activated by a power source.

Sample components that remain in the filtration chamber after the filtration procedure can be directed by fluid flow to a separation column. Reagents, preferably including a preparation of magnetic beads, can be added to the sample components before or after they are added to the chamber. Preferably, reagents are added prior to transfer of sample components to a separation chamber. Preferably a preparation of magnetic beads added to the sample comprises at least one specific binding member, preferably a specific binding member that can directly bind at least one undesirable component of the sample. However, it is also possible to add a preparation of magnetic beads that comprise at least one specific binding member that can indirectly bind at least one undesirable component of the sample. In this case, it is necessary to also add a primary specific binding partner that can directly bind undesirable components to the sample. A primary specific binding partner is preferably added to the sample before the preparation of magnetic beads comprising a secondary specific binding partner is added to the sample, but this is not a requirement of the present invention. Bead preparations and primary specific binding partners can be added to a sample before or after the addition of the sample to a separation column, separately or together.

In embodiments where magnetic beads comprise primary specific binding members, the sample and magnetic bead preparation are preferably incubated together for between about five and about sixty minutes before magnetic separation. In embodiments where a separation column comprises or is adjacent to one or more permanent magnets, the incubation can occur prior to the addition of the sample to the separation column, in conduits, chambers, or vessels of the automated system. In embodiments where a separation column comprises or is adjacent to one or more current-activated electromagnetic elements, the incubation can occur in a separation column, prior to activating the one or more electromagnetic elements. Preferably, however, incubation of a sample with magnetic beads comprising specific binding members occurs in a filtration chamber following filtration of the sample, and after conduits leading into and out of the filtration chamber have been closed.

Where magnetic beads comprising secondary specific binding members are employed, optionally more than one incubation can be performed (for example, a first incubation of sample with a primary specific binding member, and a second incubation of sample with beads comprising a secondary specific binding member). Separation of undesirable components of a sample can be accomplished by magnetic forces that cause the electromagnetic beads that directly or indirectly bind the undesirable components. This can occur when the sample and magnetic beads are added to the column, or, in embodiments where one or more electromagnetic units are employed, by activating the electromagnetic units with a power supply. Noncaptured sample components can be removed from the separation column by fluid flow. Preferably, noncaptured sample components exit the column through a portal that engages a conduit.

Separation of Desirable Components

After filtering, a sample can optionally be directed by fluid flow to a separation chamber for the separation of rare cells.

In preferred aspects in which undesirable components of a debulked sample have been removed in a separation column, the debulked sample is preferably but optionally transferred to a second filtration chamber prior to being transferred to a separation chamber for separation rare cells of the sample. A second filtration chamber allows for further reduction of the volume of a sample, and also optionally allows for the addition of specific binding members that can be used in the separation of rare cells and mixing of one or more specific binding members with a sample. Transfer of a sample from a separation column to a separation chamber is by fluid flow through conduits that lead from a separation column to a second filtration chamber. A second filtration chamber preferably comprises at least one filter that comprises slots, and fluid flow through the chamber at a rate of between about one and about 500 milliliters per hour, more preferably between about two and about 100 milliliters per hour, and most preferably between about five and about fifty milliliters per hour drives the filtration of sample. In this way, the volume of a debulked sample from which undesirable components have been selectively removed can be further reduced. A second filtration chamber can comprise or engage one or more active chips. Active chips, such as acoustic chips or dielectrophoresis chips, can be used for mixing of the sample prior to, during, or after the filtration procedure.

A second filtration chamber can also optionally be used for the addition of one or more reagents that can be used for the separation of rare cells to a sample. After filtration of the sample, conduits that carry sample or sample components out of the chamber can be closed, and one or more conduits leading into the chamber can be used for the addition of one or more reagents, buffers, or solutions, such as, but not limited to, specific binding members that can bind rare cells. The one or more reagents, buffers, or solutions can be mixed in the closed-off separation chamber, for example, by activation of one or more acoustic elements or a plurality of electrodes on one or more active chips that can produce physical forces that can move components of the sample and thus provide a mixing function. In preferred aspects of the present invention, magnetic beads that are coated with at least one antibody that recognizes a rare cell are added to the sample in the filtration chamber. The magnetic beads are added via a conduit, and are mixed with the sample by activation of one or more active chips that are integral to or engage a second filtration chamber. The incubation of specific binding members with a sample can be from about five minutes to about two hours, preferably from about eight to about thirty minutes, in duration, and mixing can occur periodically or continuously throughout the incubation.

It is within the scope of the present invention to have a second filtration chamber that is not used for the addition and mixing of one or more reagents, solutions, or buffers with a sample. It is also within the scope of the present invention to have a chamber that precedes a separation chamber for the separation of rare cells that can be used for the addition and mixing of one or more reagents, solutions, or buffers with a sample, but that does not perform a filtering function. It is also within the scope of the present invention to have a sample transferred from a separation column to a separation chamber, without an intervening filtration or mixing chamber. In aspects where the methods are directed toward the separation of rare cells from a blood sample, however, the use of a second filtration chamber that is also used for the addition and mixing of one or more reagents with a sample is preferred.

Sample is transferred to a separation chamber by fluid flow. Preferably, a separation chamber for the separation of rare cells comprises or engages at least one active chip that can perform a separation. Such chips comprise functional elements that can, at least in part, generate physical forces that can be used to move or manipulate sample components from one area of a chamber to another area of a chamber. Preferred functional elements of a chip for manipulating sample components are electrodes and electromagnetic units. The forces used to translocate sample components on an active chip of the present invention can be dielectrophoretic forces, electromagnetic forces, traveling wave dielectrophoretic forces, or traveling wave electromagnetic forces. An active chip used for separating rare cells is preferably part of a chamber. The chamber can be of any suitable material and of any size and dimensions, but preferably a chamber that comprises an active chip used for separating rare cells from a sample (a "separation chamber") has a volumetric capacity of from about one microliter to ten milliliters, more preferably from about ten microliters to about one milliliter.

In some embodiments of the present inventions, the active chip is a dielectrophoresis or travelling wave dielectrophoresis chip that comprises electrodes. Such chips and their uses are described in U.S. application Ser. No. 09/973,629, entitled "An Integrated Biochip System for Sample Preparation and Analysis", filed Oct. 9, 2001; U.S. application Ser. No. 09/686,737, filed Oct. 10, 2000 entitled "Compositions and Methods for Separation of Moieties on Chips", U.S. application Ser. No. 09/636,104, filed Aug. 10, 2000, entitled "Methods for Manipulating Moieties in Microfluidic Systems"; and U.S. application Ser. No. 09/679,024, entitled "Apparatuses Containing Multiple Active Force Generating Elements and Uses Thereof" filed Oct. 4, 2000; all incorporated by reference. Rare cells can be separated from a sample of the present invention by, for example, their selective retention on a dielectrophoresis chip, and fluid flow can remove non-retained components of the sample.

In other preferred embodiments of the present invention, the active chip is an electromagnetic chip that comprises electromagnetic units, such as, for example, the electromagnetic chips described in U.S. Pat. No. 6,355,491 entitled "Individually Addressable Micro-Electromagnetic Unit Array Chips" issued Mar. 12, 2002 to Zhou et al., U.S. application Ser. No. 09/955,343, filed Sep. 18, 2001, entitled "Individually Addressable Micro-Electromagnetic Unit Array Chips", and U.S. application Ser. No. 09/685,410, filed Oct. 10, 2000, entitled "Individually Addressable Micro-Electromagnetic Unit Array Chips in Horizontal Configurations". Electromagnetic chips can be used for separation by magnetophoresis or traveling wave electromagnetophoresis. In preferred embodiments, rare cells can be incubated, before or after addition to a chamber that comprises an electromagnetic chip, with magnetic beads comprising specific binding members that can directly or indirectly bind the rare cells. Preferably, in embodiments where rare cells are captured on an electromagnetic chip, the sample is mixed with the magnetic beads comprising a specific binding member in a mixing chamber. Preferably, a mixing chamber comprises an acoustic chip for the mixing of the sample and beads. The cells can be directed through conduits from the mixing chamber to the separating chamber. The rare cells can be separated from the fluid sample by magnetic capture on the surface of the active chip of the separation chamber, and other sample components can be washed away by fluid flow.

The methods of the present invention also include embodiments in which an active chip used for separation of rare cells is a multiple-force chip. For example, a multiple-force chip used for the separation of rare cells can comprise both electrodes and electromagnetic units. This can provide for the separation of more than one type of sample component. For example, magnetic capture can be used to isolated rare cells, while negative dielectrophoresis is used to remove undesirable cells from the chamber that comprises the multiple-force chip.

After the removal of undesirable sample components from the separation chamber, either through active physical forces such as negative dielectrophoresis or by fluid flow, the captured rare cells can be recovered by removing the physical force that causes them to adhere to the chip surface, and collecting the cells in a vessel using fluid flow.

EXAMPLES

Example 1

Fabrication of a Filter for Removing Red Blood Cells from a Blood Sample

A silicon chip of dimensions (1.8 cm by 1.8 cm×500 micron) was used to fabricate a filtration area of 1 cm by 1 cm by 50 micron with slots having dimensions from about 0.1 micron to about 1000 microns, preferably from about 20 to 200 microns preferably from about 1 to 10 microns, more preferably 2.5 to 5 microns. The slots were vertically straight with a maximum tapered angle of less than 2%, preferably less than about 0.5% with an offset distance between neighboring columns of the filter slots were 1 to 500 microns, preferably from 5 to 30 microns.

Manufacturing included providing a silicon chip having the above referenced dimensions and coating the top and bottom of the silicon chip with a dielectric layer. A cavity along the bottom portion of the chip was then created. The cavity was formed by removing an appropriate cavity pattern from the dielectric layer then etching the silicon chip generally following the pattern until desired thickness is reached. The chip was reoxidized to coat the contoured region. A filter pattern was then removed from the dielectric layer coating the top of the silicon chip in substantial alignment (above) with the cavity. The silicon chip was etched (e.g. via deep RIE or ICP processes) at the above referenced angles starting at the pattern created along the top of the chip until the silicon layer has been etched through. The dielectric layer from the top and bottom were then removed. By removing the dielectric layer within the cavity, throughbores, referred to as slots, were created. It is also possible to create these slots using laser cuts to bore though materials, including but not limited to silica or polymers such as plastic.

Example 2

Chemical Treatment of a Microfabricated Filter

A filter chip made as described in Example 1 was placed on a ceramic heating plate in an oven and heated at 800 degrees Celsius for 2 hours in oxygen containing gas (e.g. air). The heating source was then turned off the chips are slowly cooled overnight. This results in a thermally grown layer on the surface of the chip.

A nitride layer could also be deposited onto the filter surface. An oxide layer is put on the surface of the chip by low-pressure chemical vapor deposition (LPCVD) in a reactor at temperatures up to ~900° C. The deposited film is a product of a chemical reaction between the source gases supplied to the reactor. The process is typically performed on both sides of the substrate at the same time to form a layer of $Si_3N_4$.

Example 3

Polyvinylpyrrolidone (PVP) and Polyvinyl Alcohol (PVA) Filter Coatings

Filter chips made by the method of Example 1 were coated with either PVP or PVA. For coating the chips with either PVP or PVA, the chips were pre-treated as follows: The filter chips were rinsed with deionized water and then immersed in 6N nitric acid. The chips were placed on a shaker for 30 minutes at 50 degrees Celsius. After acid treatment, the chips were rinsed in deionized water.

For PVP coating, chips were immersed in 0.25% polyvinylpyrrolidone (K-30) at room temperature until the chips were ready for use. Chips were then rinsed with deionized water and dried by pressurized air.

For PVA coating, after acid treatment and rinsing in water, the chips were stored in water prior to coating. To make the 0.25% PVA (Mn 35,000-50,000) solution, dissolve the PVA in water under slow heating to 80 degrees Celsius and gentle stirring. To coat, the chips were immersed in a hot PVA solution and heated for 1-2 hours. The chips were then rinsed in deionized water and dried by pressurized air.

Example 4

Bovine Serum Albumin (BSA) Filter Coating

For coating filter chips with BSA, the chips were pre-treated as follows: The filter chips were rinsed with deionized water and then immersed in 95% ethanol for 10 seconds at room temperature and then were rinsed again in deionized water.

The chips were then immersed in 2. % BSA in PBS for 2 minutes at room temperature. Chips were then rinsed with deionized water and dried by pressurized air.

Example 5

PEG Filter Coating

To conjugate PEG to the chip surfaces, filter chips were immersed in a solution of DBE-814 (a PEG solution containing polysiloxane from Gelest, Morrisville, Pa.) in 5% methylene chloride. The immersed chips were heated at 70 degrees Celsius for 3 hours under vacuum. After the incubation, the PEG-coated chips were rinsed in deionized water and dried by pressurized air.

Example 6

Procedure for Enriching Fetal Cells from Maternal Blood

We developed a two-step procedure for enrichment of fetal cells from maternal blood.
Step One: Blood Debulking and WBC Removal.
(1) A Combined Reagent:
The combined reagent has two components:
a) RBC aggregation solution
2% Dextran (110,000 MW)
0.05 ugs/ml of IgM antibody to glycophorin A
5 mM EDTA
1×PBS without calcium and magnesium.
The RBC aggregation solution works with heparin or ACD instead of EDTA. The RBC aggregation solution also works with a base solution including but not limited to 1× Hanks balanced saline solution with heparin, ACD, or EDTA. The concentration of IgM antibody to glycophorin A can vary from 0.05 to 0.15 (range of 0.01 to 10) ug/ml.

b) WBC depletion solution
Magnetic beads (1.0 micron magnetic beads prepared by AVIVA), precoated with antibody (5-60 ugs per $10^9$ beads)
The combined reagent has the RBC aggregation solution with 30 (range of 5-60) antibody precoated magnetic beads per WBC and can include but not limited to magnetic beads precoated with antibodies or other reagents to specifically bind other components of blood.
(2) Use of the Combined Reagent:
The combined reagent was added to an equal volume of washed peripheral blood and incubated with rotation for 0.5 hr (range of 0.1-2 hours). The tube was settled for 0.5 hr (range of 0.1 to 2 hrs) upright against a magnet (Dynal, MPC-1). We have also tested a magnet on the bottom of the tube as well.
The solution from the top portion of the tube that did not include aggregated or magnetically captured cells (on the side of the tube or at the bottom portion of the tube) was aspirated off and transferred to a new tube.
Step Two: Further Enrichment of Nucleated Cells and Removal of RBCs.
The aspirated solution can be then further processed to enrich for nucleated fetal cells and remove RBCs by either a magnetic separation step (antibody to CD71 with MACS microbeads) or a microfiltration step. [Table 10] shows the results of using the above described first step followed by CD71 antibody capture of fetal cells. [Table 10] (below) shows the results of using a combined solution (step one described above) followed by microfiltraton.

TABLE 10 nRBC recovery comparing CD71 vs filter chip.

| Experiment | Comparing CD71 and Silicon Membrane for capture fetal nRBC |
| Samples | MB24479, 11 wk gestation presurgery, MB24481, 12 wk gestation drawn and arrived on Jun. 25, 2002. |
| Date | Jun. 25, 2002 |

| Prepacyte | Sample 1 | Sample 2 | Sample 3 | Sample 4 |
| --- | --- | --- | --- | --- |
| | Procedure and Results | | | |
| Number of times washed | 3 | 3 | 3 | 3 |
| Sample name | MB24479 | MB24479 | MB24481 | MB24481 |
| Sex of fetus | Male | Male | Female | Female |
| Number of WBC/ml | 9.60E+06 | 9.60E+06 | 9.40E+06 | 9.40E+06 |
| Start samples in mls | 10 | 10 | 10 | 10 |
| PBS with EDTA | 8 | 8 | 8 | 8 |
| 10% Dextrans110 in PBS-EDTA | 2 | 2 | 2 | 2 |
| IgM GpA | 0.5 µg | 0.5 µg | 0.5 µg | 0.5 µg |
| Bead Manufactor | | Aviva | | |
| Beads/WBC | 30 | 30 | 30 | 30 |
| Bead Lot | Apr. 24, 2002 NAV beads with 30 µg CD50 biotin/1 × 10^9 beads | Apr. 24, 2002 NAV beads with 30 µg CD50 biotin/1 × 10^9 beads | Apr. 24, 2002 NAV beads with 30 µg CD50 biotin/1 × 10^9 beads | Apr. 24, 2002 NAV beads with 30 µg CD50 biotin/1 × 10^9 beads |
| Rock | | 30 min at RT in one 50 ml conical and 5 ml tube | | |
| Stand | | 30 min at RT with a magnet | | |
| Standing Magnet Sep | | Dynal Magnet | | |
| wash | 2× @ 1200 rpm | | 2× @ 1200 rpm | |
| | CD71 enrichment or Silicon Membrane | | | |
| volume | 1 ml | Taiwan silicon membrane 11_2 at flow rate of 20 mls per hour with a magnetic trap | 1 ml | Taiwan silicon membrane 11_2 at flow rate of 20 mls per hour with a magnetic trap |
| CD71 | 0.1 µg | | 0.1 µg | |
| Time/Tem | 15 min at RT | | 15 min at RT | |
| Step 2: add beads | | | | |
| volume | 1 ml | | 1 ml | |
| MAC SAV Beads | 100 µl | | 100 µl | |
| Time/Tem | 15 min at RT | | 15 min at RT | |
| Total Cells Remaining | 7.00E+05 | 6.60E+05 | 6.80E+05 | 8.80E+05 |
| slides proposed to make | 7 | 6 | 7 | 8 |
| Actual sides made | 7 | 6 | 7 | 8 |
| nRBCs counted | 4, 3, 0 | 3, 3 | 0, 4, 2 | 4, 2 |
| estimated total nRBC | 16 | 18 | 14 | 24 |

Example 7

Process Flow Chart for Enriching Nucleated Fetal Cells from Maternal Blood

Figure 13:
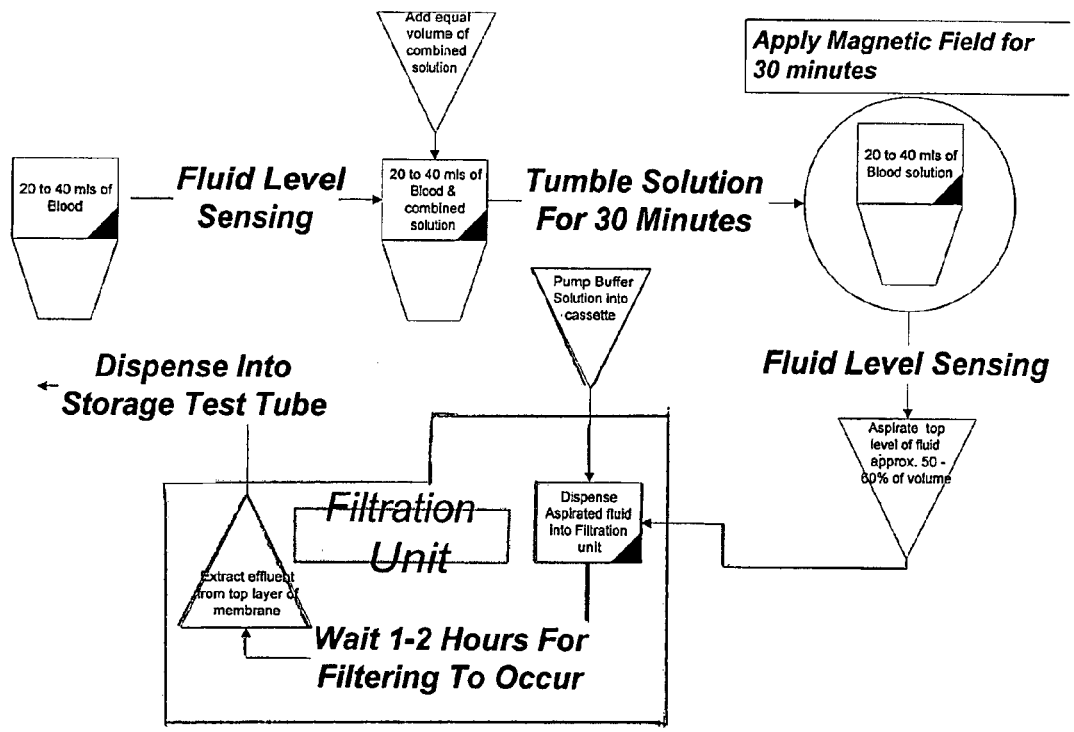
FIG. 13 shows a process flow chart for enriching fetal nucleated RBCs from maternal blood.

FIG. 13 shows a process flow chart for enriching fetal nucleated cells from maternal blood samples. The whole process comprises the flowing steps:
(1) The blood sample may be transferred to a centrifuge tube.
(2) The sample does not have to be but can be washed before addition to the automated unit.
(3) The process starts with a volume of blood sample 10 mls (range of 3-40 ml) in a tube(s).
(4) Fluidic level sensing step is used to determine the exact volume of the blood sample in the tube to be processed.
(5) Add a volume of the combined reagent (for example, an equal volume of the reagent described in Example 6) to the blood sample in the tube.
(6) Rotate/shake/tumble/mix the solution for a period of time 0.5 hrs (range of 0.1-2 hrs).
(7) Let the solutions in the tube settle upright for 30 minutes (range of 0.1 to 2 hrs) so that the aggregated RBCs can settle to the bottom of the tube. Simultaneously during this period, a magnetic field is applied to collect and attract magnetic beads (which may or may not have bound blood components) to a side of tube.
(8) Another fluidic level sensing step is applied to determine what the volume of the "un-aggregated" cell suspension is present in the tube.
(9) Aspirate appropriate volume of the fluid from the tube into the fetal cell filtration chamber (or fetal cell cassette process).
(10) Filter the sample for 0.2-2 hr in the fetal cell filtration chamber/cassette (Further details of the filtration process are included in [Example 9], below.)
(11) Extract solution from the top chamber of the filtration cassette and dispense into storage test tube.

Example 8

Process Flow Chart for Silicon Membrane Filtration Process

FIG. 14 provides a schematic diagram showing the microfiltration process. The simplified process steps include the following:
(1) Close valves B&D, open valves A&C.
(2) Test sample (coming from the first step of the procedure in [Example 10]) is loaded into the 45 mL loading reservoir.
(3) Operate waste pump for 1 h so that the sample loaded in the storage reservoir is filtered through the microfabricated filter.
(4) Apply 1-10 mL wash solution to the Loading Reservoir.
(5) Close valve A, open valve B.
(6) Wash the bottom subchamber with 1-5 mL.
(7) Close valve C and open valve D.
(8) Rotate the Cassette and filtration chamber 180 degrees.
(9) Flush the filter from valve B.
(10) Collect volume from valve D.

Example 9

Use of an Automated System to Isolate Fetal Cells from Maternal Blood

Ten milliliters blood samples of pregnant women (from six to thirty weeks gestation) are washed by diluting the samples with PBE and centrifuged at 470×g for 6 minutes (range of 50-900×g for 3-20 minutes). The supernatants are aspirated off, and PBE is added to the pellets and mixed. The samples are again centrifuged and the supernatants aspirated off. The final pellets are resuspended to the original volume with PBE. Ten milliliters of Combined Reagent (PBS lacking calcium and magnesium containing: 5 millimolar EDTA, 2% dextran (molecular weight from 70 to 200 kilodaltons), 0.05 micrograms (range of 0.01 to ugs) per milliliter of IgM antibodies to glycophorin A, and approximately $1-10 \times 10^9$ precoated magnetic beads are manually added to the sample tubes.

The Rare Cell Isolation Automated System has control circuits for automated processing steps, and plugs into a 110 volt outlet. The tubes containing the samples are placed in a rack of a Rare Cell Isolation Automated System. The tubes are automatically rotated in the Automated System rack for 30 minutes (range between 5 and 120 minutes). The tubes are then allowed to stand upright while a second rack that has a magnet field, which is automatically positioned next to the tube rack. It is also possible to have other types of magnetic fields including but not limited to electromagnetic fields. The tubes are held in the upright position for 30 minutes (range of 5-120 minutes) so that the aggregated RBCs can settle to the bottom of the tube and WBC-magnetic bead aggregates are attracted to the side of each tube that is adjacent to the magnet. After the cells are allowed to settle, the supernatant volume is determined by the automated system using a light transmission-light sensor transparency measuring device.

The transparency measuring device consists of bars that each have a collated light source (the number of bars corresponds to the number of tubes) that can be focused on a sample tube, and a light detector that is positioned on the opposite side of the tube. The light source uses a laser beam that emits light in the infrared range (780 nanometers) and has an intensity greater than 3 milli-watts. The light from the source is focused through the sample tube, and at the other side of the sample tube the light detector having an intensity measurement device records the amount of light that has passed through the sample (the laser output measurement). The bars having the low wattage laser sources and light detectors move upward from a level at the bottom of the tubes. As each laser makes initial contact with the aggregated cells in the corresponding tube, the laser output measurement is zeroed. When the measured intensity for a given tube begins to rise above a threshold valve the vertical movement of the bar stops. The bar then moves to find the exact vertical point at which the transmitted light equals the threshold value. In this way the vertical point position of the aggregated cell/cell supernatant interface is determined. Once this level has been determined, the fluid handling unit moves to a preset location and uses a capacitive sensing routine to find the level of the bar (corresponding to the level of the interface). Using this data, the fluid handling accurately removes the supernatant from the fluid container. The supernatant is automatically dispensed directly into the loading reservoir of the filtration unit.

Figure 23:
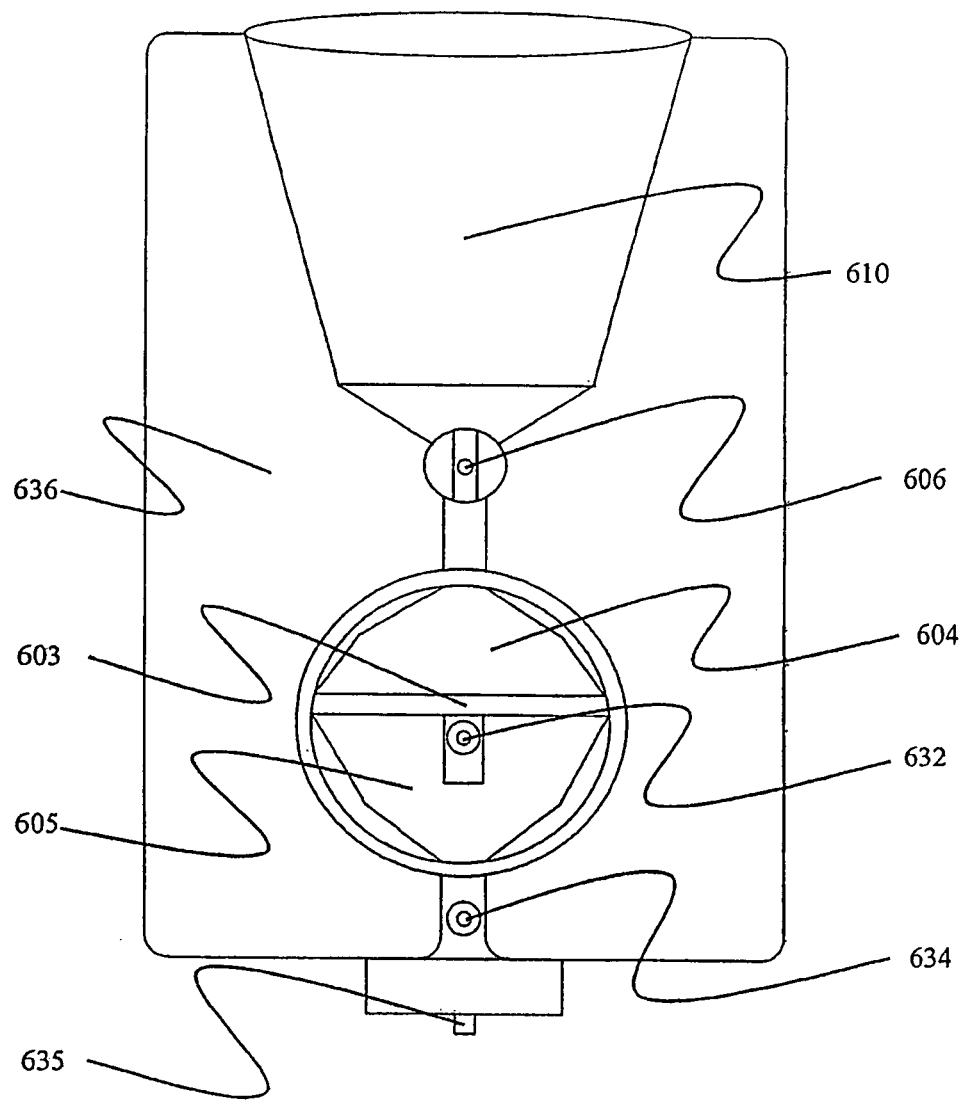
FIG. 23 is a schematic representation of a filtration unit of an automated system of the present invention. The filtration unit has a loading reservoir (610) connected through valve A (606) to a filtration chamber that comprises an antechamber (604) separated from a post-filtration subchamber (605) by a microfabricated filter (603). A suction-type pump can be attached through tubing that connects to the waste port (634), where filtered sample exits the chamber. A side port (632) can be used for attaching a syringe pump for pumping wash buffer through the lower subchamber (605). After the filtration process, the filtration chamber (including the antechamber (604), post-filtration subchamber (605), filter (603), and side port (632), all depicted within the circle in the figure) can rotate within the frame (636) of the filtration unit, so that enriched cells of the antechamber can be collected via the collection port (635).

The following description of the automated separation process performed by the Rare Cell Isolation Automated System uses a filtration unit (filtration chamber, loading reservoir, and associated ports and valves) as depicted in FIG. 23. In this design, the filtration chamber can rotate 180 degrees or more within the filtration unit.

The filtration chamber comprises an antechamber (604) and a postfiltration subchamber (605) separated by a single filter (603). The microfabricated filter measuring 1.8 cm by 1.8 cm and having a filtration area of approximately 1 cm by 1 cm. The filter has approximately 94,000 slots arranged in a parallel configuration as shown in FIG. 2 with the slots having a taper of one to two degrees and dimensions of 3 microns× 100 microns, within a 10% variation in each dimension. The filter slots can have dimensions of 1-10 microns by 10-500 microns with a vertical taper of 0.2 to 10 degrees depending on the target. The thickness of the filter is 50 microns (range of 10-200 microns). The filter is positioned in a two piece filtration chamber with the top half (antechamber) being an approximately rectangular filtration antechamber that tapers upward with a volume of approximately 0.5 milliliters. The bottom post-filtration subchamber is also approximately circular and tapers toward the bottom, also having a volume of approximately 0.5 milliliters. The filter covers essentially the entire bottom area of the (top) antechamber and essentially the entire top area of the (bottom) postfiltration subchamber.

In addition to the filtration chamber, the filtration unit comprises a "frame" having a loading reservoir (610), a valve controlling the flow of sample form the loading reservoir into the filtration chamber ("valve A", 606), and separate ports for the outflow of waste or filtered sample (the waste port, 634) and for the collection of enriched rare cells (the collection port, 635). The post-filtration subchamber (605) comprises a side port (632) that can be used for the addition of buffer, and an outlet that can engage the waste port during filtration for the outflow of waste (or filtered sample). The antechamber (604) comprises an inlet that during filtration can engage the sample loading valve (valve A, 606) and during collection of enriched cells, can engage the collection port (635). During operation of an automated system, the filtration chamber (comprising the antechamber (604), post-filtration subchamber (605), and side port (632)) resides in the frame of the filtration unit.

During filtration, valve A is open, and the outlet of the post-filtration subchamber is aligned with the waste port, allowing a flow path for filtering sample from the loading reservoir through the filtration chamber and to the waste. A syringe pump draws fluid through the chamber at a flow rate of from about 10 to 500 milliliters per hour, depending upon the process step.

Prior to dispensing the appropriate volume of supernatant from each tube into the loading reservoir of the filtration unit, the side port (632) and waste port (634) of the filtration unit are closed, and valve A (606) is opened (see FIG. 23). (When the filtration unit is in the loading/filtering position, the filtration chamber does not engage the collection port (635)). With the side port of the filtration unit open, the unit is filled with PBE from the side port until the buffer reaches the bottom of the sample reservoir. The side port is then closed, and the blood sample supernatant is loaded into the loading reservoir.

Although the Rare Cell Isolation Automated System can separate several samples simultaneously, for clarity, the description of the separation process that follows will describe the filtration of a single sample. To filter a sample, the waste port (634) of a filtration unit is opened, and, using a syringe pump connected through tubing to the waste port, sample supernatant is drawn into and through the filtration chamber. As sample goes through the chamber, the larger cells stay in the top chamber (antechamber) and the smaller cells go through the filter into the lower chamber (post-filtration subchamber) and then through the waste port to the waste. Filtering is performed at a rate of approximately 10-100 milliliters per hour.

After a sample has gone through a filtration chamber (typically after from one half to two hours of filtering), three to five milliliters of PBE are added to the loading reservoir (with valve A remaining open) and pulled through the filtration chamber using the syringe pump connected to the waste port to wash the antechamber and make sure virtually all small cells are washed through.

Valve A (606) is then closed and the side port (632) is opened. Five to ten milliliters of buffer are added from the side port (632) using a syringe pump connected to tubing that is attached to the waste port (634) to wash the bottom post-filtration subchamber. After residual cells have been washed from the post-filtration subchamber (605), the bottom (post-filtration) subchamber is further cleaned by pushing air through the side port (632).

The filter cartridge is then rotated approximately 180 degrees within the filtration unit, so that the antechamber (604) is below the post-filtration subchamber (605). When the chamber rotates into collection position, the outlet of the post-filtration subchamber disengages from the waste port and, as the post-filtration subchamber becomes positioned above the antechamber, the "outlet" becomes positioned at the top of the inverted filtration chamber, but does not engage any openings in the filtration unit, and thus is blocked. As this happens, the antechamber rotates to the bottom of the inverted filtration unit, so that the antechamber inlet disengages from valve A, and instead engages the collection port at the bottom of the filtration unit. During this rotation from the filtering position to the collection position, the side port does not change position. It is aligned with the axis of rotation of the filtration chamber, and remains part of, and a functional port of, the post-filtration subchamber. As a result of this rotation, the filtration chamber is in the collection position. Thus, in the collection position, the post-filtration subchamber, having a side port but now closed off at its outlet, is above the antechamber. The antechamber "inlet" is aligned with and open to the collection port.

Approximately two milliliters of buffer is pumped into the filtration chamber through the side port to collect the cells left in the antechamber. The cells are collected into a vial that attaches to the filtration unit at the site of the sample collection port, or via tubing that leads from the sample collection port and dispenses the sample into a collection tube. Approximately 2 milliliters of additional PBE, and approximately 2 to 5 milliliters of air, is pumped through the side port to clean residual cells off of the filter and into the collection vial. The enriched rare cells can be analyzed microscopically or using any of a number of assays, or can be stored or put into culture.

Example 10

Improved Magnet Configurations for Magnetic Particle Capture

To improve the efficiency of separating components such as cells from liquid samples using capture of magnetic particles to one portion of a tube or other container, several magnet configurations were tested.

Magnets of dimensions ⁹⁄₁₆×1.25×⅛", (Forcefield (Fort Collins, Co) NdFeB block, item #27, Nickel Plate, Br max 12,100 Gauss, Bh max 35 MGOe) were used to test the magnetic field strength. In these experiments, the strongest field could be used to capture magnetic beads that were coated with antibodies that specifically bound white blood cells, and improve the removal of white blood cells from a blood sample compared to commercially available magnetic cell separation unit MPC-1 (Dynal, (Brown Deer, Wis.).

Magnets were attached in several configurations and orientations to a polypropylene stand designed to hold a 50 milliliter tube, as depicted schematically in Figure [X]. The magnetic field in the right, center, and left of the tube was measured by Gauss meter (JobMaster Magnets (Randallstown, Md.) Model GM1 using probe model PT-70, Cal #373).

Example 11

Depletion of Platelets from a Blood Sample with Antibody to Cd31

To remove platelets from a peripheral blood sample, 1.5 to $4\times10^9$ neutravidin coated magnetic beads (AVIVA Biosciences Corp) were coated with 75 micrograms of biotinylated CD31 antibody (AVIVA Systems Biology). The beads were washed and resuspended in PBE (PBS containing 0.5% BSA and 5 mM EDTA) to a concentration of $4\times10^9$ beads per milliliter.

For each 10 milliliter of washed blood sample, 1.5 to $4\times10^9$ of CD31-coated magnetic beads were used. The beads were added to 10 milliliters of washed blood sample in a 50 milliliter polypropylene tube. The tube was rotated for 30 minutes (range of 5 to 120 minutes) and then placed in a stand having one or more magnets positioned along the outside of the tube. After thirty minutes (range of 5 to 120 minutes), the supernatant was removed.

Figure 25:
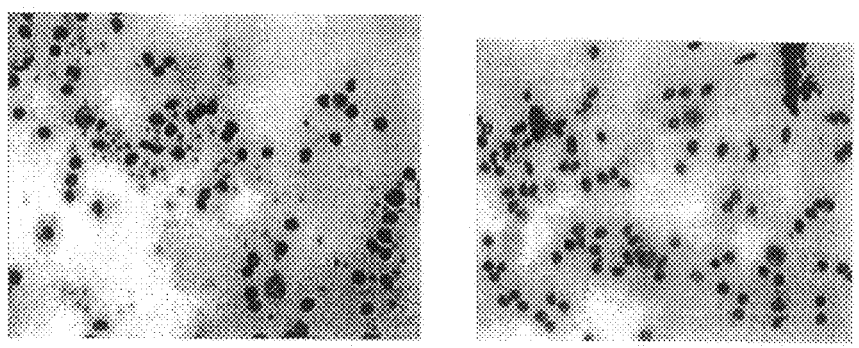
FIG. 25 is a photograph of a slide containing a control (FIG. 25A) and a platelet depleted blood sample (FIG. 25B). The slides were stained with a Benzidine Wright-Giemsa staining protocol.

The samples were filtrated using a micro-fabricated filter and the cells were recovered. The cells were resuspended to $10^6$ cells per milliliter and spun onto a slide. The slides were stained using a Benzidine Wright-Giemsa staining protocol and the slide was visually analyzed. Photographs of slides are provided as FIG. 25. FIG. 25A being a control and FIG. 25B being a sample treated with CD31 antibody.

Example 12

Selection of Gestational Age for Blood Sample Collection for Fetal Cell Isolation from Maternal Blood Samples Blood samples were drawn from pregnant women at from about 11 to 16 weeks of gestation age. Samples were centrifuged at 1500 rpm (470×g) for 6 minutes and the supernatant aspirated away from the cell pellet, the cell pellet was resuspended in PBE and centrifuged for further washing. The second centrifugation step was done at two speeds, either 1500 rpm (470×g) for 10 minutes or 1000 rpm (209×g) for 2 minutes. The effect on fetal cell recovery is described in the following table:

|  |  |  | Fetal cells recovered | | | |
| --- | --- | --- | --- | --- | --- | --- |
|  |  | Gest | 2nd Centrifugation | | | |
| Sample | Anticoagulant | Age | 1500 × 10 | 1000 × 2 | W2 | Final |
| 7615 | Heparin | 15 | 2 | 1 | 0 | 2 |
| 7623 | Heparin | 13 | 2 | 3 | 0 | 2 |
| 7624 | Heparin | 12 | 1 | 3 | 2 | 3 |
| 7629 | Heparin | 14 | 0 | 1 | 0 | 0 |
| 7558 | Heparin | 14 | 3 | 7 | 1 | 3 |
| 7655 | ACD | 13 | 6 | 2 | 0 | 6 |
| 7674 | ACD | 16 | 4 | 0 | 3 | 4 |
| 7716 | ACD | 11 | 1 | 5 | 6 | 5 |
| Total enriched fetal cells |  |  | 19 | 22 |  | 25 |

The column labeled "W2" is the amount of fetal cells recovered from the supernatant after the second centrifugation step. The columns labeled "1500×10" and "1000×2" were the two centrifugation speeds chosen for the second centrifugation step. The column labeled "Final" was the amount of fetal cells enriched using the following parameter: if a samples had a gestation age of less than 13 weeks then the amount of fetal cells recovered was chosen from the column labeled 1000 rpm (209×g) for 2 min; and the samples had a gestation age of greater than or equal to 13 weeks, then the amount of fetal cells recovered was chosen from the column labeled 1500 rpm (470×g) for 10 min.

Example 13

Centrifugation Conditions for Fetal Cell Isolation from Maternal Blood Samples

Blood samples were drawn from pregnant women at about 11 to about 20 weeks of gestation. Samples of about 10 milliliters were centrifuged at 1500 rpm (470×g) for 6 minutes to wash the cells. The pellet was resuspended in approximately 45 milliliters of PBE and then centrifuged once more as a second wash at two speeds either 1500 rpm (470×g) for 10 minutes or 1000 rpm (209×g) for 2 minutes.

Enrichment of fetal nucleated RBCs from maternal blood was performed as follows:
Step One: Blood Debulking and WBC Removal.
(1) A Combined Reagent:
   The combined reagent has two components:
   c) RBC aggregation solution
      2% Dextran (110,000 MW)
      0.05 ugs/ml of IgM antibody to glycophorin A
      5 mM EDTA
      1×PBS without calcium and magnesium.
The RBC aggregation solution works with other saline based solutions including but not limited to 1× Hanks balanced saline solution. The anticoagulant can include but not limited to heparin, ACD or EDTA The concentration of antibody to glycophorin A can have a range of 0.01 to 10
   d) WBC depletion solution
      Magnetic beads (1.0 micron magnetic beads prepared by AVIVA), precoated with antibody (5-60 ugs per $10^9$ beads)
The combined reagent has the RBC aggregation solution with 15-60 precoated magnetic beads per WBC.
   (2) Use of the Combined Reagent:
   The combined reagent was added to an equal volume of washed peripheral blood and incubated with rotation for 30 minutes (range of 0.1-2 hour). The tube was settled for 0.5 hr (range of 0.1 to 2 hours) upright against a magnet (Dynal, MPC-1). We have also tested a magnet on the bottom of the tube as well.
   The solution from the top portion of the tube that did not include aggregated cells (on the side of the tube or at the bottom portion of the tube) was aspirated off and transferred to the next step.
Step Two: Further Enrichment of Fetal Cells and Removal of RBCs.
The aspirated solution can be then further processed to enrich for nucleated fetal cells and remove RBCs by either a magnetic separation step (e.g. antibody to CD71 with MACS microbeads) or a microfiltration step.

The column labeled "W2" is the amount of fetal cells recovered from the supernatant after the second centrifugation step. The columns labeled "1500×10" and "1000×2" were the two centrifugation speeds chosen for the second centrifugation step. The column labeled "Final" was the amount of fetal cells enriched using the following parameter: if a samples had a gestation age of less than 13 weeks then the amount of fetal cells recovered was chosen from the column labeled 1000 rpm (209×g) for 2 min; and the samples had a gestation age of greater than or equal to 13 weeks, then the amount of fetal cells recovered was chosen from the column labeled 1500 rpm (470×g) for 10 min.

Results:

| Sample | Anticoagulant | Gest Age | 1500 × 10 | 1000 × 2 | W2 | Final |
|---|---|---|---|---|---|---|
| 7615 | Heparin | 15 | 2 | 1 | 0 | 2 |
| 7623 | Heparin | 13 | 2 | 3 | 0 | 2 |
| 7624 | Heparin | 12 | 1 | 3 | 2 | 3 |
| 7629 | Heparin | 14 | 0 | 1 | 0 | 0 |
| 7558 | Heparin | 14 | 3 | 7 | 1 | 3 |
| 7655 | ACD | 13 | 6 | 2 | 0 | 6 |
| 7674 | ACD | 16 | 4 | 0 | 3 | 4 |
| 7716 | ACD | 11 | 1 | 5 | 6 | 5 |
|  |  |  | 19 | 22 |  | 25 |

Example 14

Fetal Cells Isolated from Maternal Blood

During enrichment of rare fetal cells using methods disclosed herein, the sample and various sample fractions were tested for the presence and abundance of nucleated fetal cells. This is presented schematically in FIG. 24. The figure shows a fetal cell enrichment procedure that begins with a maternal blood sample (upper left) and ends in a high-quality preparation of enriched fetal cells.

The steps of the enrichment procedure, going in sequential order and from upper left to lower right in the figure, are: 1) washing the blood sample (0-2 centrifugations); 2) selectively sedimenting red blood cells and selectively removing white blood cells with a Combined Reagent (PBS lacking calcium and magnesium containing: 5 millimolar EDTA, 2% dextran (molecular weight from 70 to 200 kilodaltons), 0.05 micrograms (range of 0.01 to 10) per milliliter of IgM antibodies to glycophorin A, and approximately $1-5 \times 10^9$ magnetic beads coated with a CD50 antibody); and 3) filtering the supernatant of step 2) through a microfabricated filter, such as the microfabricated filters described in Examples 15 and 16.

Figure 24:
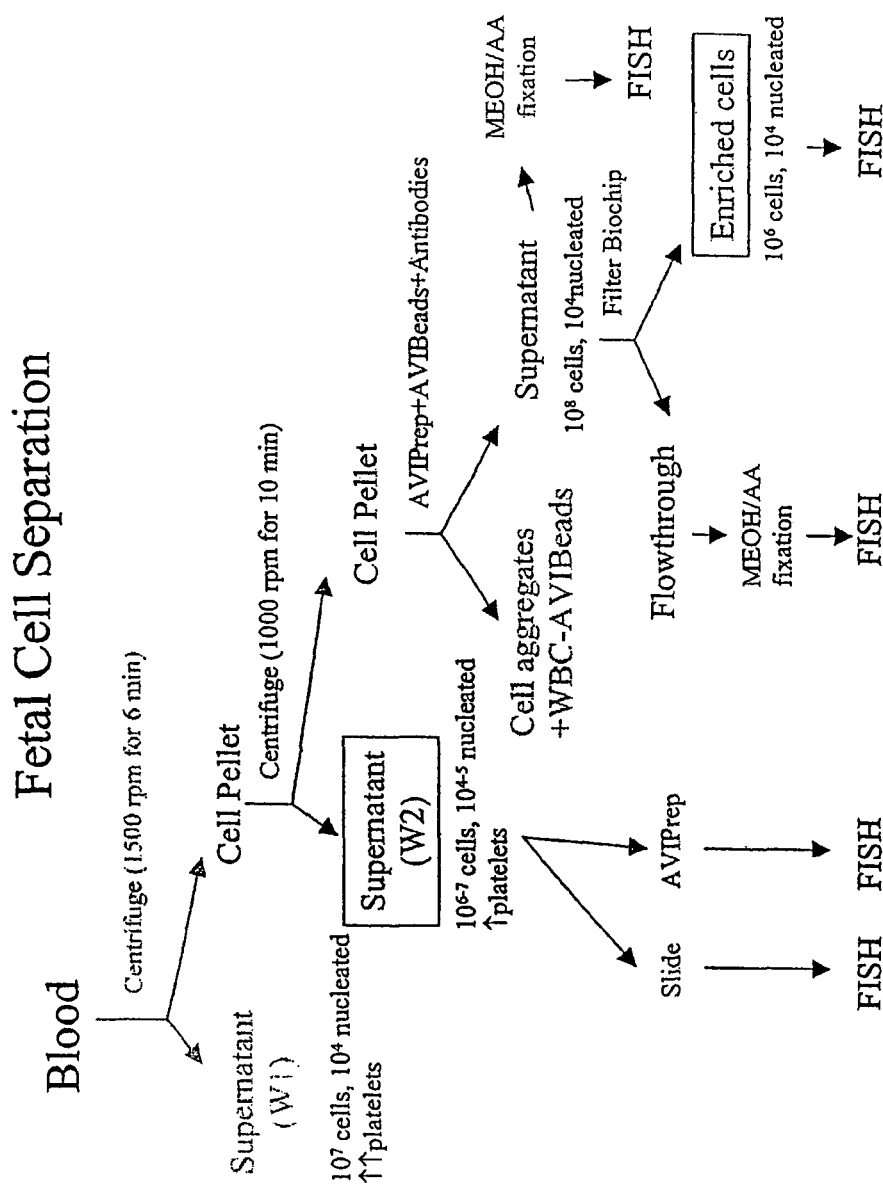
FIG. 24 is a diagram showing the overall process of fetal cell enrichment from a blood sample, and the presence of enriched fetal cells in the supernatant of a second wash of the blood sample (box labeled Supernatant (W2)) and in the retained cells after the filtration step (box labeled Enriched cells). The diagram shows, from upper left to lower right, blood cell processing steps" two washes (W1 and W2), Selective sedimentation of red blood cells and removal of white blood cells with a combined reagent (AVIPrep+AVIBeads+Antibodies), Filtration of the supernatant of the sedimentation, and collection of enriched fetal cells. The diagram shows the level of enrichment of nucleated cells of various sample fractions during the procedure, and the sample fractions that were analyzed using FISH.

In FIG. 24, "AVIPrep" refers a red blood cell sedimenting solution, for example, PBS lacking calcium and magnesium containing: 5 millimolar EDTA, 2% dextran (molecular weight from 70 to 200 kilodaltons), 0.05 micrograms per milliliter of IgM antibodies to glycophorin A. Also in FIG. 24, AVIBeads are magnetic beads for capturing white blood cells and "Antibodies" refer to antibodies that bind white blood cells.

By analyzing various fractions of the sample after processing steps using fluorescence in situ hybridization, the discovery was made that enriched fetal cells could be detected in the supernatant of the second wash (step 1, above; shown in the box as "Supernatant W2" in FIG. 24). The enrichment of fetal cells in the Wash 2 supernatant however was not as good as the enrichment of fetal cells collected after filtration (step 3) and their condition was relatively poor.

Fetal cells were isolated from maternal blood cells by centrifuging a blood sample at low speed (such as between 900 and 2000 rpm for 4 to 10 min.) and removing the supernatant (Wash 1). A buffer (PBE) was added to the cell pellet, and the sample was centrifuged again at low speed, at approximately 1000 rpm for 10 minutes (Wash 2). The supernatant from the second centrifugation was analyzed for the presence of nucleated cells. The Wash 2 supernatant was removed from the pellet and put in a fresh 50 ml tube. The supernatant was then centrifuged at a speed of 1500 rpm for 10 minutes. The supernatant from this pelleting step was removed, and the cell pellet was resuspended with AVIWash (PBE) to a small volume and Prepacyte Treatment was added in equal parts. Aliquots were put on slides and analyzed using an interphase FISH protocol. The nucleated fetal cells were seen to be intact. The figure shows the number of cells recovered.

Aliquots of sample and other sample fractions at specific steps of the overall enrichment procedure were also analyzed using FISH, as shown diagrammatically in FIG. 24. However, most of these fractions were not found to have satisfactory enrichment of fetal nucleated cells. Thus, the most consistent and satisfactory cells are located in the recovered cells after the filtration step. These cells are can be FISHed or labeled with antibodies and FISHed.

Example 15

Isolation of Fetal Cells from the Second Wash (W2) Supernatant Maternal Blood Sample In a representative experiment, a maternal blood sample with a gestational age of about 13 weeks was divided into three 10 milliliter aliquots, for enriching fetal cells.

Fetal cells were isolated from maternal blood cells by centrifuging the blood sample aliquots at 1500 rpm (about 470×g) for 6 min., with the brake set at 900 rpm (approximately 170×g) and removed the supernatant (Wash 1). PBE was added to the cell pellet, and the sample was centrifuged again at low speed, at 1000 rpm (approximately 209×g, range of 500-2200 rpm, approximately 52 to 1000×g) for 10 minutes (range of 2-30 minutes) with the brake set at 900 rpm approximately 170×g) (Wash 2). The break was released at 900 rpm (approximately 170×g) to minimize the vibration in the slowing down of the centrifuge rotor. This point may exist at different speeds in other centrifuges and could be avoided by removing the ability of the centrifuge to turn on the break.

The second wash (Wash 2 or W2) supernatants from the second centrifugation were analyzed for the presence of nucleated cells. The Wash 2 supernatants were removed from the cell pellets and put in fresh 50 ml tubes. The W2 supernatants were then centrifuged at a speed of 1500 rpm (approximately 470×g) for 10 minutes. The supernatants from this pelleting step was removed, and the cell pellets were resuspended in 750 microliters of PBE, for W2 supernatants from the 10 milliliter sample aliquots, respectively.

The resuspended W2 Supernant cells were processed in different ways. In one case, an equal volume of the RBC aggregation solution was added to the resuspended cells. In the other cases, beads coated with CD31 Antibody were added in 4×10^8 and 8×10^8 quantities to the pellet re-suspension. These samples were allowed to rotate for 0.5 hr (range of 5 to 120 minutes) and settle against a magnet for 0.5 hr (range of 5 to 120 minutes). After settling, the supernatant was allowed to flow through the silicon filter chip. Aliquots were put on slides and analyzed using an interphase FISH protocol. The nucleated fetal cells were seen to be intact. The figure shows the number of cells recovered.

Aliquots of sample and other sample fractions at various steps of the overall enrichment procedure were also analyzed using FISH, as shown diagrammatically in FIG. 24. However, most of these fractions were not found to have satisfactory enrichment of fetal nucleated cells.

Example 16

Separation of Rare Cells from a Blood Sample with Labeling of Blood Sample Components During Debulking (Fluorescent Prelabeling of Target Cells)

To isolate fetal cells from a maternal blood sample, 10 milliliters of maternal blood (gestational age 10-20 weeks is centrifuged at 1500 rpm (approximately 470×g) in a 50 milliliter conical tube for 6 minutes. The supernatant is aspirated to remove the supernatant, and then wash could be repeated. The supernatant was removed and five additional milliliters of PBE is added to the tube to bring the sample up to the original volume.

An equal volume (10 milliliters) of Aviprep (PBS lacking calcium and magnesium containing: 5 millimolar EDTA, 2% dextran (molecular weight from 70 to 200 kilodaltons), 0.05 micrograms per milliliter of IgM antibodies to glycophorin A) is added to the tube. An aliquot of antibody precoated magnetic beads that bind the antigen CD50 is added to the tube. To improve the enrichment of fetal cells, it is possible to add an aliquot of antibody precoated magnetic beads that bind to the antigen CD31 to the tube. Also, it is possible to add other precoated beads to increase the removal of WBCs and/or increase the amount of antibody to glycophorin A to increase removal of RBCs. In addition, it is possible to label the desired cells with a labeled antibody that binds to an antigen on the desired cells including but not limited to an antigen such as the transferring receptor (CD71). This labeled antibody can be conjugated to the fluorescent label (e.g. fluorescein labeled antibody to CD71, Leinco Technologies, St. Louis, Mo.) and added to the tube. The tube is inverted for 30 minutes (range of 5 to 120 minutes) at room temperature in the dark.

After incubation in a red blood cell sedimenting solution and specific binding members that bind white blood cells and platelets, the tube is positioned against a magnet and allowed to sit for 30 minutes (range of 5 to 120 minutes) in the dark to allow red blood cells to sediment and white blood cells and platelets to be captured. After 30 minutes, the supernatant (the phase above the aggregated red blood cells) is collected and place in a new tube. The tube is filled with PBE, inverted, and is centrifuged at 1000 rpm for 10 min to pellet cells. The supernatant is removed and the pelleted cells are resuspended in 10 uLs of PBE. The resuspended cells are placed on a microscope slide and allowed to dry. When viewed by fluorescence microscopy, labeled fetal cells are fluorescent and seen to be surface labeled.

A separate aliquot of the cell preparation is fixed and permeabalized for FISH using a DNA probe used to test for trisomy. The cells labeled with the labeled antibody will be cells which include nRBCs and fetal cells. It is possible to reduce the number of contaminating maternal cells based on the presence of the fluorescent surface label.

Example 17

Separation of Rare Cells from a Blood Sample with Labeling of Blood Sample Components During Separation of Undesirable Components for Further Enrichment of Rare Cells (Fluorescent Prelabeling of Target Cells)

To isolate fetal cells from a maternal blood sample, 10 milliliters of maternal blood (gestational age 10-20 weeks) is dispensed into a 50 milliliter conical tube. After washing the blood sample, an equal volume (10 milliliters) of Aviprep (PBS lacking calcium and magnesium containing: 5 millimolar EDTA, 2% dextran (molecular weight from 70 to 200 kilodaltons), 0.05 micrograms per milliliter of IgM antibodies to glycophorin A) is added to the tube. An aliquot of magnetic beads that bind CD50 and an aliquot of magnetic beads that CD31 are also added to the tube. In addition, a labeled antibody that binds CD71 and that is conjugated to a fluorescent label (e.g. fluorescein labeled antibody to CD71, Leinco Technologies, St. Louis, Mo.) is added to the tube. The label antibody is to an antigen present on the potential target cell (e.g. fetal cell). The tube is inverted for 30 minutes at room temperature in the dark.

After incubation in a red blood cell sedimenting solution and specific binding members that bind white blood cells and platelets, the tube is positioned against a magnet and allowed to sit for 30 minutes to allow red blood cells to sediment and white blood cells and platelets to be captured in the dark. After 30 minutes, the supernatant (the phase above the red blood cells) is collected and place in a new tube.

The recovered supernatant is then filtered through a filtration chamber having dimension of that comprises a filter having 3.2 micron wide slots that divides the filtration chamber into an antechamber and a post-filtration subchamber. The antechamber comprises a polycarbonate ball suspended from the loading reservoir inlet by four fins that are attached to the sides of the antechamber.

The sample is filtered at a rate of 20 milliliters per hour. After the reservoir is emptied, 3 additional milliliters of PBE is filtered through to wash the chamber. Finally, a backwash is performed in which the waste outlet is closes, and 5 milliliters of PBE is pumped into the lower post-filtration subchamber through the side outlet. The wash solution is pushed into the post-filtration chamber to dislodge any cells that may have collected or aggregated below the filter. The lower waste outlet is opened again, and filtration of the backwash through the filter is performed. After the backwash, the chamber is rotated and the filtered sample is collected from the antechamber The sample is then analyzed by flow cytometry and the labeled, nucleated cells are recovered. The cells are cytospun onto a slide and analyzed.

Another possibility is to have the supernatant removed after filtration and the pelleted cells are resuspended in 10 uLs of PBE. The resuspended cells are placed on a microscope slide and allowed to dry. When viewed by fluorescence microscopy, labeled nucleated cells are fluorescent and seen to be surface labeled. This would assist to identify potential fetal cells.

A separate aliquot of the cell preparation is fixed and permeabalized for FISH using a DNA probe used to test for trisomy. Fetal cells can be distinguished from maternal cells by the presence of the fluorescent surface label nucleated cells.

Example 18

Separation of Rare Cells from a Blood Sample with Labeling of Blood Sample Components During Separation of Undesirable Components for Enrichment of Rare Cells (Fluorescent Prelabeling of Non-Target Cells)

To isolate fetal cells from a maternal blood sample, 10 milliliters of maternal blood (gestational age 10-20 weeks) is dispensed into a 50 milliliter conical tube. After washing the blood sample and the sample is resuspend with PBE to the original volume, an equal volume (10 milliliters) of Aviprep (PBS lacking calcium and magnesium containing: 5 millimolar EDTA, 2% dextran (molecular weight from 70 to 200 kilodaltons), 0.05 micrograms per milliliter of IgM antibodies to glycophorin A) is added to the tube. An aliquot of magnetic beads that bind CD50 and an aliquot of magnetic beads that CD31 are also added to the tube. In addition, a labeled antibody that binds a cell surface marker (including but not limited to e.g. CD7) and that is conjugated to the detectable label (including but not limited to e.g. fluorescein labeled antibody to CD7, Ancell, Bayport, Minn.) is added to the tube. The labeled antibody is to an antigen that is not or minimally present on the potential desired cell (e.g. fetal cell), and one example is the antigen CD7 which is expressed less on the desired cells compared to WBCs. The tube is inverted for 30 minutes at room temperature in the dark.

After incubation in a red blood cell sedimenting solution and specific binding members that bind white blood cells and platelets, the tube is positioned against a magnet and allowed to sit for 30 minutes in the dark to allow red blood cells to sediment and white blood cells and platelets to be captured in the dark. After 30 minutes, the supernatant (the phase above the red blood cells) is collected and place in a new tube.

The recovered supernatant is then filtered through a filtration chamber having dimension that comprises a filter having 3.2 micron wide slots that divides the filtration chamber into an antechamber and a post-filtration subchamber. The sample is filtered at a rate of 20 milliliters per hour. After the reservoir is emptied, 3 additional milliliters of PBE is filtered through to wash the chamber. Finally, the bottom chamber wash is performed in which the top chamber outlet is closed, and 5 milliliters of PBE (five cycles of one milliliter PBE followed by a volume of air) is pumped into the lower post-filtration subchamber through the side outlet. The wash solution is pushed into the post-filtration chamber to dislodge any cells that may have collected or aggregated below the filter. The lower waste outlet is closed, and the top chamber inlet is opened, . . . . After the wash, the chamber is rotated and the filtered sample is collected from the antechamber The sample is then analyzed by flow cytometry and the unlabeled, nucleatedcells are recovered. The cells are cytospun onto a slide and analyzed.

Another possibility is to have the supernatant removed after filtration and the pelleted cells are resuspended in 10 uLs of PBE. The resuspended cells are placed on a microscope slide and allowed to dry. When viewed by fluorescence microscopy, labeled nucleated cells are fluorescent, seen to be surface labeled, and removed from analysis. This would assist to identify potential fetal cells, which would be unlabeled and nucleated.

A separate aliquot of the cell preparation is fixed and permeabalized for FISH using a DNA probe used to test for trisomy. Maternal cells can be distinguished from fetal cells by the presence of the fluorescent surface label nucleated cells.

Example 19

A Ball Cartridge Configuration May Permit Increased Sample Loading and Increased Yield of Fetal Cells From a Maternal Blood Sample A cartridge configuration for the filter chips referred to as a ball configuration was tested against a standard cartridge configuration for the ability to filter fetal cells from maternal blood. The ball-like configuration permitted increased sample loading and filtration, which resulted in increased fetal cell yield. Fetal cells were observed when 30 mL of blood was filtered using the ball cartridge configuration. The configuration of the cartridge is based on having a ball-shaped object in the middle of the top cartridge. The ball redirects the fluid flow to be more uniform in fluid distribution on the filter chip compared to a cartridge configuration without one. The present cartridge configuration has most of the fluid flow in the direct middle as shown in figure YY and this is compared to a ball cartridge configuration.

To demonstrate the increased fetal cell yield findings blood sample MB 7555 (as described) was used as the maternal blood sample. A total of 40 mL of MB #7555 was aliquoted into four separate 50 mL conical vials labeled samples 1, 2a, 2b and 2c. Each washed two times with PBE. Each was spun at 1500 rpm (approximately 470×g) for 6 min and aspirated to 7.5 mL. Each sample was returned into its original 10 mL volume with PBE. washed anti-CD50 precoated beads were added to samples 1 through 2c and washed anti-CD31 precoated beads were added to the samples. Each sample was rotated for 30 minutes. Each sample was uncapped and put into a Dynal magnet for 30 minutes at room temperature. The supernatant was recovered and filtered through a filter chip.

Sample 1 was added to a regular cartridge and samples 2a-2c were added to a ball cartridge. The captured cells were counted using a hemocytometer. The cells were then spun at 1000 rpm (approximately 209×g) for 10 min with brake off at zero. The supernatant was removed and cells were smeared onto the appropriate number of slides and air dried for 1 hr at room temperature.

Fixation Protocol

A portion of each sample was fixed for 15 minutes at room temperature in methanol (MeOH)/acetic acid (AA) at a ration of 3:1. Each washed in 2×SSC for four minutes at room temperature. Each was dehydrated in 70%, 90%, 100% ethanol for four minutes each at room temperature and allowed to air dry. Slides were viewed on a microscope to determine the amount of denaturing time.

XY FISH Protocol

For each slide use: 0.5 uL X Probe and 0.5 uL Y Probe, 7.0 uL Hybridization buffer, 2.0 distilled water. The hybridization mixture was put onto coverslips and the slide was turned upside down and placed on hybridization mixture. Each slide/coverslip was sealed with rubber cement. Slides were denatured at 80 degrees Celsius for an allotted time in Vysis Hybrite machine (Vysis, Downers Grove, Ill.). The slides were put into a slide rack in a Tupperware container containing damp paper towels and were hybridized overnight in an oven at 37 degrees Celsius. After incubation, the rubber cement and cover slip was removed. Each slide was singly placed in 0.4×SSC at 70 degrees Celsius for 30 seconds. Each slide was placed in 2×SSC with 0.1% NP40 at room temperature for 1 minute. The slides were removed, the backs wiped and allowed to air dry. A drop of Vectashield with DAPI (Vector Laboratories, Burlingame, Calif.) was place on a coverslip, placed on the slide and sealed with nail polish.

| | | |
|---|---|---|
| Experiment | XY FISH Polycarbonate Ball 30 mL | |
| Samples | MB7557, 13 weeks gestation, Jul. 27, 2004 drawn | |
| Operator | Jia Xu/Charina Schmitigal | |
| Date | Jul. 27, 2004 | |

| AviPrep | Sample 1 | Sample 2 |
|---|---|---|
| | Procedure and Results | |
| Time Drawn | 9:23 am | |
| Treatment | None | None |
| Type of wash buffer | PBE w/Heparin | PBE w/Heparin |
| Speed of the wash in rpms | twice at 1500 for 6 minutes | |
| Wash step | W1 and W2, aspirated to 7.5 mL | |
| Start samples in mls | 30 | 10 |
| AVISolution w/10 U/ml heparin | 10 mls each with 1.25 ug of GpA per 10 mls (GpA Lot#040715001) | |
| AVIsolution Specs. | Jul. 16, 2004 PGH | |
| RBCs per ml | 5.60E+09 | 5.60E+09 |
| Bead Manufactor | AVIVA | |
| WBCs per ml | 7.20E+06 | 7.20E+06 |
| Type & AVIBead storage buffer | 1.0 mm Neutravidin AVIBeads in Bang's buffer w/0.3% Azide | |
| Bead Lot | 040707001 for CD31 and 040621001 for CD50 | |
| Beads of CD50/WBC | 40 | 40 |
| µgs of CD50 per 10^9 beads | 25 | 25 |
| Lot of AVIVA CD50 | 030902004 | |
| Beads of CD31 | 1.00E+09 | 1.00E+09 |
| µgs of CD31 per 10^9 beads | 25 | 25 |
| Rock | 30 min at RT in one 50 ml Conical tube | |
| Magnetic Stand | 30 min at RT in Dynal magnet | |
| mls recovered | 40.5 | 13.2 |
| | SI Membrane Depletion | |
| Chip Manufacturer | Samsung | |
| Chip Name | T18_05 | T18_37 |
| Chip Type and Set-Up | Polycarbonate Ball, 30 mL Blood | Control |
| Speed (ml/hr) | 40 | 20 |
| Fetal Cells | 4 | 0 |
| Number of slides made | 3 | 4 |

Example 20

Validation of Fetal Cell Enrichment Protocol to Isolate Fetal Cells from Maternal Peripheral Blood To isolate fetal cells from a maternal peripheral blood sample, samples (9 milliliters per tube for a total of 27 mls) of maternal peripheral blood (gestational age 10-18 weeks) was dispensed into a three 50 milliliter conical tubes. Each tube containing an aliquot of blood was filled with PBE and washed once using a single centrifugation of 1000 rpms (~209×g) for 8 minutes. After removing the supernatant from the sample and resuspension of the sample with PBE to the original volume, an equal volume (9 milliliters) of AVIPrep (1×PBS lacking calcium and magnesium containing: 5 millimolar EDTA, 2% dextran (molecular weight from 70 to 200 kilodaltons), 0.15 micrograms of IgM antibody to glycophorin A per milliliter) is added to the tube. An aliquot of magnetic beads that bind CD50 (40 beads per white blood cell) and an aliquot of magnetic beads that CD31 (3.6×10$^9$ beads) were added to each tube.

After rotation at room temperature for 30 minutes (range of 5 to 120 minutes) in a red blood cell aggregating solution and magnetic specific binding members that bind white blood cells and platelets, the tube was positioned against a magnet for 30 minutes (range of 5-120 minutes). The red blood aggregates were allowed to sediment and white blood cells and platelets were captured by the magnet. The supernatant (the phase above the red blood cells) was collected and place in a new tube.

The supernatant was loaded into a filtration chamber containing a filter biochip (2.8 to 3.2 micron wide slots) that divides the filtration chamber into an antechamber and a post-filtration subchamber. After the reservoir containing the supernatant was emptied, 3 milliliters of PBE (three cycles of one milliliter PBE followed by a volume of air) was filtered through to wash the chamber. Finally, the bottom chamber wash was performed in which the top chamber outlet was closed, and 5 milliliters of PBE (five cycles of one milliliter PBE followed by a volume of air) was pumped into the lower post-filtration subchamber through the side outlet. The wash solution was pushed into the post-filtration chamber to dislodge any cells that may have collected or aggregated below the filter. The lower waste outlet was closed, and the top chamber inlet was opened. The chamber was rotated and the filtered sample containing the enriched cells was collected from the antechamber. The cells were pelleted using a centrifugation step (1000 rpm (~209×g) for 10 minutes) and the cells were placed onto a slide, fixed, hybridized to chromosome probes using interphase FISH and analyzed for Y$^+$ cells.

TABLE

Amount of male fetal cells isolated from peripheral blood of women carrying a male fetus.

| MB # | Total Fetal Cells (+ & ?) | Gestation |
|---|---|---|
| 6204 | 1 | 10 wk |
| 6212 | 2 | 10 wk |
| 6198 | 2 | 10 wk |
| 6250 | 2 | 12 wk |
| 6106 | 2 | 13 wk |
| 6110 | 2 | 13 wk |
| 6239 | 2 | 14 wk |
| 1163 | 2 | 12 wk |
| 6278 | 3 | 10 wk |
| 6202 | 3 | 11 wk |

TABLE-continued

Amount of male fetal cells isolated from peripheral blood of women carrying a male fetus.

| MB # | Total Fetal Cells (+ & ?) | Gestation |
| --- | --- | --- |
| 6258 | 3 | 11 wk |
| 6107 | 3 | 14 wk |
| 1155 | 3 | 17 wk |
| 6242 | 4 | 12 wk |
| 6118 | 4 | 15 wk |
| 6210 | 5 | 16 wk |
| 6272 | 10 | 11 wk |
| 6276 | 12 | 10 wk |
| 6189 | 12 | 17 wk |
| 6117 | 18 | 14 wk |
| 6266 | 2 | 17 wk |

Example 21

Fetal Cells Isolated from Maternal Peripheral Blood and Identification of Fetal Cells Using Immunocytochemistry or In Situ Hybridrization and Fluorescent In Situ Hybridization During enrichment of rare fetal cells using methods disclosed herein, the sample and various sample fractions were tested for the presence and abundance of nucleated fetal cells. This is presented schematically in FIG. 24. The figure shows a fetal cell enrichment procedure that begins with a maternal blood sample (upper left) and ends in a high-quality preparation of enriched fetal cells.

It is possible to include an identification step after cell enrichment and before FISH to identify fetal cells. It is also possible to utilize laser capture microdissection on labeled cells to obtain a higher purity of fetal cells. This could include using an instrument (e.g. Arcturus PixCell) to catapult the desired cell onto cap. Pulsing the laser through the cap to bridge the gap between the cap and desired cell and adheres to the target cell. Lifting the cap removes the target cell(s) now attached to the cap. Biomolecules can then be extracted from the cells using DNA, RNA or protein isolation kits.

One example is the following. The steps of the enrichment procedure, going in sequential order and from upper left to lower right in the figure, are: 1) washing the blood sample (1 or 2 centrifugations); 2) selectively sedimenting red blood cells and selectively removing white blood cells with a Combined Reagent (PBS lacking calcium and magnesium containing: 5 millimolar EDTA, 2% dextran (molecular weight from 70 to 200 kilodaltons), 0.125 or 0.15 micrograms per milliliter of IgM antibodies to glycophorin A, and approximately $1-5\times10^9$ magnetic beads coated with a CD50 antibody and approximately $1-4\times10^9$ magnetic beads coated with a CD31 antibody); and 3) filtering the supernatant of step 2) through a microfabricated filter, such as the microfabricated filters described in [Examples 15 and 16]. The sample then is deposited onto a microscope slide.

The cells are fixed with a fixation agent (100% S.T.F. (Streck, Omaha, Nebr.) for 10 minutes and S.T.F.-0.75% PFA for 4 minutes), washed in water, and washed in 1×PBS for 6 minutes each. The cells could then incubated with antibodies to the following antigens: including but not limited to anti-∈ hemoglobin, anti-γ hemoglobin, anti-α-fetoprotein, anti-Epidermal growth factor receptor (EGFR), and anti-c-erbB-2/HER2. Theses antibodies could be detected by primary fluorescent label, secondary antibody, enzymatic labeling or combination of all three.

It is also possible to use probes to the RNA or DNA sequence to identify RNA or DNA present in fetal cells. The cells could then incubated with nucleic acids (including but not limited to e.g. oligonucleotides, antisense RNA or DNA oligonucleotides, peptide nucleic acids) to hybridize with the following sequences: including but not limited to anti-∈ hemoglobin, anti-γ hemoglobin, anti-α-fetoprotein, anti-Epidermal growth factor receptor (EGFR), and anti-c-erbB-2/HER2. These sequences could be detected by primary fluorescent label, secondary antibody, enzymatic labeling or combination of all three.

After the immunohistochemistry or immunocytochemical or in situ hybridization reaction, the slides are washed and dehydrated with ethanol washes. The slides are denatured by an incubated at 80 degrees Celsius for 1.75 to 5 minutes with fluorescently labeled oligo-nucleotides (0.5 μl of CEP X and 0.5 μl of CEP Y (Vysis, Downers Grove, Ill.), 2 μl of dH₂O, and 7 μl of CEP buffer solution). After melting the DNA, the slides are incubated at 37 degrees Celsius overnight. The slides are washed at 70 degrees Celsius for 20-30 seconds in 0.4×SSC and once in 2×SSC and 0.1% Igepal CA-630 for 1 minute. The nuclei are stained with a nuclear specific fluorescent dye. An anti-fading reagent (e.g. Vector Shield Vector) is add to the cells and the slide is cover slipped. The cells on the slide are then read using fluorescent microscopy.

It is then possible to target the labeled cells for laser microdissection using the fluorescent label(s) as a cell marker. The labeled cell(s) could be targeted for laser microdissection after cell enrichment, after cell labeling step or after interphase FISH procedure. The slide can be transferred to a laser capture device and catapult the desired cell onto cap, which has been placed over the target area. Pulsing the laser through the cap causes the thermoplastic film to form a thin protrusion that bridges the gap between the cap and desired cell and adheres to the target cell. Lifting the cap removes the target cell(s) now attached to the cap. Biomolecules are extracted from the cells using DNA, RNA or protein isolation kits.

By obtaining a relative pure subpopulation containing the target cells of interest (e.g. fetal cells), it is now possible to study the cells directly. This would result in the ability to study a further enriched fetal cell subpopulation using many technologies including but not limited to mass spec (e.g. protein and SNP analysis), microarray (e.g. chromosome alterations, point or genomic alterations and SNP analysis), and whole genome amplification for analysis of single to few cells (e.g. study point mutations or genomic alterations).

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. A method of enriching rare cells from a blood sample, comprising:
   a) performing at least one debulking step on a blood sample; and
   b) selectively removing at least one type of undesirable component from said blood sample to enrich a rare cell of interest in said blood sample, wherein said at least one type of undesirable component is a white blood cell; wherein selectively removing the white blood cell from said blood sample comprises contacting said blood sample with an antibody or an antibody fragment that selectively binds to the white blood cell to be removed.

2. The method according to claim 1, wherein said antibody or antibody fragment is coupled to a solid support.

3. The method of claim 2, wherein said antibody or antibody fragment selectively binds to CD3, CD11b, CD14, CD17, CD31, CD45, CD50, CD53, CD63, CD69, CD81, CD84, CD102 or CD166.

4. The method of claim 3, wherein said antibody or antibody fragment selectively binds to CD50.

5. The method according to claim 1, wherein said blood sample is a serum-depleted blood sample or a preserved blood sample.

6. The method according to claim 1, wherein said blood sample is a peripheral blood sample.

7. The method according to claim 1, wherein said debulking step is a centrifugation step.

8. The method according to claim 1, wherein the debulking step removes red blood cells (RBC).

9. The method according claim 8, wherein red blood cells are removed by a method selected from the group consisting of sedimentation, lysis, or binding to a red blood cell specific binding member.

10. The method according to claim 1, wherein said antibody or antibody fragment is coupled to a magnetic bead, further wherein the white blood cell is removed from the sample by using a magnet to capture said magnetic bead to which said antibody or antibody fragment is coupled and bound.

11. The method according to claim 10, wherein said antibody or antibody fragment selectively binds to CD50.

12. The method according to claim 1, further comprising labeling said rare cells.

13. The method according to claim 12, wherein said rare cells are cancer cells or other non-hematopoietic cells.

14. The method according to claim 13, further comprising contacting said blood sample with a specific binding member that selectively binds to a second type of said undesirable component, wherein said blood sample is enriched by removal of said second type of undesirable component.

15. The method of claim 14, wherein said specific binding member is an antibody that selectively binds to CD31, CD36, CD41, CD42 (a, b or c), CD51, or CD51/61.

16. The method according to claim 11, further comprising labeling said rare cells.

17. The method according to claim 16, wherein said rare cells are cancer cells or other non-hematopoietic cells.

18. The method according to claim 17, further comprising contacting said blood sample with a specific binding member that selectively binds to a second type of said undesirable component, wherein said blood sample is enriched by removal of said second type of undesirable component.

19. The method of claim 18, wherein said specific binding member is an antibody that selectively binds to CD31, CD36, CD41, CD42 (a, b or c), CD51, or CD51/61.

20. A method for enriching cancer cells from a blood sample, comprising:
   a) removing red blood cells from the blood sample by lysis of said red blood cells or by selective sedimentation of said red blood cells;
   b) removing white blood cells from said blood sample by contacting said blood sample with magnetic beads to which a selective binding member is coupled, wherein said selective binding member is an antibody that specifically binds to CD50; and
   c) labeling at least one type of cancer cells.

21. The method of claim 20, further comprising a step of analyzing said at least one type of cancer cells using a method selected from the group consisting of spectral imaging, fluorescence microscopy, visible light microscopy, and manual or automated image analysis.

22. The method of claim 20, further comprising isolating said at least one type of cancer cells by fluorescence activated cell sorting or laser cytometry.

* * * * *